US009427285B2

(12) United States Patent
Deem et al.

(10) Patent No.: US 9,427,285 B2
(45) Date of Patent: *Aug. 30, 2016

(54) SYSTEMS AND METHODS FOR CREATING AN EFFECT USING MICROWAVE ENERGY TO SPECIFIED TISSUE

(75) Inventors: Mark E. Deem, Moutain View, CA (US); Dan Francis, Mountain View, CA (US); Jessi Ernest Johnson, Mountain View, CA (US); Steven Kim, Los Altos, CA (US); Alexey Salamini, San Francisco, CA (US); Ted Su, Sunnyvale, CA (US); Peter Smith, Kirkcaldy (GB); Dan Hallock, Redwood City, CA (US)

(73) Assignee: MIRAMAR LABS, INC., Santa Clara, CA (US)

( * ) Notice: Subject to any disclaimer, the term of this patent is extended or adjusted under 35 U.S.C. 154(b) by 1193 days.

This patent is subject to a terminal disclaimer.

(21) Appl. No.: 12/107,025

(22) Filed: Apr. 21, 2008

(65) Prior Publication Data
US 2008/0269851 A1    Oct. 30, 2008

Related U.S. Application Data

(63) Continuation-in-part of application No. PCT/US2008/060935, filed on Apr. 18, 2008, and a continuation-in-part of application No. PCT/US2008/060929, filed on Apr. 18, 2008, and a
(Continued)

(51) Int. Cl.
*A61B 18/18*    (2006.01)
*A61B 18/02*    (2006.01)
(Continued)

(52) U.S. Cl.
CPC ........... *A61B 18/1815* (2013.01); *A61B 18/18* (2013.01); *A61N 5/02* (2013.01);
(Continued)

(58) Field of Classification Search
CPC .............................. A61B 18/1815–2018/1892
USPC ..................................................... 607/96–101
See application file for complete search history.

(56) References Cited

U.S. PATENT DOCUMENTS 2,407,690 A    9/1946 Southworth
3,307,553 A    3/1967 Liebner
(Continued)

FOREIGN PATENT DOCUMENTS

EP    0 139 607    5/1984
EP    0 370 890    11/1989
(Continued)

OTHER PUBLICATIONS
U.S. Appl. No. 09/637,923, filed Aug. 14, 2000, Spertell.
(Continued)

*Primary Examiner* — Emily Schmidt
*Assistant Examiner* — William Frehe
(74) *Attorney, Agent, or Firm* — Shay Glenn LLP

(57) ABSTRACT

Systems, methods and devices for creating an effect using microwave energy to specified tissue are disclosed. A system for the application of microwave energy to a tissue includes a signal generator adapted to generate a microwave signal having predetermined characteristics, an applicator connected to the generator and adapted to apply microwave energy to tissue. The applicator includes one or more microwave antennas and a tissue interface, a vacuum source connected to the tissue interface, a cooling source connected to the tissue interface, and a controller adapted to control the signal generator, the vacuum source, and the coolant source. The tissue includes a first layer and a second layer, the second layer below the first layer. The controller is configured so that the system delivers energy such that a peak power loss density profile is created in the second layer.

12 Claims, 40 Drawing Sheets

Related U.S. Application Data continuation-in-part of application No. PCT/US2008/060940, filed on Apr. 18, 2008, and a continuation-in-part of application No. PCT/US2008/060922, filed on Apr. 18, 2008.

(60) Provisional application No. 60/912,899, filed on Apr. 19, 2007, provisional application No. 61/013,274, filed on Dec. 12, 2007, provisional application No. 61/045,937, filed on Apr. 17, 2008.

(51) Int. Cl.
  *A61N 5/02* (2006.01)
  *A61B 18/00* (2006.01)
  *A61F 7/00* (2006.01)

(52) U.S. Cl.
  CPC .......... *A61B2018/00005* (2013.01); *A61B 2018/00023* (2013.01); *A61B 2018/00029* (2013.01); *A61B 2018/00041* (2013.01); *A61B 2018/00291* (2013.01); *A61F 2007/0075* (2013.01)

(56) References Cited

U.S. PATENT DOCUMENTS

| | | |
|---|---|---|
| 3,527,227 A | 9/1970 | Fritz |
| 3,693,623 A | 9/1972 | Harte et al. |
| 3,845,267 A | 10/1974 | Fitzmayer |
| 4,069,827 A | 1/1978 | Dominy |
| 4,095,602 A | 6/1978 | Leveen |
| 4,108,147 A | 8/1978 | Kantor |
| 4,140,130 A | 2/1979 | Storm, III |
| 4,174,713 A | 11/1979 | Mehl |
| 4,190,053 A | 2/1980 | Sterzer |
| 4,190,056 A | 2/1980 | Tapper et al. |
| 4,197,860 A | 4/1980 | Sterzer |
| 4,228,809 A | 10/1980 | Paglione |
| 4,375,220 A | 3/1983 | Matvias |
| 4,378,806 A | 4/1983 | Henley-Cohn |
| 4,388,924 A | 6/1983 | Weissman et al. |
| 4,397,313 A | 8/1983 | Vaguine |
| 4,397,314 A | 8/1983 | Vaguine |
| 4,446,874 A | 5/1984 | Vaguine |
| 4,528,991 A * | 7/1985 | Dittmar et al. .............. 607/156 |
| 4,589,424 A | 5/1986 | Vaguine |
| 4,597,379 A | 7/1986 | Kihn et al. |
| 4,614,191 A * | 9/1986 | Perler .............. 607/96 |
| 4,617,926 A | 10/1986 | Sutton |
| 4,632,128 A | 12/1986 | Paglione et al. |
| 4,641,649 A | 2/1987 | Walinsky et al. |
| 4,669,475 A | 6/1987 | Turner |
| 4,672,980 A | 6/1987 | Turner |
| 4,690,156 A | 9/1987 | Kikuchi et al. |
| 4,702,262 A | 10/1987 | Andersen et al. |
| 4,744,372 A | 5/1988 | Kikuchi et al. |
| 4,747,416 A | 5/1988 | Kikuchi et al. |
| 4,800,899 A | 1/1989 | Elliott |
| 4,825,880 A | 5/1989 | Stauffer et al. |
| 4,841,989 A | 6/1989 | Kikuchi et al. |
| 4,841,990 A | 6/1989 | Kikuchi et al. |
| 4,860,752 A | 8/1989 | Turner |
| 4,881,543 A | 11/1989 | Trembly et al. |
| 4,891,483 A | 1/1990 | Kikuchi et al. |
| 4,945,912 A | 8/1990 | Langberg |
| 4,974,587 A | 12/1990 | Turner et al. |
| 5,059,192 A | 10/1991 | Zaias |
| 5,097,846 A | 3/1992 | Larsen |
| 5,101,836 A | 4/1992 | Lee |
| 5,107,832 A | 4/1992 | Guibert et al. |
| 5,143,063 A | 9/1992 | Fellner |
| 5,186,181 A | 2/1993 | Franconi et al. |
| 5,190,518 A | 3/1993 | Takasu |
| 5,198,776 A | 3/1993 | Carr |
| 5,226,907 A | 7/1993 | Tankovich |
| 5,234,004 A | 8/1993 | Hascoet et al. |
| 5,246,438 A | 9/1993 | Langberg |
| 5,272,301 A | 12/1993 | Finger et al. |
| 5,295,955 A | 3/1994 | Rosen et al. |
| 5,301,692 A | 4/1994 | Knowlton |
| 5,305,748 A | 4/1994 | Wilk |
| 5,315,994 A | 5/1994 | Guibert et al. |
| 5,316,000 A | 5/1994 | Chapelon et al. |
| 5,364,336 A | 11/1994 | Carr |
| 5,364,394 A | 11/1994 | Mehl |
| 5,383,917 A | 1/1995 | Desai et al. |
| 5,385,544 A | 1/1995 | Edwards et al. |
| 5,405,346 A | 4/1995 | Grundy et al. |
| 5,407,440 A | 4/1995 | Zinreich et al. |
| 5,409,484 A | 4/1995 | Erlich et al. |
| 5,421,819 A | 6/1995 | Edwards et al. |
| 5,425,728 A | 6/1995 | Tankovich |
| 5,431,650 A | 7/1995 | Cosmescu |
| 5,433,740 A | 7/1995 | Yamaguchi |
| 5,441,532 A | 8/1995 | Fenn |
| 5,443,487 A | 8/1995 | Guibert et al. |
| 5,462,521 A | 10/1995 | Brucker et al. |
| 5,474,071 A | 12/1995 | Chapelon et al. |
| 5,480,417 A | 1/1996 | Hascoet et al. |
| 5,503,150 A | 4/1996 | Evans |
| 5,507,741 A | 4/1996 | L'Esperance, Jr. |
| 5,507,790 A | 4/1996 | Weiss |
| 5,509,929 A | 4/1996 | Hascoet et al. |
| 5,522,814 A | 6/1996 | Bernaz |
| 5,531,662 A | 7/1996 | Carr |
| 5,540,681 A | 7/1996 | Strul et al. |
| 5,549,639 A | 8/1996 | Ross |
| 5,553,612 A | 9/1996 | Lundback |
| 5,569,237 A | 10/1996 | Beckenstein |
| 5,571,154 A | 11/1996 | Ren |
| 5,575,789 A | 11/1996 | Bell et al. |
| 5,584,830 A | 12/1996 | Ladd et al. |
| 5,586,981 A | 12/1996 | Hu |
| 5,595,568 A | 1/1997 | Anderson et al. |
| 5,649,973 A | 7/1997 | Tierney et al. |
| 5,660,836 A | 8/1997 | Knowlton |
| 5,662,110 A | 9/1997 | Carr |
| 5,669,916 A | 9/1997 | Anderson |
| 5,674,219 A | 10/1997 | Monson et al. |
| 5,683,381 A | 11/1997 | Carr et al. |
| 5,683,382 A | 11/1997 | Lenihan et al. |
| 5,690,614 A | 11/1997 | Carr et al. |
| 5,707,403 A | 1/1998 | Grove et al. |
| 5,724,966 A | 3/1998 | Lundback |
| 5,733,269 A | 3/1998 | Fuisz |
| 5,735,844 A | 4/1998 | Anderson et al. |
| 5,742,392 A | 4/1998 | Anderson et al. |
| 5,743,899 A | 4/1998 | Zinreich |
| 5,755,753 A | 5/1998 | Knowlton |
| 5,769,879 A | 6/1998 | Richards et al. |
| 5,776,127 A | 7/1998 | Anderson et al. |
| 5,782,897 A | 7/1998 | Carr |
| 5,810,801 A | 9/1998 | Anderson et al. |
| 5,810,804 A | 9/1998 | Gough et al. |
| 5,814,996 A | 9/1998 | Winter |
| 5,824,023 A | 10/1998 | Anderson |
| 5,830,208 A | 11/1998 | Muller |
| 5,836,999 A | 11/1998 | Eckhouse et al. |
| 5,868,732 A | 2/1999 | Waldman et al. |
| 5,871,524 A | 2/1999 | Knowlton |
| 5,879,346 A | 3/1999 | Waldman et al. |
| 5,891,094 A | 4/1999 | Masterson et al. |
| 5,897,549 A | 4/1999 | Tankovich |
| 5,902,263 A | 5/1999 | Patterson et al. |
| 5,904,709 A | 5/1999 | Arndt et al. |
| 5,919,218 A | 7/1999 | Carr |
| 5,919,219 A | 7/1999 | Knowlton |
| 5,928,797 A | 7/1999 | Vineberg |
| 5,931,860 A | 8/1999 | Reid et al. |
| 5,948,011 A | 9/1999 | Knowlton |
| 5,949,845 A | 9/1999 | Sterzer |
| 5,971,982 A | 10/1999 | Betsill et al. |
| 5,979,454 A | 11/1999 | Anvari et al. |

(56) References Cited

U.S. PATENT DOCUMENTS

| | | |
|---|---|---|
| 5,983,124 A | 11/1999 | Carr |
| 5,983,900 A | 11/1999 | Clement et al. |
| 5,989,245 A | 11/1999 | Prescott |
| 6,015,404 A | 1/2000 | Altshuler et al. |
| 6,024,095 A | 2/2000 | Stanley, III |
| 6,026,331 A | 2/2000 | Feldberg et al. |
| 6,026,816 A | 2/2000 | McMillan et al. |
| 6,030,378 A | 2/2000 | Stewart |
| 6,036,632 A | 3/2000 | Whitmore, III et al. |
| 6,047,215 A | 4/2000 | McClure et al. |
| 6,050,990 A | 4/2000 | Tankovich et al. |
| 6,077,294 A | 6/2000 | Cho et al. |
| 6,080,146 A | 6/2000 | Altshuler et al. |
| 6,093,186 A | 7/2000 | Goble |
| 6,097,985 A | 8/2000 | Kasevich et al. |
| 6,104,959 A | 8/2000 | Spertell |
| 6,106,514 A | 8/2000 | O'Donnell, Jr. |
| 6,113,559 A | 9/2000 | Klopotek |
| 6,113,593 A | 9/2000 | Tu et al. |
| 6,126,636 A | 10/2000 | Naka |
| 6,129,696 A | 10/2000 | Sibalis |
| 6,139,569 A | 10/2000 | Ingle et al. |
| 6,149,644 A | 11/2000 | Xie |
| 6,162,212 A | 12/2000 | Kreindel et al. |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,181,970 B1 | 1/2001 | Kasevich |
| 6,183,773 B1 | 2/2001 | Anderson |
| 6,187,001 B1 | 2/2001 | Azar et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,231,569 B1 | 5/2001 | Bek et al. |
| 6,235,016 B1 | 5/2001 | Stewart |
| 6,241,753 B1 | 6/2001 | Knowlton |
| 6,245,062 B1 | 6/2001 | Berube et al. |
| 6,264,652 B1 | 7/2001 | Eggers et al. |
| 6,273,884 B1 | 8/2001 | Altshuler et al. |
| 6,277,104 B1 | 8/2001 | Lasko et al. |
| 6,277,111 B1 | 8/2001 | Clement et al. |
| 6,277,116 B1 | 8/2001 | Utely et al. |
| 6,280,441 B1 | 8/2001 | Ryan |
| 6,283,956 B1 | 9/2001 | McDaniel |
| 6,283,987 B1 | 9/2001 | Laird et al. |
| 6,287,302 B1 | 9/2001 | Berube |
| 6,290,699 B1 | 9/2001 | Hall et al. |
| 6,293,941 B1 | 9/2001 | Strul et al. |
| 6,306,128 B1 | 10/2001 | Waldman et al. |
| 6,306,130 B1 | 10/2001 | Anderson et al. |
| 6,312,427 B1 | 11/2001 | Berube et al. |
| 6,319,211 B1 | 11/2001 | Ito et al. |
| 6,322,584 B2 | 11/2001 | Ingle et al. |
| 6,325,769 B1 | 12/2001 | Klopotek |
| 6,330,479 B1 | 12/2001 | Stauffer |
| 6,334,074 B1 | 12/2001 | Spertell |
| 6,347,251 B1 | 2/2002 | Deng |
| 6,350,263 B1 | 2/2002 | Wetzig et al. |
| 6,350,276 B1 | 2/2002 | Knowlton |
| 6,361,531 B1 | 3/2002 | Hissong |
| 6,364,876 B1 | 4/2002 | Erb et al. |
| 6,377,854 B1 | 4/2002 | Knowlton |
| 6,383,176 B1 | 5/2002 | Connors et al. |
| 6,383,182 B1 | 5/2002 | Berube et al. |
| 6,387,103 B2 | 5/2002 | Shadduck |
| 6,387,380 B1 | 5/2002 | Knowlton |
| 6,402,739 B1 | 6/2002 | Neev |
| 6,405,090 B1 | 6/2002 | Knowlton |
| 6,409,720 B1 | 6/2002 | Hissong et al. |
| 6,409,722 B1 | 6/2002 | Hoey et al. |
| 6,413,253 B1 | 7/2002 | Koop et al. |
| 6,413,254 B1 | 7/2002 | Hissong et al. |
| 6,413,255 B1 | 7/2002 | Stern |
| 6,425,912 B1 | 7/2002 | Knowlton |
| 6,427,089 B1 | 7/2002 | Knowlton |
| 6,428,532 B1 | 8/2002 | Doukas et al. |
| 6,430,446 B1 | 8/2002 | Knowlton |
| 6,436,094 B1 | 8/2002 | Reuter |
| 6,436,127 B1 | 8/2002 | Anderson et al. |
| 6,443,914 B1 | 9/2002 | Costantino |
| 6,443,946 B2 | 9/2002 | Clement et al. |
| 6,451,013 B1 | 9/2002 | Bays et al. |
| 6,451,015 B1 | 9/2002 | Rittman, III et al. |
| 6,457,476 B1 | 10/2002 | Elmer et al. |
| 6,461,378 B1 | 10/2002 | Knowlton |
| 6,468,235 B2 | 10/2002 | Ito et al. |
| 6,470,216 B1 | 10/2002 | Knowlton |
| 6,471,662 B1 | 10/2002 | Jaggy et al. |
| 6,471,696 B1 | 10/2002 | Berube et al. |
| 6,475,179 B1 | 11/2002 | Wang et al. |
| 6,475,211 B2 | 11/2002 | Chess et al. |
| 6,480,746 B1 | 11/2002 | Ingle et al. |
| 6,485,484 B1 | 11/2002 | Connors et al. |
| 6,485,703 B1 | 11/2002 | Coté et al. |
| 6,500,141 B1 | 12/2002 | Irion et al. |
| 6,508,813 B1 | 1/2003 | Altshuler |
| 6,514,250 B1 | 2/2003 | Jahns et al. |
| 6,517,532 B1 | 2/2003 | Altshuler et al. |
| 6,529,778 B2 | 3/2003 | Prutchi |
| 6,558,382 B2 | 5/2003 | Jahns et al. |
| 6,575,969 B1 | 6/2003 | Rittman, III et al. |
| 6,577,903 B1 | 6/2003 | Cronin et al. |
| 6,584,360 B2 | 6/2003 | Francischelli et al. |
| 6,585,733 B2 | 7/2003 | Wellman |
| 6,595,934 B1 | 7/2003 | Hissong et al. |
| 6,600,951 B1 | 7/2003 | Anderson |
| 6,605,080 B1 | 8/2003 | Altshuler et al. |
| 6,607,498 B2 | 8/2003 | Eshel |
| 6,626,854 B2 | 9/2003 | Friedman et al. |
| 6,628,990 B1 | 9/2003 | Habib et al. |
| 6,629,974 B2 | 10/2003 | Penny et al. |
| 6,645,162 B2 | 11/2003 | Friedman et al. |
| 6,648,904 B2 | 11/2003 | Altshuler et al. |
| 6,652,518 B2 | 11/2003 | Wellman et al. |
| 6,653,618 B2 | 11/2003 | Zenzie |
| 6,662,054 B2 | 12/2003 | Kreindel et al. |
| 6,663,659 B2 | 12/2003 | McDaniel |
| 6,676,654 B1 | 1/2004 | Balle Petersen et al. |
| 6,676,655 B2 | 1/2004 | McDaniel |
| 6,682,501 B1 | 1/2004 | Nelson et al. |
| 6,692,450 B1 | 2/2004 | Coleman |
| 6,723,090 B2 | 4/2004 | Altshuler et al. |
| 6,725,095 B2 | 4/2004 | Fenn et al. |
| 6,736,810 B2 | 5/2004 | Hoey et al. |
| 6,743,222 B2 | 6/2004 | Durkin et al. |
| 6,749,624 B2 | 6/2004 | Knowlton |
| 6,763,836 B2 | 7/2004 | Tasto et al. |
| 6,766,202 B2 | 7/2004 | Underwood et al. |
| 6,807,446 B2 | 10/2004 | Fenn et al. |
| 6,808,532 B2 | 10/2004 | Andersen et al. |
| 6,821,274 B2 | 11/2004 | McHale et al. |
| 6,823,216 B1 | 11/2004 | Salomir et al. |
| 6,824,542 B2 | 11/2004 | Jay |
| 6,856,839 B2 | 2/2005 | Litovitz |
| 6,861,954 B2 | 3/2005 | Levin |
| 6,878,144 B2 | 4/2005 | Altshuler et al. |
| 6,878,147 B2 | 4/2005 | Prakash et al. |
| 6,881,212 B1 | 4/2005 | Clement et al. |
| 6,887,238 B2 | 5/2005 | Jahns et al. |
| 6,887,239 B2 | 5/2005 | Elstrom et al. |
| 6,887,260 B1 | 5/2005 | McDaniel |
| 6,888,319 B2 | 5/2005 | Inochkin et al. |
| 6,897,238 B2 | 5/2005 | Anderson |
| 6,907,879 B2 | 6/2005 | Drinan et al. |
| 6,916,316 B2 | 7/2005 | Jay |
| 6,918,908 B2 | 7/2005 | Bonner et al. |
| 6,939,344 B2 | 9/2005 | Kreindel |
| 6,939,346 B2 | 9/2005 | Kannenberg et al. |
| 6,955,672 B2 | 10/2005 | Cense et al. |
| 6,974,415 B2 | 12/2005 | Cerwin et al. |
| 6,976,984 B2 | 12/2005 | Cense et al. |
| 6,997,923 B2 | 2/2006 | Anderson et al. |

(56) References Cited

U.S. PATENT DOCUMENTS

| | | |
|---|---|---|
| 7,004,942 B2 | 2/2006 | Laird et al. |
| 7,006,874 B2 | 2/2006 | Knowlton et al. |
| 7,022,121 B2 | 4/2006 | Stern et al. |
| 7,029,469 B2 | 4/2006 | Vasily |
| 7,033,352 B1 | 4/2006 | Gauthier et al. |
| 7,044,959 B2 | 5/2006 | Anderson et al. |
| 7,052,491 B2 | 5/2006 | Erb et al. |
| 7,056,318 B2 | 6/2006 | Black |
| 7,066,929 B1 | 6/2006 | Azar et al. |
| 7,074,218 B2 | 7/2006 | Washington et al. |
| 7,081,111 B2 | 7/2006 | Svaasand et al. |
| 7,089,054 B2 | 8/2006 | Palti |
| 7,107,997 B1 | 9/2006 | Moses et al. |
| 7,115,123 B2 | 10/2006 | Knowlton et al. |
| 7,115,126 B2 | 10/2006 | Berube et al. |
| 7,118,590 B1 | 10/2006 | Cronin |
| 7,122,029 B2 | 10/2006 | Koop et al. |
| 7,128,739 B2 | 10/2006 | Prakash et al. |
| 7,135,033 B2 | 11/2006 | Altshuler et al. |
| 7,136,699 B2 | 11/2006 | Palti |
| 7,141,049 B2 | 11/2006 | Stern et al. |
| 7,151,964 B2 | 12/2006 | Desai et al. |
| 7,153,256 B2 | 12/2006 | Riehl et al. |
| 7,153,285 B2 | 12/2006 | Lauman et al. |
| 7,163,536 B2 | 1/2007 | Godara |
| 7,175,950 B2 | 2/2007 | Anderson et al. |
| 7,189,230 B2 | 3/2007 | Knowlton |
| 7,192,429 B2 | 3/2007 | Trembly |
| 7,204,832 B2 | 4/2007 | Altshuler et al. |
| 7,217,265 B2 | 5/2007 | Hennings et al. |
| 7,220,254 B2 | 5/2007 | Altshuler et al. |
| 7,220,778 B2 | 5/2007 | Anderson et al. |
| 7,229,436 B2 | 6/2007 | Stern et al. |
| 7,234,739 B2 | 6/2007 | Saitoh et al. |
| 7,238,182 B2 | 7/2007 | Swoyer et al. |
| 7,241,291 B2 | 7/2007 | Kreindel et al. |
| 7,247,155 B2 | 7/2007 | Hoey et al. |
| 7,250,047 B2 | 7/2007 | Anderson et al. |
| 7,252,628 B2 | 8/2007 | Van Hal et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,290,326 B2 | 11/2007 | Dutton |
| 7,309,335 B2 | 12/2007 | Altshuler et al. |
| 7,311,674 B2 | 12/2007 | Gingrich et al. |
| 7,329,273 B2 | 2/2008 | Altshuler et al. |
| 7,329,274 B2 | 2/2008 | Altshuler et al. |
| 7,331,951 B2 | 2/2008 | Eshel et al. |
| 7,344,587 B2 | 3/2008 | Khan et al. |
| 7,347,855 B2 | 3/2008 | Eshel et al. |
| 7,351,252 B2 | 4/2008 | Altshuler et al. |
| 7,354,448 B2 | 4/2008 | Altshuler et al. |
| 7,367,341 B2 | 5/2008 | Anderson et al. |
| 7,377,917 B2 | 5/2008 | Trembly |
| 7,387,627 B2 | 6/2008 | Erb et al. |
| 7,399,297 B2 | 7/2008 | Ikadai et al. |
| 7,422,586 B2 | 9/2008 | Morris et al. |
| 7,422,598 B2 | 9/2008 | Altshuler et al. |
| 7,431,718 B2 | 10/2008 | Ikadai |
| 7,470,270 B2 | 12/2008 | Azar et al. |
| 7,479,101 B2 | 1/2009 | Hunter et al. |
| 7,481,807 B2 | 1/2009 | Knudsen et al. |
| 7,491,171 B2 | 2/2009 | Barthe et al. |
| 7,524,328 B2 | 4/2009 | Connors et al. |
| 7,530,356 B2 | 5/2009 | Slayton et al. |
| 7,530,958 B2 | 5/2009 | Slayton et al. |
| 7,540,869 B2 | 6/2009 | Altshuler et al. |
| 7,544,204 B2 | 6/2009 | Krespi et al. |
| 7,565,207 B2 | 7/2009 | Turner et al. |
| 7,568,619 B2 | 8/2009 | Todd et al. |
| 7,588,547 B2 | 9/2009 | Deem et al. |
| 7,599,745 B2 | 10/2009 | Palti |
| 7,601,128 B2 | 10/2009 | Deem et al. |
| 7,613,523 B2 | 11/2009 | Eggers et al. |
| 7,630,774 B2 | 12/2009 | Karni et al. |
| 7,643,883 B2 | 1/2010 | Kreindel |
| 7,682,321 B2 | 3/2010 | Naldoni |
| 7,722,535 B2 | 5/2010 | Randlov et al. |
| 7,722,600 B2 | 5/2010 | Connors et al. |
| 7,722,656 B1 | 5/2010 | Segal |
| 7,736,360 B2 | 6/2010 | Mody et al. |
| 7,740,600 B2 | 6/2010 | Slatkine et al. |
| 7,740,651 B2 | 6/2010 | Barak et al. |
| 7,749,260 B2 | 7/2010 | Da Silva et al. |
| 7,758,524 B2 | 7/2010 | Barthe et al. |
| 7,758,537 B1 | 7/2010 | Brunell et al. |
| 7,762,964 B2 | 7/2010 | Slatkine |
| 7,763,060 B2 | 7/2010 | Baumann |
| 7,771,421 B2 | 8/2010 | Stewart et al. |
| 7,799,019 B2 | 9/2010 | Turovskiy et al. |
| 7,805,201 B2 | 9/2010 | Palti |
| 7,815,570 B2 | 10/2010 | Eshel et al. |
| 7,815,633 B2 | 10/2010 | Zanelli et al. |
| 7,824,394 B2 | 11/2010 | Manstein |
| 7,828,734 B2 | 11/2010 | Azhari et al. |
| 7,837,694 B2 | 11/2010 | Tethrake et al. |
| 7,842,029 B2 | 11/2010 | Anderson et al. |
| 7,854,754 B2 | 12/2010 | Ting et al. |
| 7,857,773 B2 | 12/2010 | Desilets et al. |
| 7,857,775 B2 | 12/2010 | Rosenberg et al. |
| 7,862,564 B2 | 1/2011 | Goble |
| 7,864,129 B2 | 1/2011 | Konishi |
| 7,891,362 B2 | 2/2011 | Domankevitz et al. |
| 7,905,844 B2 | 3/2011 | Desilets et al. |
| 8,211,099 B2 | 7/2012 | Buysse et al. |
| 8,401,668 B2 * | 3/2013 | Deem .................... A61B 18/18 607/101 |
| 2001/0005775 A1 | 6/2001 | Samson |
| 2001/0016761 A1 * | 8/2001 | Rudie et al. ................ 607/101 |
| 2001/0050083 A1 | 12/2001 | Marchitto et al. |
| 2002/0062124 A1 | 5/2002 | Keane |
| 2002/0062142 A1 | 5/2002 | Knowlton |
| 2002/0087151 A1 | 7/2002 | Mody et al. |
| 2002/0156471 A1 | 10/2002 | Stern et al. |
| 2002/0165529 A1 | 11/2002 | Danek |
| 2002/0193851 A1 | 12/2002 | Silverman et al. |
| 2003/0004082 A1 | 1/2003 | Masschelein et al. |
| 2003/0060811 A1 | 3/2003 | McDaniel |
| 2003/0130575 A1 | 7/2003 | Desai |
| 2003/0130711 A1 * | 7/2003 | Pearson et al. .............. 607/101 |
| 2003/0158566 A1 | 8/2003 | Brett |
| 2003/0199866 A1 | 10/2003 | Stern et al. |
| 2003/0212393 A1 | 11/2003 | Knowlton et al. |
| 2003/0216728 A1 | 11/2003 | Stern et al. |
| 2003/0220635 A1 | 11/2003 | Knowlton et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0034346 A1 | 2/2004 | Stern et al. |
| 2004/0049251 A1 | 3/2004 | Knowlton |
| 2004/0073079 A1 | 4/2004 | Altshuler et al. |
| 2004/0073115 A1 | 4/2004 | Horzewski et al. |
| 2004/0092875 A1 | 5/2004 | Kochamba |
| 2004/0111086 A1 * | 6/2004 | Trembly ................ A61B 18/14 606/27 |
| 2004/0140028 A1 | 7/2004 | Clark et al. |
| 2004/0143250 A1 | 7/2004 | Trembly |
| 2004/0186535 A1 | 9/2004 | Knowlton |
| 2004/0206365 A1 | 10/2004 | Knowlton |
| 2004/0210214 A1 * | 10/2004 | Knowlton ....................... 606/41 |
| 2004/0230260 A1 | 11/2004 | MacFarland et al. |
| 2004/0243182 A1 | 12/2004 | Cohen et al. |
| 2004/0243200 A1 | 12/2004 | Turner et al. |
| 2004/0249426 A1 | 12/2004 | Hoenig et al. |
| 2005/0010271 A1 | 1/2005 | Merchant |
| 2005/0137654 A1 | 6/2005 | Hoenig et al. |
| 2005/0215901 A1 | 9/2005 | Anderson et al. |
| 2005/0215987 A1 | 9/2005 | Slatkine |
| 2005/0251117 A1 | 11/2005 | Anderson et al. |
| 2005/0251120 A1 | 11/2005 | Anderson et al. |
| 2005/0288666 A1 | 12/2005 | Bertolero et al. |
| 2006/0020309 A1 | 1/2006 | Altshuler et al. |
| 2006/0025837 A1 | 2/2006 | Stern et al. |
| 2006/0036300 A1 | 2/2006 | Kreindel |

(56) References Cited

U.S. PATENT DOCUMENTS

| | | |
|---|---|---|
| 2006/0111744 A1 | 5/2006 | Makin et al. |
| 2006/0112698 A1 | 6/2006 | Cazzini et al. |
| 2006/0129209 A1 | 6/2006 | McDaniel |
| 2006/0151485 A1 | 7/2006 | Cronin |
| 2006/0161228 A1 | 7/2006 | Lach |
| 2006/0167498 A1 | 7/2006 | DiLorenzo |
| 2006/0184205 A1 | 8/2006 | Schuler et al. |
| 2006/0189964 A1 | 8/2006 | Anderson et al. |
| 2006/0200213 A1 | 9/2006 | McDaniel |
| 2006/0206110 A1 | 9/2006 | Knowlton et al. |
| 2006/0259102 A1 | 11/2006 | Slatkine |
| 2006/0264926 A1 | 11/2006 | Kochamba |
| 2006/0265034 A1 | 11/2006 | Aknine et al. |
| 2006/0271028 A1* | 11/2006 | Altshuler et al. ............... 606/9 |
| 2006/0276860 A1 | 12/2006 | Ferren et al. |
| 2007/0010810 A1 | 1/2007 | Kochamba |
| 2007/0010811 A1 | 1/2007 | Stern et al. |
| 2007/0016032 A1 | 1/2007 | Aknine |
| 2007/0020355 A1 | 1/2007 | Schlebusch et al. |
| 2007/0049918 A1 | 3/2007 | van der Weide et al. |
| 2007/0060989 A1 | 3/2007 | Deem et al. |
| 2007/0078290 A1 | 4/2007 | Esenaliev |
| 2007/0078502 A1 | 4/2007 | Weber et al. |
| 2007/0088413 A1 | 4/2007 | Weber et al. |
| 2007/0179482 A1 | 8/2007 | Anderson |
| 2007/0179535 A1 | 8/2007 | Morrissey et al. |
| 2007/0233226 A1 | 10/2007 | Kochamba et al. |
| 2007/0237620 A1 | 10/2007 | Mühlhoff et al. |
| 2007/0255274 A1 | 11/2007 | Stern et al. |
| 2007/0255355 A1 | 11/2007 | Altshuler et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0091183 A1 | 4/2008 | Knopp et al. |
| 2008/0119830 A1 | 5/2008 | Ramstad et al. |
| 2008/0195000 A1 | 8/2008 | Spooner et al. |
| 2008/0294152 A1 | 11/2008 | Altshuler et al. |
| 2008/0319437 A1 | 12/2008 | Turner et al. |
| 2009/0221999 A1 | 9/2009 | Shahidi |
| 2009/0299361 A1 | 12/2009 | Flyash et al. |
| 2009/0299364 A1 | 12/2009 | Batchelor et al. |
| 2010/0049178 A1 | 2/2010 | Deem et al. |
| 2010/0114086 A1 | 5/2010 | Deem et al. |
| 2010/0211059 A1 | 8/2010 | Deem et al. |
| 2010/0268220 A1 | 10/2010 | Johnson et al. |
| 2011/0028898 A1 | 2/2011 | Clark, III et al. |
| 2011/0040299 A1 | 2/2011 | Kim et al. |
| 2011/0196365 A1 | 8/2011 | Kim et al. |
| 2011/0313412 A1 | 12/2011 | Kim et al. |
| 2012/0010609 A1 | 1/2012 | Deem et al. |
| 2012/0022622 A1 | 1/2012 | Johnson et al. |
| 2012/0041432 A1 | 2/2012 | Spertell |
| 2013/0035680 A1 | 2/2013 | Ben-Haim et al. |
| 2013/0066406 A1 | 3/2013 | Spertell |
| 2013/0150844 A1 | 6/2013 | Deem et al. |
| 2013/0166003 A1 | 6/2013 | Johnson et al. |
| 2014/0005645 A1 | 1/2014 | Ben-Haim et al. |
| 2015/0148792 A1 | 5/2015 | Kim et al. |
| 2015/0351838 A1 | 12/2015 | Deem et al. |

FOREIGN PATENT DOCUMENTS

| | | |
|---|---|---|
| EP | 1346753 A2 | 9/2003 |
| JP | 61-364 A | 1/1986 |
| JP | 62-149347 | 9/1987 |
| JP | S-63177856 A | 7/1988 |
| JP | 07-503874 A | 4/1995 |
| JP | H09-239040 A | 9/1997 |
| JP | 2001-514921 A | 9/2001 |
| JP | 2006503618 | 2/2006 |
| JP | 2006-289098 | 10/2006 |
| JP | 2007191192 | 8/2007 |
| WO | WO 89/02292 | 3/1989 |
| WO | WO 92/07622 A1 | 5/1992 |
| WO | WO 96/23447 A1 | 8/1996 |
| WO | WO 96/41579 | 12/1996 |
| WO | WO 99/46005 A1 | 9/1999 |
| WO | WO 00/24463 A2 | 5/2000 |
| WO | WO 01/58361 A1 | 8/2001 |
| WO | WO 03/039385 A2 | 5/2003 |
| WO | WO 2004/034925 A2 | 4/2004 |
| WO | WO 2005/060354 A2 | 7/2005 |
| WO | WO 2005/099369 A2 | 10/2005 |
| WO | WO 2005/112807 A2 | 12/2005 |
| WO | WO 2005/120379 A2 | 12/2005 |
| WO | WO 2006/089227 A2 | 8/2006 |
| WO | WO 2006/090217 A1 | 8/2006 |
| WO | WO 2006/117682 A2 | 11/2006 |
| WO | WO 2006/122136 A2 | 11/2006 |
| WO | WO 2007/015247 A2 | 2/2007 |
| WO | WO 2007/030367 A2 | 3/2007 |
| WO | WO 2007/038567 A1 | 4/2007 |
| WO | WO 2007/050572 A2 | 5/2007 |
| WO | WO 2007/106339 A2 | 9/2007 |
| WO | WO2007/108516 A1 | 9/2007 |
| WO | WO 2007/131112 A2 | 11/2007 |
| WO | WO 2007/140469 A2 | 12/2007 |
| WO | WO 2009/072108 A2 | 6/2009 |

OTHER PUBLICATIONS

"Aesthera US—How it Works," http://www.aesthera.com/go/aestheralUS/patients/how_it_works/index.cfm, accessed Jul. 8, 2008.

Ashby et al., "Cryosurgery for Axillary Hyperhidrosis" British Medical Journal, pp. 1173-1174 (Nov. 13, 1976).

Beer et al., "Immunohistochemical Differentiation and Localization Analysis of Sweat Glands in the Adult Human Axilla," Plastic and Reconstructive Surgery, vol. 117, No. 6, pp. 2043-2049 (May 2006).

Brace et al., "Microwave Ablation with a Triaxial Antenna: Results in ex vivo Bovine Liver," IEEE Transactions on Microwave Theory and Techniques, vol. 53, No. 1, pp. 215-220 (Jan. 2005).

Christ et al., "Characterization of the Electromagnetic Near-Field Absorption in Layered Biological Tissue in the Frequency Range from 30 MHz to 6000 MHz," Phys. Med. Biol., 51, pp. 4951-4965 (2006).

Christ et al., "The Dependence of Electromagnetic Far-Field Absoprtion on Body Tissue Composition in the Frequency Range from 300 MHz to 6 GHz," IEEE Transactions on Microwave Theory and Techniques, vol. 54, No. 5, pp. 2188-2195 (May 2006).

"Cool-tip™ RF Ablation System Technology," http://www.cool-tiprf.com/physics.html accessed Jun. 24, 2008.

Copty et al., "Low-power near-field microwave applicator for localized heating of soft matter," Applied Physics Letters, vol. 84, No. 25, pp. 5109-5111 (Jun. 21, 2004).

De Bruijne et al., "Effects of waterbolus size, shape and configuration on the SAR distribution pattern of the Lucite cone applicator," Int. J. Hyperthermia, 22(1): 15-28 (Feb. 2006).

Diederich, C.J. and Stauffer, P.R., "Pre-clinical evaluation of a microwave planar array applicator for superficial hyperthermia," Int. J. Hyperthermia, vol. 9, No. 2, pp. 227-246 (1993).

Drozd, Brian and Joines, William T., "Comparison of Coaxial Dipole Antennas for Applications in the Near-Field and Far-Field Regions," MW Journal, vol. 47, No. 5 (May 2004), http://www.mwjournal.com/Journal accessed Dec. 10, 2007.

Gold, Michael H., M.D., and Goldman, Mitchel P., M.D., "Treatment of Wrinkles and Skin Tightening Using Aluma™ Skin Renewal System with FACES™ (Functional Aspiration Controlled Electrothermal Stimulation) Technology," Lumens, Inc. (Oct. 2005).

Hu, Da Zhang, "Electromagnetic Field in Organism of Skin-Fat-Muscle," China Research Institute of Radiowave Propagation IEEE (1998).

Kawoos et al., "Issues in Wireless Intracranial Pressure Monitoring at Microwave Frequencies," PIERS Online, vol. 3, No. 6, pp. 927-931 (2007).

(56) References Cited

OTHER PUBLICATIONS

Kobayashi, Toshio, M.D., "Electrosurgery Using Insulated Needles: Treatment of Axillary Bromhidrosis and Hyperhidrosis," *J Dermatol Surg Oncol*, 14:7, pp. 749-752 (Jul. 1988).
Lane et al., "Pressure-Induced Bullae and Sweat Gland Necrosis Following Chemotherapy Induction," *The American Journal of Medicine*, vol. 117, pp. 441-443 (Sep. 15, 2004).
Lawrence et al., "Selective Sweat Gland Removal with Minimal Skin Excision in the Treatment of Axillary Hyperhidrosis: A Retrospective Clinical and Histological Review of 5 Patients" *British Journal of Dermatology*, British Association of Dermatologists, 115, pp. 115-118 (2006).
Lowe et al., "Microwave delivery system for lower leg telangiectasia," *Journal of Cutaneous Laser Therapy*, 2:3-7 (2000).
Michel et al., "Design and Modeling of Microstrip—Microslot Applicators with Several Patches and Apertures for Microwave Hyperthermia," *Microwave and Optical Technology Letters*, vol. 14, No. 2, pp. 121-125 (Feb. 5, 1997).
"Microwave Ablation for Healthcare Professionals," http://www.acculis.com/mta, accessed Jun. 24, 2008.
Park et al., "A Comparative Study of the Surgical Treatment of Axillary Osmidrosis by Instrument, Manual, and Combined Subcutaneous Shaving Procedures," pp. 488-497 (1998).
Paulides et al., "A Patch Antenna Design for Application in a Phased-Array Head and Neck Hyperthermia Applicator," *IEEE Transactions on Biomedical Engineering*, vol. 54, Issue 11, pp. 2057-2063 (Nov. 2007).
Rappaport, C., "Treating Cardiac Disease with Catheter-Based Tissue Heating," *IEEE Microwave Magazine*, pp. 57-64 (Mar. 2002).
Saito et al., "Clinical Trials of Interstitial Microwave Hyperthermia by Use of Coaxial-Slot Antenna with Two Slots," *IEEE Transactions on Microwave Theory and Techniques*, vol. 52, No. 8, pp. 1987-1991 (Aug. 2004).
Sherar et al., "Helical antenna arrays for interstitial microwave thermal therapy for prostate cancer; tissue phantom testing and simulations for treatment," *Phys. Med. Biol.*, 46, pp. 1905-1918 (2001).
Stauffer, Paul R., "Evolving technology for thermal therapy of cancer," *Int. J. Hyperthermia*, 21(8): 731-744 (Dec. 2005).
Stauffer, Paul R., "Thermal Therapy Techniques for Skin and Superficial Tissue Disease," *Critical Reviews*, vol. CR75, pp. 327-367 (2000).
Sterzer, Fred., "Microwave Medical Devices," *IEEE Microwave Magazine*, pp. 65-70 (Mar. 2002).
"Study Published in Facial Plastic Surgery Journal Finds Selective Heating of Fibrous Septae Key to Success and Safety of Thermage® ThermaCool™ System," www.thermage.com.
Trembly, B. Stuart, and Keates, Richard H., "Combined Microwave Heating and Surface Cooling of the Cornea," *IEEE Transactions on Biomedical Engineering*, vol. 38, No. 1 (Jan. 1991).
Uzunoglu et al., "A 432-MHz Local Hyperthermia System Using an Indirectly Cooled, Water-Loaded Waveguide Applicator," *IEEE Transactions on Microwave Theory and Techniques*, vol. TT-35, No. 2 pp. 106-111.
Van Rhoon et al., "A 433 MHz Lucite Cone Waveguide Applicator for Superficial Hyperthermia," Int. J. Hyperthermia, vol. 14, No. 1 pp. 13-27, 1998.
Vrba, et al., "Evanescent-Mode Applicators (EMA) for Superficial and Subcutaneous Hyperthermia," *IEEE Transactions on Biomedical Engineering*, vol. 40, No. 5, pp. 397-407 (May 1993).
Yang et al., "A Floating Sleeve Antenna Yields Localized Hepatic Microwave Ablation," *IEEE Transactions on Biomedical Engineering*, vol. 53, No. 3, pp. 533-537 (Mar. 2006).
PCT International Search Report for PCT/US2008/060929.
PCT International Search Report for PCT/US2008/60940, mailed Aug. 27, 2008.
PCT International Search Report for PCT/US2008/60935, mailed Sep. 3, 2008.
PCT International Search Report for PCT/US2008/60922, mailed Sep. 4, 2008.
Abraham et al.; Monopolar radiofrequency skin tightening; Facial Plast Surg Clin N Am; 15(2); pp. 169-177; May 2007.
Alster et al.; Improvement of neck and cheek laxity with a non-ablative radiofrequency device: a lifting experience; Dermatol Surg; 30(4); pp. 503-507; Apr. 2004.
Atkins et al.; Hyperhidrosis: A Review of Current Management; Plast Reconstr Surg; 110(1); pp. 222-228; Jul. 2002.
Ball, P.; Radio sweat gland—90 GHz; Nature; 452(7188); p. 676; Apr. 10, 2008; printed Jun. 18, 2012 from website (http://www.nature.com/news/2008/080409/full/452676a.html).
Bindu et al.; Microwave characterization of breast-phantom materials; Microwave and Optical Tech. Letters; 43(6); pp. 506-508; Dec. 20, 2004.
Bioportfolio; Tenex Health Receives FDA clearance for innovative TX1} tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).
Burns, Jay A.; Thermage: monopolar radiofrequency; Aesthetic Surg J; 25(6); pp. 638-642; Nov./Dec. 2005.
Campbell et al.; Dielectric properties of female human breast tissue measured in vitro at 3.2 GHz; Phys. Med. Biol.; 37(1); pp. 193-210; Jan. 1992.
Candela Corp.; The Candela SeleroPLUS Laser with Dynamic Cooling Device: The Benefits of Anesthesia without the Risks; Nov. 1998.
Chang et al.; A conductive plastic for simulating biological tissue at microwave frequencies; IEEE Trans on Electromagnetic Compatibility; 42(1); pp. 76-81; Feb. 2000.
CK Electronic GmbH; Scientific Measurements of Skin and Hair (product information); 15 pgs.; published after Sep. 2006.
Eleiwa et al.; Accurate FDTD simulation of biological tissues for bio-electromagnetic applications; IEEE Proc. SoutheastCon 2001; Clemson, SC; Mar. 30-Apr. 1, 2001; pp. 174-178.
Farace et al.; An automated method for mapping human tissue permittivities by MRI in hyperthermia treatment planning; Phys. Med. Biol.; 42(11); pp. 2159-2174; Nov. 1997.
Fitzpatrick et al.; Multicenter study of noninvasive radiofrequency for periorbital tissue tightening; Lasers Surg Med; 33(4); pp. 232-242; Mar. 2003.
Gabriel et al.; Dielectric parameters relevant to microwave dielectric heating; Chem Soc Rev; 27(3); pp. 213R224; May-Jun. 1998.
Gabriel et al.; The dielectric properties of biological tissues: I. Literature survey; Phys Med Biol; 41(11); pp. 2231R2249; Nov. 1996.
Gabriel et al.; The dielectric properties of biological tissues: II. Measurements in the frequency range 10 Hz to 20 GHz; Phys Med Biol; 41(11); pp. 2251R2269; Nov. 1996.
Gabriel et al.; The dielectric properties of biological tissues: III. Parametric models for the dielectric spectrum of tissues; Phys Med Biol; 41(11); pp. 2271R2293; Nov. 1996.
Gabriel, et al.; Comparison of the Dielectric Properties of Normal and Wounded Human Skin Material; Bioelectromagnetics; 8; pp. 23-27; Jan. 1987.
Gandhi et al.; Electromagnetic Absorption in the Human Head and Neck for Mobile Telephones at 835 and 1900 MHz; IEEE Transactions on Microwave Theory and Techniques; 44(10); pp. 1884R1897; Oct. 1996.
Garber, B. B.; Office microwave treatment of enlarged prostate symptoms; 2 pgs.; printed from website (http://www.garber-online.com/microwave-treatment.htm) on Jun. 18, 2012.
Guidant Corp.; Guidant microwave surgical ablation system; 1 pg.; © 2004; printed Jun. 18, 2012 from website (http://web.archive.org/web/20070306031424/http://www.ctsnet.org/file/vendors/872/pdf/MicrowaveAblationIFU.pdf).
Guy, Arthur; History of Biological Effects and Medical Applications of Microwave Energy; IEEE Transactions on Microwave Theory and Techniques; 32(9); pp. 1182-1200; Sep. 1984.

(56) References Cited

OTHER PUBLICATIONS

Guy, Arthur; Therapeutic Heat and Cold, Fourth Ed.; Chapter 5: Biophysics of High-Frequency Currents and Electromagnetic Radiation; pp. 179R236. Williams and Wilkins (publishers); Apr. 1990.

Guy; Analyses of electromagnetic fields induced in biological tissues by thermographic studies on equivalent phantom models; IEEE Trans on Microwave Theory and Techniques; MTT-19(2); pp. 205-214; Feb. 1971.

Hey-Shipton, et al.; The Complex Permittivity of Human Tissue at Microwave Frequencies; Phys. Med. Biol.; 27(8); pp. 1067-1071; Aug. 1982.

Hisada et al.; Hereditary Hemorrhagic Telangiectasia Showing Severe Anemia which was successfully treated with estrogen; International Medicine; vol. 34; No. 6; pp. 589-592; Jun. 1995.

Jacobsen et al.; Characteristics of microstrip muscle-loaded single-arm archimedean spiral antennas as investigated by FDTD numerical computations; IEEE Trans. On Biomedical Engineering; 52(2); pp. 321-330; Feb. 2005.

Jacobsen et al.; Characterization of a tranceiving antenna concept for microwave heating and thermometry of superficial tumors; PIER; vol. 18; pp. 105-125; (month unavailable) 1998.

Jacobsen et al.; Dual-mode antenna design for microwave heating and noninvasive thermometry of superficial tissue disease; IEEE Trans. On Biomedical Engineering; 47(11); pp. 1500-1509; Nov. 2000.

Jacobsen et al.; Multifrequency radiometric determination of temperature profiles in a lossy homogeneous phantom using a dual-mode antenna with integral water bolus; IEEE Trans. on Microwave Theory and Techniques; 50(7); pp. 1737-1746; Jul. 2002.

Jacobsen et al.; Nonparametric 1-D temperature restoration in lossy media using tikhonov regularization on sparse radiometry data; IEEE Trans. on Biomedical Engineering; 50(2); pp. 178-188; Feb. 2003.

Jacobsen et al.; Transceiving antenna for homogenious heating and radiometric thermometry during hyperthermia; Electronic Letters; 36(6); pp. 496-497; Mar. 16, 2000.

Johnson et al.; Automatic temperature controller for multielement array hyperthermia systems; IEEE Trans. on Biomedical Engineering; 53(6); pp. 1006-1015; Jun. 2006.

Johnson et al.; Evaluation of a dual-arm Archimedean spiral array for microwave hyperthermia; Int J Hyperthermia; 22(6); pp. 475R490; Sep. 2006.

Juang et al.; Construction of a conformal water bolus vest applicator for hyperthermia treatment of superficial skin cancer; Proc. of the 26th Ann. Int. Conf. of the IEEE EMBS; San Francisco, CA, USA; Sep. 1-5, 2004; pp. 3467-3470.

Kirn, T. F.; Researchers seek to quantify thermage efficacy; Dermatologic Surgery; p. 36; Jan. 2007.

Kirsch et al.; Ultrastructure of collagen thermally denatured by microsecond domain pulsed carbon dioxide laser; Arch Dermatol; 134; pp. 1255-1259; Oct. 1998.

Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.

Kumaradas et al.; Optimization of a beam shaping bolus for superficial microwave hyperthermia waveguide applicators using a finite element method; Phys. Med. Biol.; 48(1); pp. 1-18; Jan. 7, 2003.

Lagendijk et al; Hyperthermia dough: a fat and bone equivalent phantom to test microwave/radiofrequency hyperthermia heating systems; Phys. Med. Biol.; 30(7); pp. 709-712; Jul. 1985.

Land et al.; A quick accurate method for measuring the microwave dielectric properties of small tissue samples; Phys. Med. Biol.; 37(1); pp. 183-192; Jan. 1992.

Larson et al.; Microwave treatments for enlared prostate cause blood pressure surges, study shows; 2 pgs.; Apr. 11, 2008; printed on Jun. 18, 2012 from website (http://web.archive.org/web/20080415000815/http://www.sciencedaily.com/releases/2008/04/080408105820.htm).

Lehmann et al.; Therapeutic Heat; Therapeutic Heat and Cold, Fourth Ed.; Chapter 9; pp. 417-581; Williams & Wilkins (publishers), Baltimore, MD; Apr. 1990.

Lumenis Inc.; Aluma RF Skin Renewal System (product information); copyright 2007 (PB-1013670); 8 pgs.; Oct. 2007 (printed version).

Maccarini et al.; Advances in microwave hyperthermia of large superficial tumors; Microwave Symposium Digest, IEEE MTT-S International; pp. 1797-1800; Jun. 2005.

Maccarini et al.; Electromagnetic optimization of dual mode antennas for radiometry controlled heating of superficial tissue; Proceedings of SPIE; vol. 5698; Bellingham, WA; pp. 71-81; Jan. 2005.

Maccarini et al.; Optimization of a dual concentric conductor antenna for superficial hyperthermia applications; Proc. of the 26th Ann. Int. Conf. of the IEEE EMBS; San Francisco, CA, USA; Sep. 1-5, 2004; pp. 2518-2521.

Mazzurana et al.; A semi-automatic method for developing an anthropomorphic numerical model of dielectric anatomy by MRI; Phys. Med. Biol.; 48(19); pp. 3157-3170; Oct. 7, 2003.

Mrozowski et al.; Parameterization of media dispersive properties for FDTD; IEEE Trans on Antennas and Propagation; 45(9); pp. 1438-1439; Sep. 1997.

Nagaoka et al.; Development of realistic high-resolution whole-body voxel models of Japanese adult males and females of average height and weight, and application of models to radio-frequency electromagnetic-field dosimetry; Phys. Med. Biol.; 49(1); pp. 1-15; Jan. 7, 2004.

Neuman; SAR pattern perturbations from resonance effects in water bolus layers used with superficial microwave hyperthermia applicators; Int. J. Hyperthermia; 18(3); pp. 180-193; May-Jun. 2002.

Popovic et al.; Dielectric spectroscopy of breast tissue—improved model of the precision open-ended coaxial probe; Proc of the 25th Ann Int Conf of the IEEE EMBS; Cancun, Mexico; pp. 3791-3793; Sep. 17-21, 2003.

Popovic et al.; Response characterization of the precision open-ended coaxial probe for dielectric spectroscopy of breast tissue; 2003 IEEE—Anntennas and Propagation Soc. Int. Symp.; vol. 4; pp. 54-57; Jun. 22-27, 2003.

Pozar, David M.; Electromagnetic Theory (Introduction); Microwave Engineering, Second Edition; John Wiley & Sons, Inc.; p. 1; Aug. 1997.

Rolfsnes et al.; Design of spiral antennas for radiometric temperature measurement; Proc. of the 26th Ann. Int. Conf. of the IEEE EMBS; San Francisco, CA, USA; Sep. 1-5, 2004; pp. 2522-2525.

Rosen et al.; Microwaves treat heart disease; IEEE Microw Mag; 8(1); pp. 70R75; Feb. 2007.

Ross et al.; A pilot study of in vivo immediate tissue contraction with CO2 skin laser resurfacing in a live farm pig; Dermatol Surg; 25(11); pp. 851R856; Nov. 1999.

Ross et al.; Comparison of carbon dioxide laser, erbium: Yag laser, dermabrasion, and dermatome a study of thermal damage, wound contraction, and woundhealing in a live pig model: Implications for skin. resurfacing; J Am Acad Dermatol; 42(1); pp. 92R105; Jan. 2000.

Ross et al.; Use of a novel erbium laser in a yucatan minipig: A study of residual thermal damage, ablation, and wound healing as a function of pulse duration; Lasers Surg Med; 30(2); pp. 93R100; Feb. 2002.

Rossetto et al.; Effect of complex bolus-tissue load configurations on SAR distributions from dual concentric conductor applicators; IEEE Trans. on Biomedical Engineering; 46(11); pp. 1310-1319; Nov. 1999.

Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.

Sipahioglu et al.; Dielectric properties of vegetables and fruits as a function of temperature, ash, and moisture content; Journal of Food Science; 68(1); pp. 234-239; Jan. 2003.

(56) References Cited

OTHER PUBLICATIONS

Sirowiec et al.; Dielectric properties of breast carcinoma ind the surrounding tissues; IEEE Trans on Biomedical Engineering; 35(4); pp. 257-263; Apr. 1988.
Spertell et al.; Review of clinical data on hair removal using the MW 2000 microwave delivery system (promotional material); 2000; MW Medical, Inc.; printed from http://www.hairfacts.com/medpubs/mwave/spertell.html on Jun. 23, 2009; 5 pgs.
Spertell; Presentation at the American Academy of Dermatology; MW Medical, Inc.; Mar. 10, 2000; 21 pgs.
Spertell; The application of microwaves to the treatment of cosmetic skin conditions: a technical summary; MW Medical, Inc.; pp. 1-15; May 25, 1999.
SRLI Technologies; BTC-2000} (product information); printed from website: http://www.srli.com/technologies/BTC2000.html on Nov. 16, 2009; 1 pg.
Stauffer et al.; Combination applicator for simultaneous heat and radiation; Proc. of the 26th Ann. Int. Conf. of the IEEE EMBS; San Francisco, CA, USA; Sep. 1-5, 2004; pp. 2514-2517.
Stauffer et al.; Dual mode antenna array for microwave heating and non-invasive thermometry of superficial tissue disease; SPIE Conf. on Thermal Treatment of Tissue with Image Guidance; San Jose, CA; SPIE; vol. 3594; pp. 139-147; Jan. 1999.
Stauffer et al.; Microwave array applicator for rediometry controlled superficial hyperthermia; Proc. of the SPIE; vol. 4247; pp. 19-29; Jun. 2001.
Stauffer et al.; Phantom and animal tissues for modelling the electrical properties of human liver; Int. J. Hyperthermia; 19(1); pp. 89-101; Jan.-Feb. 2003.
Stauffer et al.; Practical induction heating coil designs for clinical hyperthermia with ferromagnetic implants; IEEE Trans. on Biomedical Engineering; 41(1); pp. 17-28; Jan. 1994.
Stauffer et al.; Progress on system for applying simultaneous heat and brachytherapy to large-area surface disease; Proceedings of SPIE; vol. 5698; Bellingham, WA; pp. 82-96; Jan. 2005.
Stauffer et al.; Progress toward radiometry controlled conformal microwave array hyperthermia applicator; Proc. of the 22nd Ann. EMBS Int. Conf.; Chicago, IL; Jul. 23-28, 2000; pp. 1613-1616.
Stoy et al.; Dielectric properties of mammalian tissues from 0.1 to 100 MHz: a summary of recent data; Phys. Med. Bil.; 27(4); pp. 501-513; Apr. 1982.
Strutton et al.; US prevalence of hyperhidrosis and impact on individuals with axillary hyperhidrosis: Results from a national survey. J Am Acad Dermatol; 51(2); pp. 241R248; Feb. 2004.
Stuchly et al.; Diathermy applicators with circular aperture and corrugated flange; IEEE Trans on Microwave Theory and Techniques; MTT-28(3); pp. 267-271; Mar. 1980.
Stuchly et al.; Dielectric properties of animal tissues in vivo at frequencies 10 MHz-1 GHz; Bioelectromagnetics; 2(2); pp. 93-103; Apr. 1981.
Stuchly et al.; Dielectric properties of animal tissues in vivo at radio and microwave frequencies: comparison between species; Phys. Med. Biol.; 27(7); pp. 927-936; Jul. 1982.
Sullivan et al.; Comparison of measured and simulated data in an annular phased array using an inhomogeneous phantom; IEEE Trans on Microwave Theory and Techniques; 40(3); pp. 600-604; Mar. 1992.
Sullivan et al.; The pig as a model for human wound healing; Wound Repair Regen; 9(2); pp. 66R76; Mar. 2001.
Sunaga et al.; Development of a dielectric equivalent gel for better impedance matching for human skin; Bioelectromagnetics; 24; pp. 214-217; Apr. 2003.
Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.
Thermolase Corp.; 510K Pre-Market Notification (No. K950019) and Product User Manual ThermoLase Model LT100 Q-Switched Nd: YAG, Laser Hair Removal System, Jan. 3, 1995.

Urolgix, Inc.; Cooled Thermotherapy + Prostiva RF = Durability + Versatility; 1 pg.; printed Jun. 18, 2012 from website (http://www.urologix.com/).
Vander Vorst et al.; RF/microwave interaction with biological tissues; Hoboken, NJ; John Wiley & Sons, Inc.; pp. 264-305; Jan. 2006.
Vardaxis et al.; Confocal laser scanning microscopy of porcine skin: Implications for human wound healing studies; J Anat; 190(04); pp. 601R611; May 1997.
Weiss et al.; Monopolar radiofrequency facial tightening: a retrospective analysis of efficacy and safety in over 600 treatments; J Drugs Dermatol; 5(8); pp. 707-712; Sep. 2006.
Wonnell et al.; Evaluation of microwave and radio frequency catheter ablation in a myocardium-equivalent phantom model; IEEE Trans. on Biomedical engineering; 39(10); pp. 1086-1095; Oct. 1992.
Zelickson et al.; Histological and ultrastructural evaluation of the effects of a radiofrequency-based nonablative dermal remodeling device; Arch Dermatol; 140; pp. 204-209; Feb. 2004.
Zelickson et al.; Ultrastructural effects of an infrared handpiece on forehead and abdominal skin; Dermatol Surg; 32(7); pp. 897-901; Jul. 2006.
Zhou et al.; Resection of Meningiomas with Implantable Microwave Coagualation; Bioelectromagnetics; vol. 17; No. 2; pp. 85-88; (month unavailable) 1996.
Allergan Pharmaceuticals; Botox® (product insert); 16 pgs.; Oct. 2006.
Arneja et al.; Axillary hyperhidrosis: a 5-year review of treatment efficacy and recurrence rates using a new arthroscopic shaver technique; Plast. Reconstr. Surg.; vol. 119; pp. 562-567; Feb. 2007.
Bentel et al.; Variability of the depth of supraclavicular and axillary lymph nodes in patients with breast cancer: is a posterior axillary boost field necessary?; Int J Radiation Oncology Biol Phys; vol. 47(3); pp. 755-758; Jun. 2000.
Blanchard et al.; Relapse and morbidity in patients undergoing sentinel lymph node biopsy alone or with axillary dissection for breast cancer; Arch Surg; vol. 138; pp. 482-488; May 2003.
Cobham; Antenna & Radome Design Aids (product list); 1 pg.; Aug. 2001.
Duparc et al.; Anatomical basis of the variable aspects of injuries of the axillary nerve (excluding the terminal branches in the deltoid muscle); Surg Radiol Anat; vol. 19(3); pp. 127-132; May 1997.
Galloway et al.; Ultrasound imaging of the axillary vein—anatomical basis for central venous access; British ournal of Anaesthesia; 90(5); pp. 589-595; May 2003.
Haedersdal et al.; Evidence-based review of hair removal using lasers and light sources; JEADV; vol. 20; pp. 9-20; Jan. 2006.
Hornberger et al.; Recognition, diagnosis, and treatment of primary focal hyperhidrosis; J Am Acad Dermatol; vol. 51; pp. 274-286; Aug. 2004.
Lowe et al.; Botulinum toxin type A in the treatment of primary axillary hyperhidrosis: A 52-week multicenter double-blind, randomized, placebo-controlled study of efficacy and safety; J Am Acad Dermatol; vol. 56; pp. 604-611; Apr. 2007.
Riddle et al.; Complex permittivity measurements of common plastics over variable temperatures; IEEE Trans on Microwave Theory and Techniques; vol. 51(3); pp. 727-733; Mar. 2003.
Solish et al.; A comprehensive approach to the recognition, diagnosis, and severity-based treatment of focal hyperhidrosis: recommendations of the Canadian hyperhidrosis advisory committee; Dermatol Surg; vol. 33; pp. 908-923; Aug. 2007.
Solish et al.; Prospective open-label study of botulinum toxin type A in patients with axillary hyperhodrosis: effects on functional impairment and quality of life; Dermatol Surg; vol. 31(4); pp. 405-413; Apr. 2005.
Houzen et al.; Implanted antenna for an artificial cardiac pacemaker system; Progress in Electromagnetics Research Symposium 2007; Prague, CZ; pp. 51-54; Aug. 27-30, 2007.
Kim et al.; Implanted antennas inside a human body: Simulations, designs, and characterizations; IEEE Trans on Microwave Theory and Techniques; 52(8); pp. 1934-1943; Aug. 2004.

(56) References Cited

OTHER PUBLICATIONS

Soontornpipit et al.; Design of implantable microstrip antenna for communication with medical implants; IEEE Trans on Microwave Theory and Techniques; 52(8); pp. 1944-1951; Aug. 2004.

Virga et al.; Low-profile enhanced-bandwidth PIFA antennas for wireless communications packaging; IEEE Trans on Microwave Theory and Techniques; 45(10); pp. 1879-1888; Oct. 1997.

Johnson et al.; U.S. Appl. No. 14/194,503 entitled "Systems, apparatus, methods and procedures for the non-invasive treatment of tissue using microwave energy," filed Feb. 28, 2014.

Ben-Haim et al.; U.S. Appl. No. 13/677,633 entitled "Applicator and Tissue Interface Module for Dermatological Device," filed Nov. 15, 2012.

Ben-Haim et al.; U.S. Appl. No. 13/677,648 entitled "Applicator and Tissue Interface Module for Dermatological Device," filed Nov. 15, 2012.

Wikipedia; Bayonet mount; 6 pages; Dec. 18, 2014; retrieved from the internet (www.http://en.wikipedia.org/wiki/Bayonet mount).

Wright et al.; Hepatic microwave ablation with multiple antennae results in synergistically larger zones of coagulation necrosis; Ann. Surg. Oncol.; 10(3); pp. 275-283; Apr. 2003.

Gabriel; Compilation of the dielectric properties of body tissues at RF and microwave frequencies (Technical Report); Armstrong Laboratory; Doc. No. AL/OE-TR-1996-004; pp. 1-16; Jan. 1996.

Gandhi et al.; Electromagnetic Absorption in the Human Head from Experimental 6-GHz Handheld Transceivers; IEEE Trans. On Electromagnetic Compatibility; 37(4); pp. 547-558; Nov. 1995.

Klemm et al.; EM energy absorption in the human body tissues due to UWB antennas; Progress in Electromagnetics Research; PIER; 62; pp. 261-280; 2006 (year of pub. sufficiently earlier than effective US filed and any foreign priority date).

Wikipedia; ISM band; 5 pages; printed Jul. 22, 2014 from website (http://en.wikipedia.org/wiki/ISM_band).

Spertell; U.S. Appl. No. 14/471,833 entitled "Method and apparatus for treating subcutaneous histological features," filed Aug. 28, 2014.

Chun et al.; U.S. Appl. No. 14/829,434 entitled "Apparatus, system and method for treating fat tissue," filed Aug. 18, 2015.

* cited by examiner

SYSTEMS AND METHODS FOR CREATING AN EFFECT USING MICROWAVE ENERGY TO SPECIFIED TISSUE

The present application claims priority under 35 U.S.C. §119(e) to U.S. Provisional Application No. 60/912,899 filed Apr. 19, 2007 and entitled METHODS AND APPARATUS FOR REDUCING SWEAT PRODUCTION; U.S. Provisional Application No. 61/013,274 filed Dec. 12, 2007 and entitled METHODS, DEVICES AND SYSTEMS FOR NON-INVASIVE DELIVERY OF MICROWAVE THERAPY; and U.S. Provisional Application No. 61/045,937 filed Apr. 17, 2008 and entitled SYSTEMS AND METHODS FOR CREATING AN EFFECT USING MICROWAVE ENERGY IN SPECIFIED TISSUE. All of the above priority applications are expressly incorporated by reference in their entirety. This application also claims priority under 35 U.S.C. §120 as a continuation-in-part application of each of the following PCT applications: PCT Application Serial. No. PCT/US08/60935, entitled METHODS AND APPARATUS FOR SWEAT PRODUCTION, filed Apr. 18, 2008; PCT Application Serial No. PCT/US08/60929, entitled METHODS, DEVICES, AND SYSTEMS FOR NON-INVASIVE DELIVERY OF MICROWAVE THERAPY, filed Apr. 18, 2008; PCT Application Serial No. PCT/US08/60940, entitled SYSTEMS AND METHODS FOR CREATING AN EFFECT USING MICROWAVE ENERGY TO SPECIFIED TISSUE filed Apr. 18, 2008; and PCT Application Serial No. PCT/US08/60922, entitled SYSTEMS AND METHODS FOR CREATING AN EFFECT USING MICROWAVE ENERGY TO SPECIFIED TISSUE, filed Apr. 18, 2008. All of the above PCT priority applications are also expressly incorporated by reference in their entirety.

BACKGROUND

1. Field of the Invention

The present application relates to methods, apparatuses and systems for non-invasive delivery of microwave therapy. In particular, the present application relates to methods, apparatuses and systems for non-invasively delivering microwave energy to the epidermal, dermal and sub-dermal tissue of a patient to achieve various therapeutic and/or aesthetic results.

2. Description of the Related Art

It is known that energy-based therapies can be applied to tissue throughout the body to achieve numerous therapeutic and/or aesthetic results. There remains a continual need to improve on the effectiveness of these energy-based therapies and provide enhanced therapeutic results with minimal adverse side effects or discomfort.

DESCRIPTION OF EMBODIMENTS OF THE INVENTION

Figure 1:
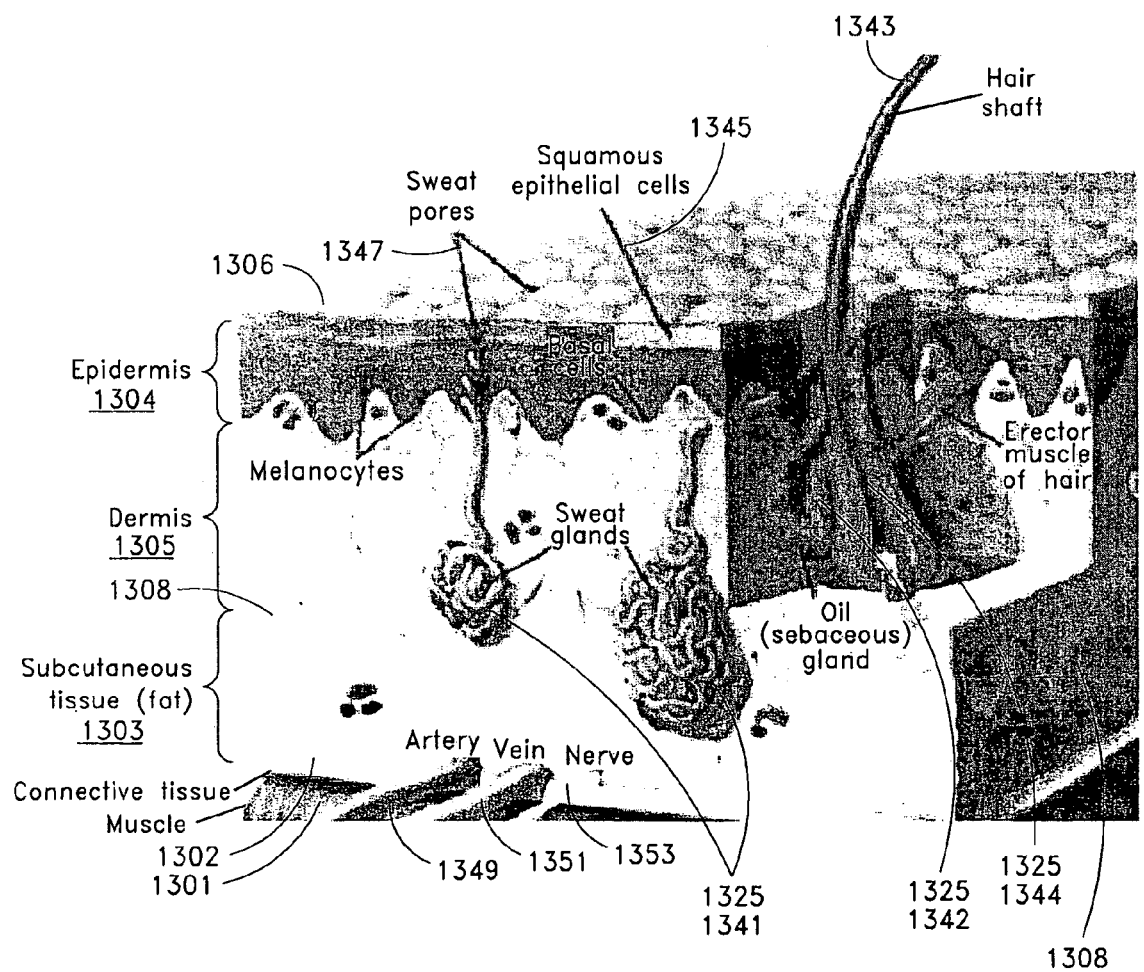
FIG. 1 is an illustration of a cross-section of human tissue structures.

When skin is irradiated with electromagnetic radiation, such as, for example, microwave energy, energy is absorbed by each layer of tissue as the electromagnetic radiation passes through the tissue. The amount of energy absorbed by each tissue layer is a function of a number of variables. Some of the variables which control the amount of energy absorbed in each tissue layer include: the power of the electromagnetic radiation which reaches each layer; the amount of time each layer is irradiated; the electrical conductivity or loss tangent of the tissue in each layer and the radiation pattern of the antenna radiating the electromagnetic energy. The power which reaches a particular layer of tissue is a function of a number of variables. Some of the variables which control the power reaching a particular layer of tissue include the power impinging upon the surface of the skin and the frequency of the electromagnetic radiation. For example, at higher frequencies the penetration depth of the electromagnetic signal is shallow and most power is deposited in the upper layers of tissue, at lower frequencies, larger penetration depths result in power deposition in both upper and lower tissue layers.

Heat may be generated in tissue by a number of mechanisms. Some of the mechanisms for generating heat in tissue include resistive heating, dielectric heating and thermal conduction. Resistive heating occurs when electrical currents are generated in the tissue, resulting in resistive losses. Tissue may be resistively heated using, for example, monopolar or bi-polar RF energy. Dielectric heating occurs when electromagnetic energy induces an increased physical rotation of polar molecules that converts microwave energy into heat. Tissue may be dielectrically heated by, for example, irradiating the tissue with electromagnetic energy in the microwave frequency band. As used herein, microwave frequency band or microwave frequencies may refer to, for example, electromagnetic energy at frequencies which are suitable for inducing dielectric heating in tissue when that tissue is irradiated using an external antenna to transmit the electromagnetic radiation. Such frequencies may be in the range of, for example, from approximately 100 Megahertz (MHz) to 30 Gigahertz (GHz). Whether tissue is heated by resistive heating or by dielectric heating, heat generated in one region of tissue may be transmitted to adjacent tissue by, for example, thermal conduction, thermal radiation or thermal convection.

When a microwave signal is radiated into a lossy dielectric material such as water, the energy of the signal is absorbed and converted to heat as it penetrates the material. This heat is primarily generated by induced physical rotation of molecules when subjected to the microwave signal. The efficiency of the conversion of microwave energy into heat for a given material can be quantified by the energy dissipation factor, or loss-tangent (tan δ). The loss-tangent varies as a function of material composition and the frequency of the microwave signal. Water has a large loss-tangent and heats efficiently when irradiated with microwave energy. Since all biological tissue has some water content, and thus is lossy, it can be heated using microwave energy. Different tissue types have varying amounts of water content, with muscle and skin having a relatively high water content and fat and bone having significantly less water content. Microwave heating is generally more efficient in high water content tissues.

The application of RF energy, which is conducted through the surface of the skin, or microwave energy, which is radiated through the surface of the skin, to heat tissue below the skin surface generally results in a temperature gradient having a peak at the surface of the skin and decreasing with increasing depth into the tissue. That is, the hottest point is generally found at or near the surface of the skin. The temperature gradient results from the power lost by the electromagnetic radiation as it moves through the tissue. The power loss density profile generally peaks in tissue at the skin surface and declines as the electromagnetic radiation moves through the tissue, regardless of the radiated power or frequency of the electromagnetic radiation. Power loss density is measured in watts per cubic meter. An equivalent characterization of power deposition in tissue is the Specific Absorption Rate (SAR) which is measured in watts per kilogram. Specific absorption rate in tissue may be, for example, proportional to the square of the magnitude of electric field in that tissue. For a fixed radiated power level the penetration depth will generally decrease as the frequency increases. Thus, as a general principal, to heat tissue near the skin surface, such as, for example, the epidermis, without damage to deeper tissue layers one would generally select a higher frequency. Further, as a general principal, to heat tissue deep within the skin, such as, for example, in the deep dermis or the hypodermis, or below the skin surface, such as, for example, in muscle tissue, one would generally select a lower frequency to ensure that sufficient energy reached the deeper tissue.

Where electromagnetic energy is being used to heat structures in tissue below the skin surface and it is desirable to limit or prevent damage to the skin surface or tissue adjacent the skin surface, it is possible to modify the temperature gradient to move the peak temperature deeper into the tissue. Temperature gradients within tissue may be modified to move the peak temperature into tissue below the skin surface by, for example, using external mechanisms to remove heat from tissue close to the skin surface. External mechanisms which remove heat from the surface of the skin may include, for example, heat sinks which cool the skin surface and adjacent layers. When external mechanisms are used to remove heat from the surface of the skin, the heat may be removed as the electromagnetic radiation deposits energy into that tissue. Thus, where external mechanisms are used to remove heat from the surface of the skin and adjoining layers, energy is still absorbed at substantially the same rate by tissue adjacent the skin surface (and the power loss density and SAR in the cooled tissue remain substantially constant and are not effected by cooling) but damage is prevented by removing heat faster than it can build up, preventing the temperature of the cooled tissue, for example, tissue adjacent the skin surface, from reaching a temperature where tissue damage occurs or a lesion could form.

FIG. 1 is an illustration of human tissue structure. In the embodiment of the invention illustrated in FIG. 1, muscle tissue 1301 is connected to hypodermis 1303 by connective tissue 1302. Hypodermis 1303 is connected to dermis 1305 at interface 1308. Epidermis 1304 lies over dermis 1305. Skin surface 1306 lies over epidermis 1304 and includes squamous epithelial cells 1345 and sweat pores 1347. Tissue structures 1325 such as, for example, sweat glands 1341, sebaceous glands 1342 and hair follicles 1344, may be positioned throughout dermis 1305 and hypodermis 1303. Further, tissue structures 1325 may be positioned such that they cross or interrupt interface 1308. FIG. 1 further includes artery 1349, vein 1351 and nerve 1353. Hair follicle 1344 is attached to hair shaft 1343. Tissue structures such as, for example, apocrine glands, eccrine glands or hair follicles may be expected to have sizes in the range of, for example, between approximately 0.1 millimeter and two millimeters and may group together to form groups or structures having even larger sizes. As illustrated in FIG. 1, interface 1308 may be expected to be a non-linear, non-continuous, rough interface which may also include many tissue structures and groups of tissue structures which cross and interrupt interface 1308. When modeling tissue layers such as, for example the dermis, it is difficult to accurately model the permittivity (e.g. dielectric constants) and/or conductivity characteristics of the tissue layers because of the variability from person to person and within body regions of individuals. In addition, the presence of tissue structures and of groups of tissue structures creates additional complexities. Assuming an average dielectric constant for a particular layer does not generally reflect the complexity of the actual tissue, however, it may be used as a starting point. For example, assuming a dielectric constant of, for example, approximately 66 for dermal tissue at 100 MHz, electromagnetic energy at the low end of the microwave range, would have a wavelength of approximately 370 millimeters. Assuming a dielectric constant of, for example, approximately 38 for dermal tissue at 6.0 GHz, electromagnetic energy would have a wavelength of approximately 8 millimeters in dermal tissue. Assuming a dielectric constant of, for example, approximately 18 for dermal tissue at 30 GHz, electromagnetic energy at the high end of the microwave range would have a wavelength of approximately 2.5 millimeters in dermal tissue. Thus, as frequency increases, the presence of rough, discontinuous interfaces between tissue regions and the presence of tissue structures and groups of tissue structures will result in unpredictable scattering of at least some of the signal when it encounters tissue structures, groups of tissue structures or discontinuous tissue interfaces. For a fixed size tissue structure, group of structures or discontinuity, scattering generally increases as wavelength decreases and becomes more pronounced when wavelength is within an order of magnitude of the size of tissue structures, groups of tissue structures or discontinuities in the interface. At low frequencies, the wavelength of the signal is long enough that it would reflect off the interface without substantial unpredictable scattering.

When electromagnetic energy is transmitted through a medium having structures and interfaces, including interfaces between tissue layers, the electromagnetic energy will, depending upon the electrical and physical characteristics of the structures, groups of structures and interfaces, and the differences between electrical and physical characteristics of such structures, groups of structures and interfaces and surrounding tissue, be scattered and/or reflected by the structures, groups of structures and/or interfaces. When reflected electromagnetic waves interact with incident electromagnetic waves they may, under certain circumstances, combine to form a standing wave having one or more constructive interference peaks, such as, for example an E-field peak, and one or more interference minimums (also referred to as regions of destructive interference). However, scattering will tend to minimize or destroy such constructive interference peaks.

In modeling tissue for the purposes of the present discussion dermal tissue may be modeled to include a dermis and an epidermis. In modeling tissue for the purposes of the present discussion dermal tissue may be modeled to have a conductivity of approximately 4.5 siemens per meter at approximately 6 GHz. In modeling tissue for the purposes of the present discussion dermal tissue may be modeled to have a dielectric constant of approximately 40 at approximately 6 GHz. In modeling tissue for the purposes of the present discussion hypodermal tissue may be modeled to have a conductivity of approximately 0.3 siemens per meter at approximately 6 GHz. In modeling tissue for the purposes of the present discussion hypodermal tissue may be modeled to have a dielectric constant of approximately 5 at approximately 6 GHz.

Systems and Apparatuses

FIGS. 2 through 25 and 48 through 51 illustrate embodiments and components of embodiments of systems according to the invention which may be used to generate heat in selected tissue regions. FIGS. 2 through 25 and 48 through 51 illustrate embodiments and components of embodiments of systems according to the invention which may be used to generate predetermined specific absorption rate profiles in selected tissue regions. FIGS. 2 through 25 and 48 through 51 illustrate embodiments and components of embodiments of systems according to the invention which may be used to generate predetermined specific absorption rate profiles such as, for example, the specific absorption rate profiles illustrated in FIGS. 26 through 51. FIGS. 2 through 25 and 48 through 51 illustrate embodiments and components of embodiments of systems according to the invention which may be used to generate predetermined specific absorption rate or power loss density profiles in selected tissue regions. FIGS. 2 through 25 and 48 through 51 illustrate embodiments and components of embodiments of systems according to the invention which may be used to generate predetermined power loss density profiles such as, for example, the power loss density profiles illustrated in FIGS. 26 through 51.

FIGS. 2 through 25 and 48 through 51 illustrate embodiments and components of embodiments of systems according to the invention which may be used to generate predetermined temperature profiles in selected tissue regions. FIGS. 2 through 25 and 48 through 51 illustrate embodiments and components of embodiments of systems according to the invention which may be used to generate predetermined temperature profiles such as, for example, the temperature profiles illustrated in FIGS. 26 through 51.

FIGS. 2 through 25 and 48 through 51 illustrate embodiments and components of embodiments of systems according to the invention which may be used to create lesions in selected tissue regions. FIGS. 2 through 25 and 48 through 51 illustrate embodiments and components of embodiments of systems according to the invention which may be used to create lesions in selected regions by generating specific absorption rate profiles with a peak in the selected tissue regions. FIGS. 2 through 25 and 48 through 51 illustrate embodiments and components of embodiments of systems according to the invention which may be used to create lesions in selected tissue by generating specific absorption rate profiles such as, for example, the specific absorption rate profiles illustrated in FIGS. 26 through 51, wherein the lesion is created in region of the tissue corresponding to the peak specific absorption rate. FIGS. 2 through 25 and 48 through 51 illustrate embodiments and components of embodiments of systems according to the invention which may be used to create lesions in selected regions by generating power loss density profiles with a peak in the selected tissue regions. FIGS. 2 through 25 and 48 through 51 illustrate embodiments and components of embodiments of systems according to the invention which may be used to create lesions in selected tissue by generating power loss density profiles such as, for example, the power loss density profiles illustrated in FIGS. 26 through 51, wherein the lesion is created in region of the tissue corresponding to the peak power loss density. FIGS. 2 through 25 and 48 through 51 illustrate embodiments and components of embodiments of systems according to the invention which may be used to create lesions in selected regions by generating temperature profiles with a peak in the selected tissue regions. FIGS. 2 through 25 and 48 through 51 illustrate embodiments and components of embodiments of systems according to the invention which may be used to create lesions in selected tissue by generating temperature profiles such as, for example, the temperature profiles illustrated in FIGS. 26 through 51 wherein the lesion is created in region of the tissue corresponding to the peak temperature. Further non-limiting examples of embodiments of microwave systems and apparatuses that may be used and configured as described above can be found, for example, at FIGS. 3-7C and pp. 8-13 of U.S. Provisional App. No. 60/912,899; and FIGS. 3-9 and 20-26 and pp. 34-48 and FIGS. 20-26 of U.S. Provisional App. No. 61/013,274 both incorporated by reference in their entireties, as well as illustrated and described, for example, in FIGS. 3A-7C and pp. 16-20 of Appendix 1 and FIGS. 20-26 and pp. 38-46 of Appendix 2.

Figure 2:
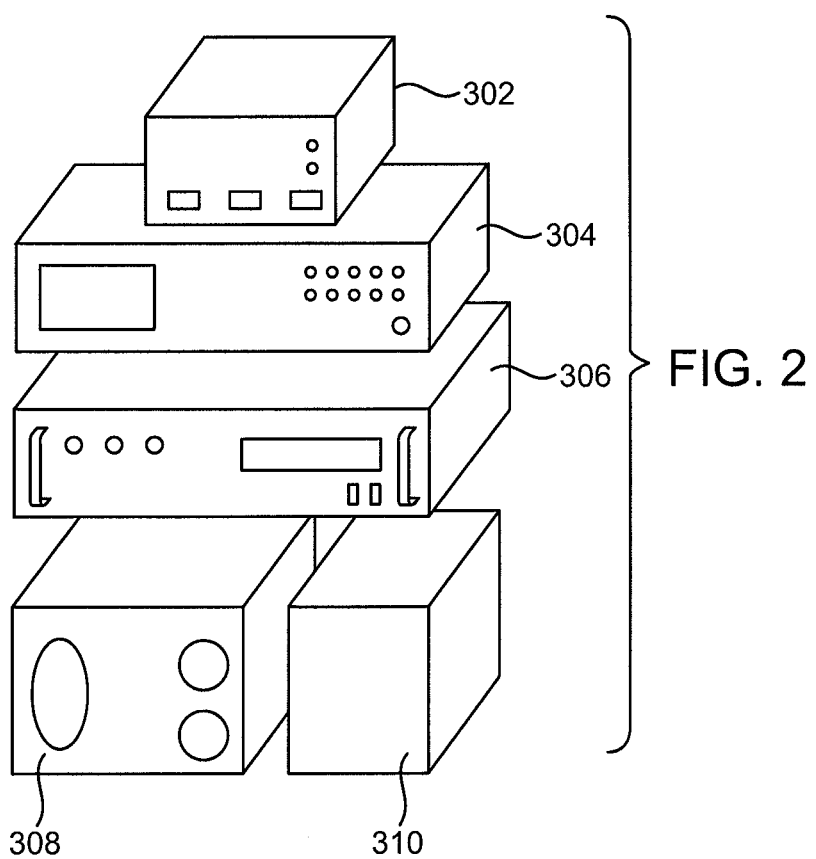
FIG. 2 illustrates a system for generating and controlling microwave energy according to one embodiment of the invention.

FIG. 2 illustrates one embodiment of a system for generating and controlling microwave energy according to one embodiment of the invention. In the embodiment illustrated in FIG. 2, controller 302 may be, for example, a custom digital logic timer controller module that controls the delivery of microwave energy generated by signal generator 304 and amplified by amplifier 306. Controller 302 may also control a solenoid valve to control application of vacuum from the vacuum source 308. In one embodiment of the invention, signal generator 304 may be, for example, a Model N5181A MXG Analog Signal Generator 100 KHz-6 GHz, available from Agilent Technologies. In one embodiment of the invention, amplifier 306 may be, for example, a Model HD18288SP High Power TWT Amplifier 5.7-18 GHz, available from HD Communications Corporation. In one embodiment of the invention, vacuum source 308 may be, for example, a Model 0371224 Basic 30 Portable Vacuum Pump, available from Medela. In one embodiment of the invention, coolant source 310 may be, for example, a 0P9TNAN001 NanoTherm Industrial Recirculating Chiller available from ThermoTek, Inc.

Figure 3:
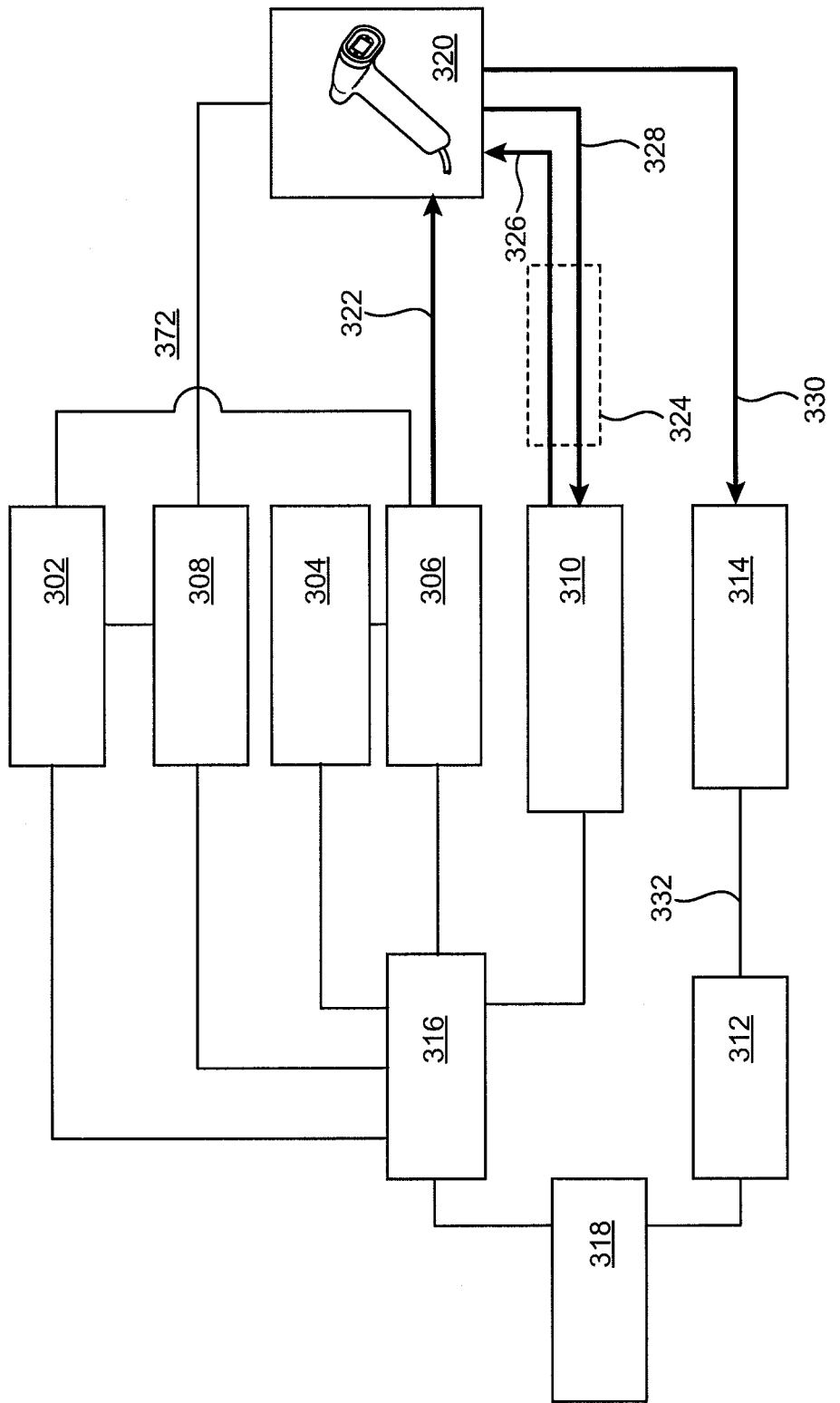
FIG. 3 illustrates a system for delivering microwave energy according to one embodiment of the invention.

FIG. 3 illustrates a system for delivering microwave energy according to one embodiment of the invention. In the embodiment of the invention illustrated in FIG. 3, power is supplied by power source 318, which may be, for example an AC mains power line. In the embodiment of the invention illustrated in FIG. 3, isolation transformer 316 isolates the mains power provided by power source 318 and supplies isolated power to controller 302, vacuum source 308, signal generator 304, amplifier 306, temperature data acquisition system 314 and coolant source 310. In one embodiment of the invention, vacuum cable 372 connects vacuum source 308 to applicator 320. In the embodiment of the invention illustrated in FIG. 3, signal generator 304 generates a signal, which may be, for example, a continuous wave (CW) signal having a frequency in the range of, for example, 5.8 GHz and that signal is supplied to amplifier 306, which is controlled by controller 302. In the embodiment of the invention illustrated in FIG. 3, an output signal from amplifier 306 may be transmitted to an applicator 320 by signal cable 322. In one embodiment of the invention, signal cable 322 may be, for example, a fiber optic link. In one embodiment of the invention, applicator 320 may be, for example, a microwave energy device. In the embodiment of the invention illustrated in FIG. 3, coolant source 310 may supply a coolant, such as, for example, chilled de-ionized water, to applicator 320 through coolant tubing 324, and, more particularly, coolant may be supplied to applicator 320 through inflow tubing 326 and returned to coolant source 310 through outflow tubing 328. In the embodiment of the invention illustrated in FIG. 3, applicator 320 includes temperature measurement devices which relay temperature signals 330 to the temperature data acquisition system 314, which, in turn, relays temperature signals by a fiber optic link 332 to the temperature display computer 312. In one embodiment of the invention, isolation transformer 316 may be ISB-100W Isobox, available from Toroid Corporation of Maryland. In one embodiment of the invention, temperature display computer 312 may be, for example, a custom timer controller developed from a number of off-the-shelf timer relay components and custom control circuitry. In one embodiment of the invention, temperature data acquisition system 314 may be, for example, a Thermes-USB Temperature Data Acquisition System with OPT-1 Optical Link available from Physitemp Instruments Inc.

Figure 4:
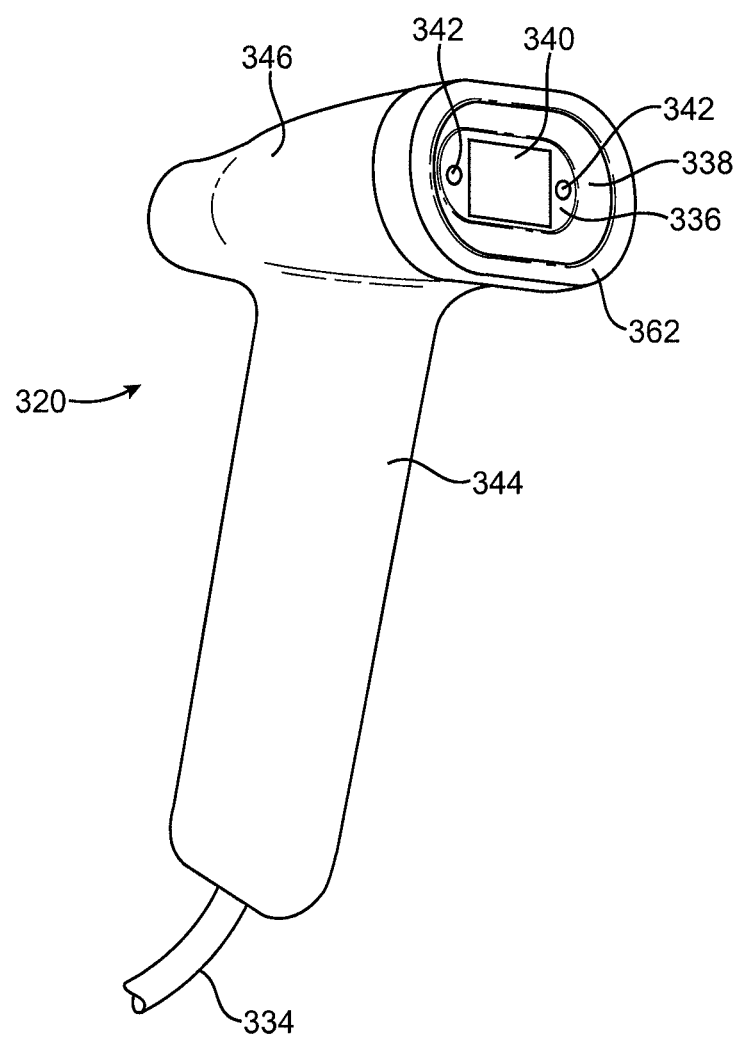
FIG. 4 is a side perspective view of a microwave applicator according to one embodiment of the invention
Figure 5:
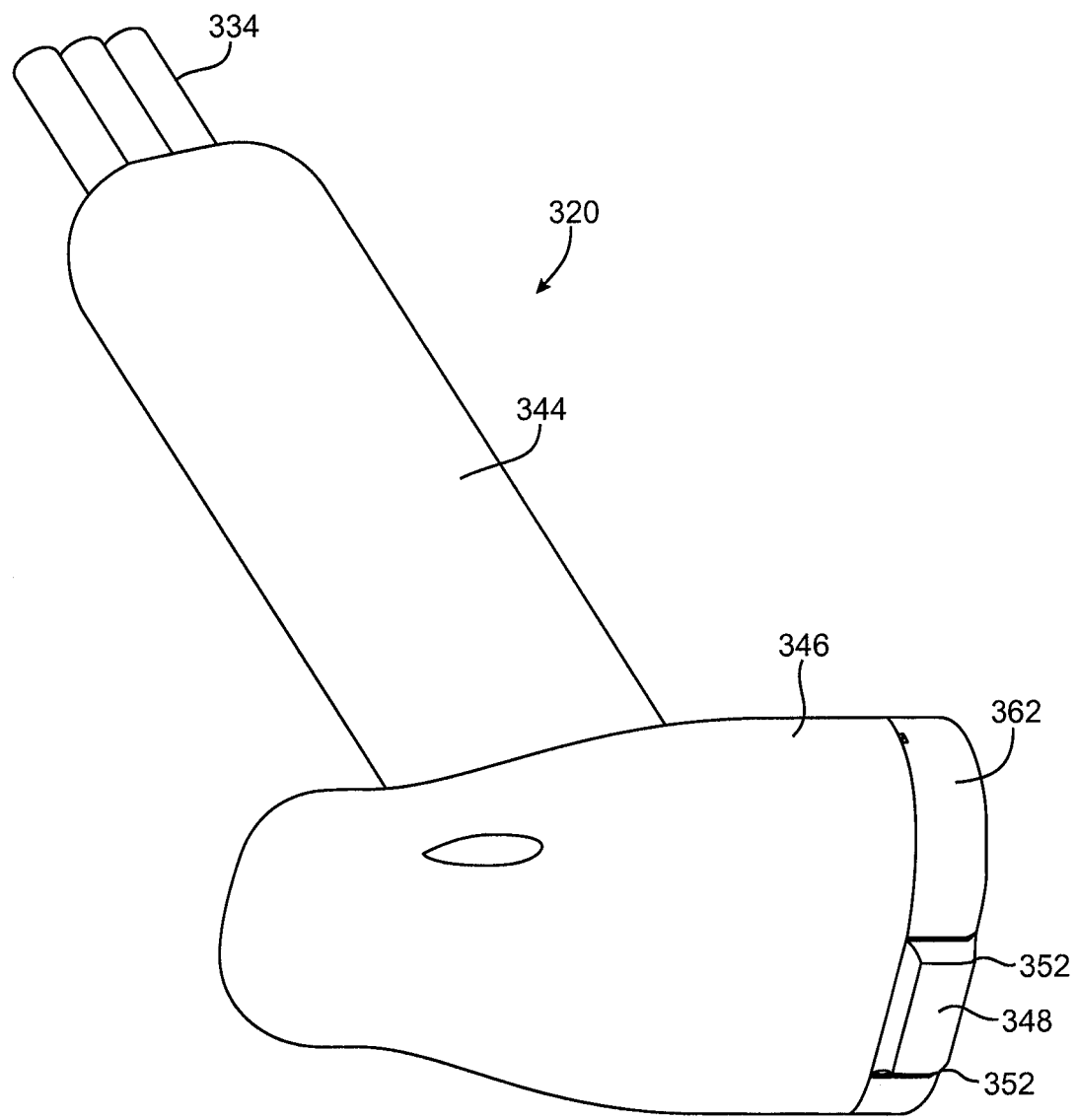
FIG. 5 is a top perspective view of a microwave applicator according to one embodiment of the invention.
Figure 6:
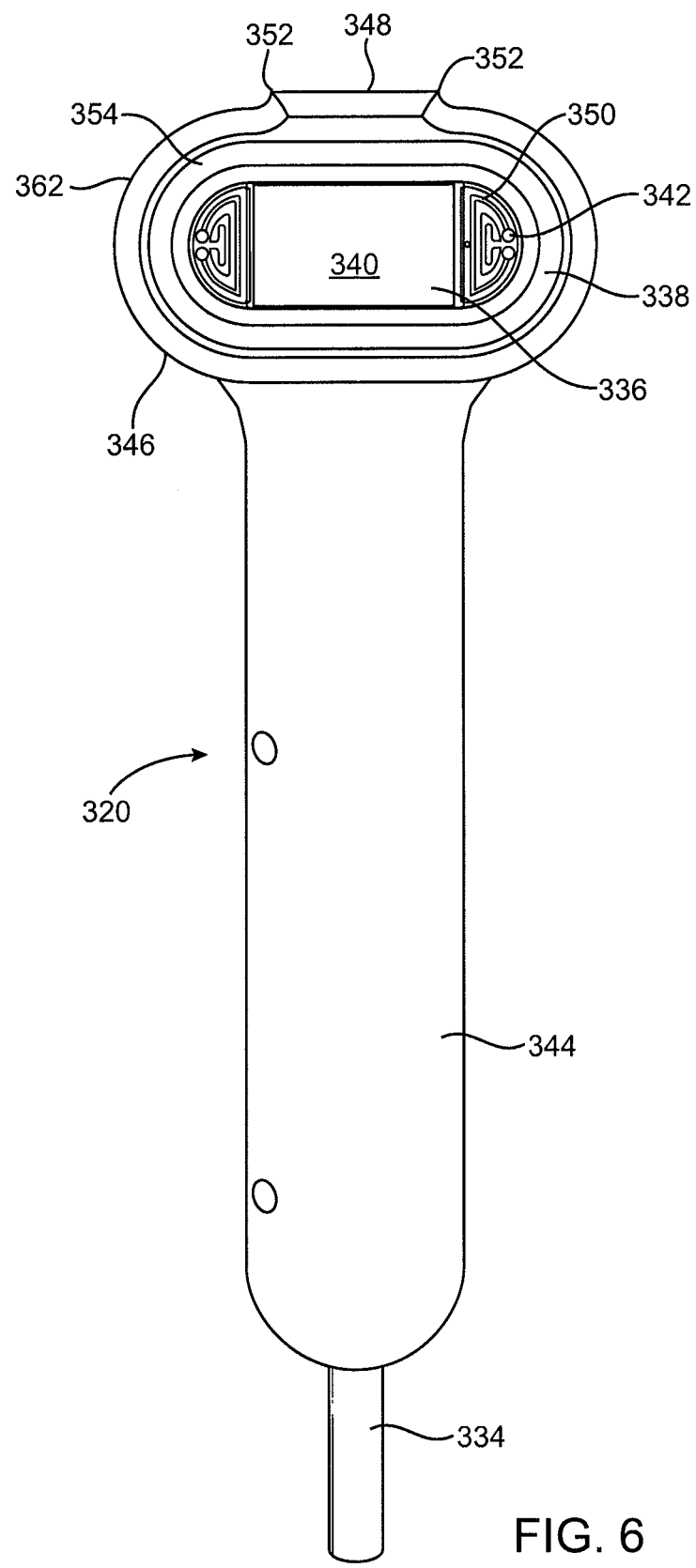
FIG. 6 is a front view of a microwave applicator according to one embodiment of the invention.

FIG. 4 is a side perspective view of a microwave applicator according to one embodiment of the invention. FIG. 5 is a top perspective view of a microwave applicator according to one embodiment of the invention. FIG. 6 is a front view of a microwave applicator according to one embodiment of the invention. In the embodiments of the invention illustrated in FIGS. 4 through 6, applicator 320 includes applicator cable 334, applicator handle 344, applicator head 346 and tissue head 362. In the embodiment of the invention illustrated in FIGS. 4 through 6, tissue head 362 includes vacuum ports 342, cooling plate 340, tissue chamber 338 and tissue interface 336. In one embodiment of the invention, tissue head 362 may be referred to as a tissue acquisition head. In the embodiment of the invention illustrated in FIG. 5, tissue head 362 includes alignment guide 348, which includes alignment features 352. In the embodiment of the invention illustrated in FIG. 6, tissue head 362 is mounted on applicator head 346 of applicator 320. In the embodiment of the invention illustrated in FIG. 6, tissue head 362 includes alignment guide 348, alignment features 352 and tissue chamber 338. In the embodiment of the invention illustrated in FIG. 6, tissue chamber 338 includes tissue wall 354 and tissue interface 336. In the embodiment of the invention illustrated in FIG. 6, tissue interface 336 includes cooling plate 340, vacuum ports 342 and vacuum channel 350.

Figure 7:
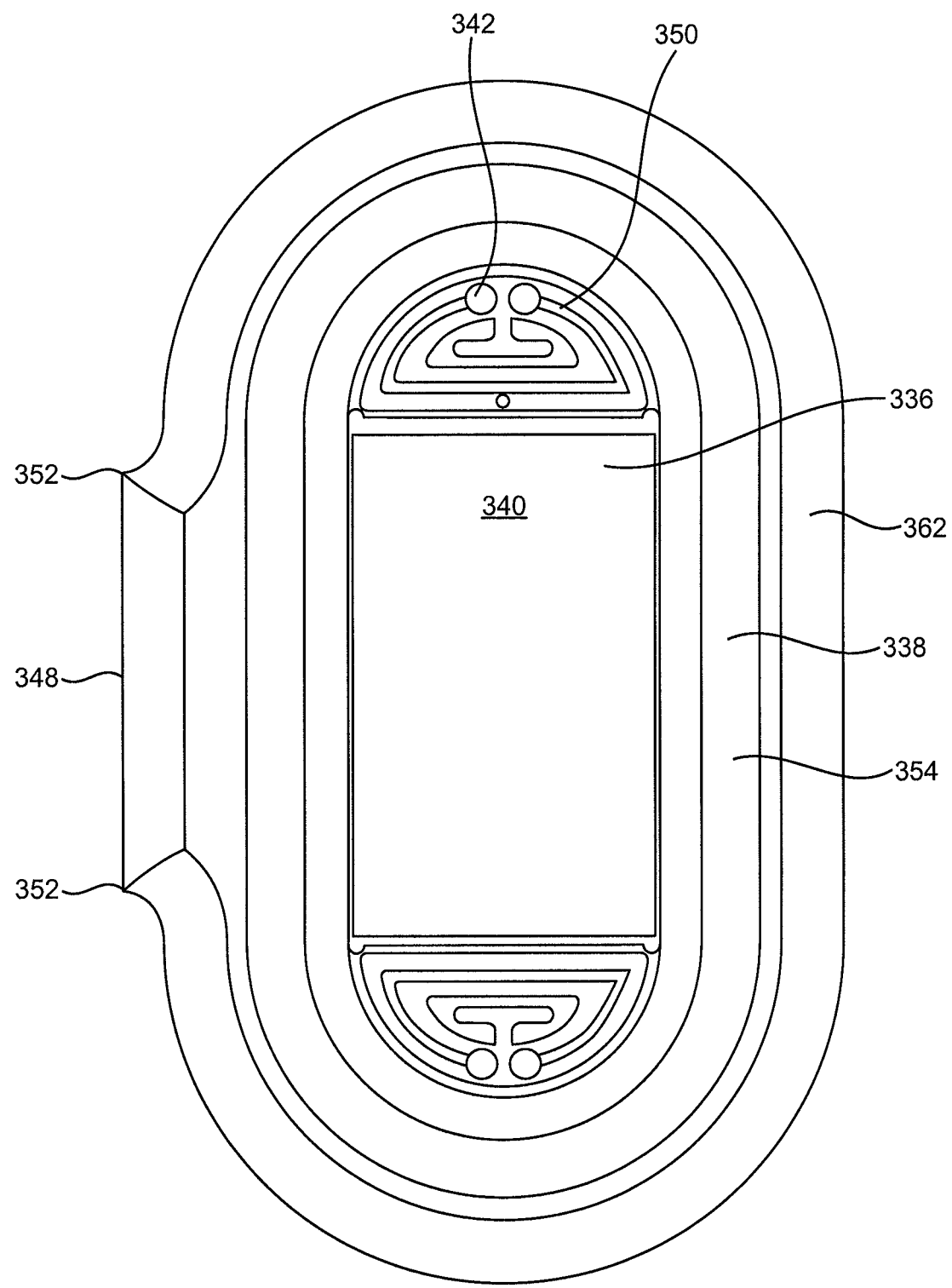
FIG. 7 is a front view of a tissue head for use with a microwave applicator according to one embodiment of the invention.

FIG. 7 is a front view of a tissue head for use with a microwave applicator according to one embodiment of the invention. In the embodiment of the invention illustrated in FIG. 7, tissue head 362 includes alignment guide 348, alignment features 352 and tissue chamber 338. In the embodiment of the invention illustrated in FIG. 7, tissue chamber 338 includes tissue wall 354 and tissue interface 336. In the embodiment of the invention illustrated in FIG. 7, tissue interface 336 includes cooling plate 340, vacuum ports 342 and vacuum channel 350. In one embodiment of the invention, tissue head 362 is detachable and may be used as a disposable element of a microwave applicator such as, for example, applicator 320.

Figure 8:
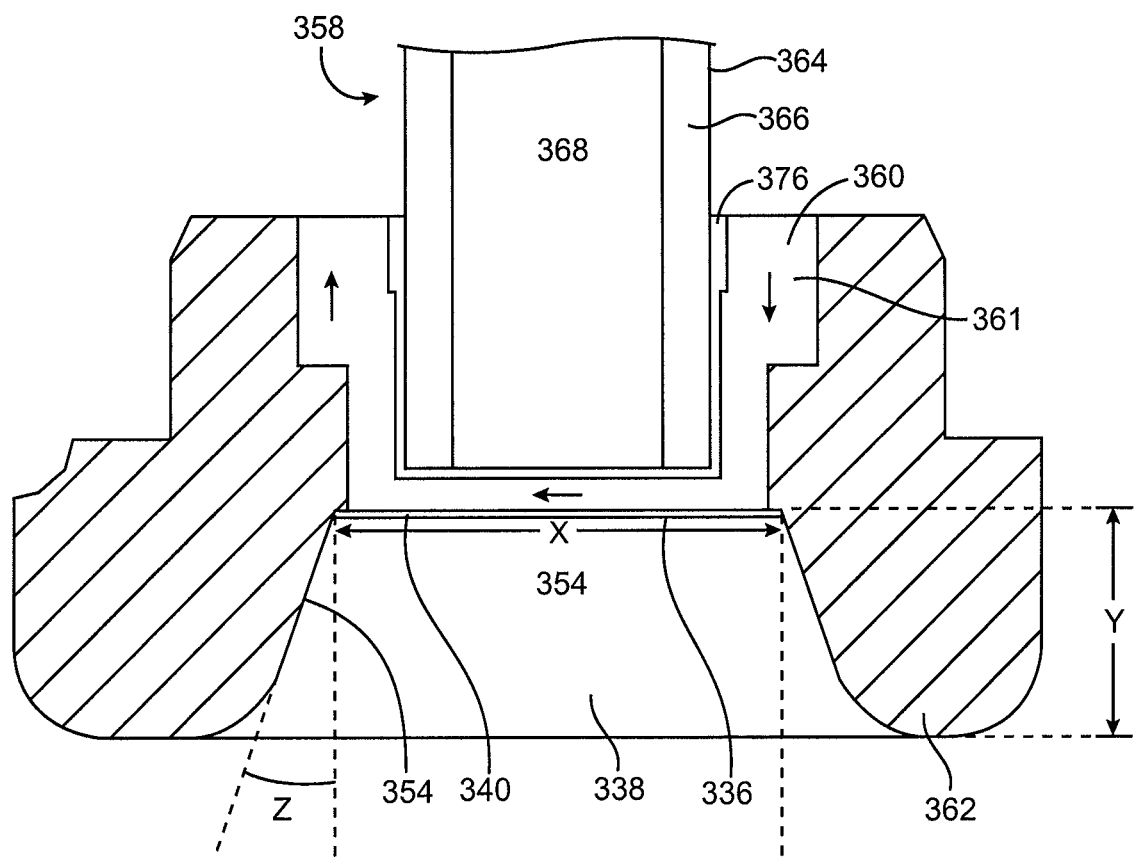
FIG. 8 is a cut away view of a tissue head according to one embodiment of the invention.

FIG. 8 is a cut away view of a tissue head according to one embodiment of the invention. FIG. 8 is a cutaway view of a tissue head 362 and antenna 358 according to one embodiment of the invention. In one embodiment of the invention, antenna 358 may be, for example, a waveguide 364 which may include, for example, waveguide tubing 366 and dielectric filler 368. In the embodiment of the invention illustrated in FIG. 8 antenna 358 is isolated from cooling fluid 361 in coolant chamber 360 by standoff 376. In the embodiment of the invention illustrated in FIG. 8, chamber wall 354 has a chamber angle Z which facilitates the acquisition of tissue. In the embodiment of the invention illustrated in FIG. 8 tissue interface 336, which may include cooling plate 340, has a minimum dimension X and tissue chamber 338 has a depth Y.

Figure 9:
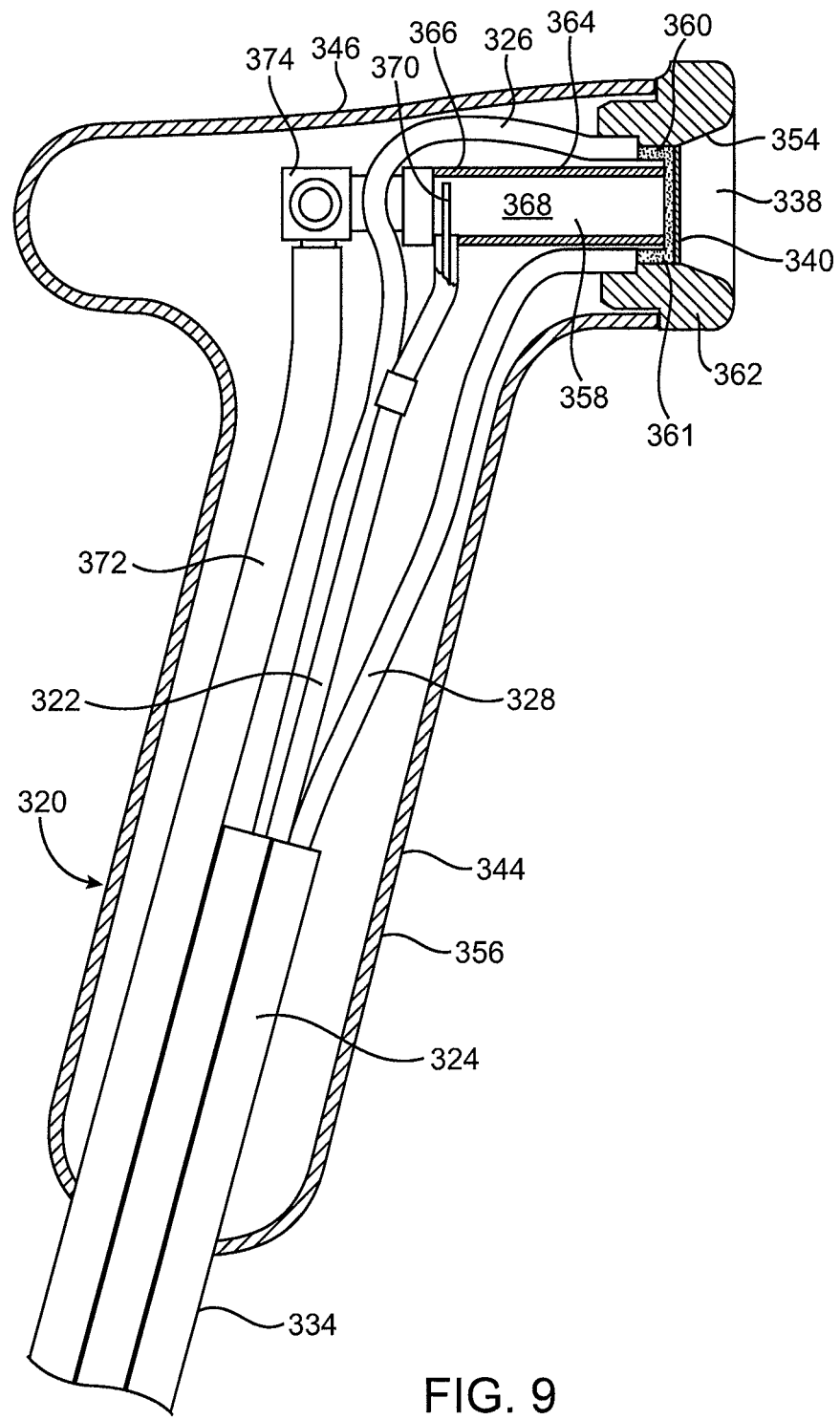
FIG. 9 is a side cutaway view of a microwave applicator according to one embodiment of the invention.
Figure 10:
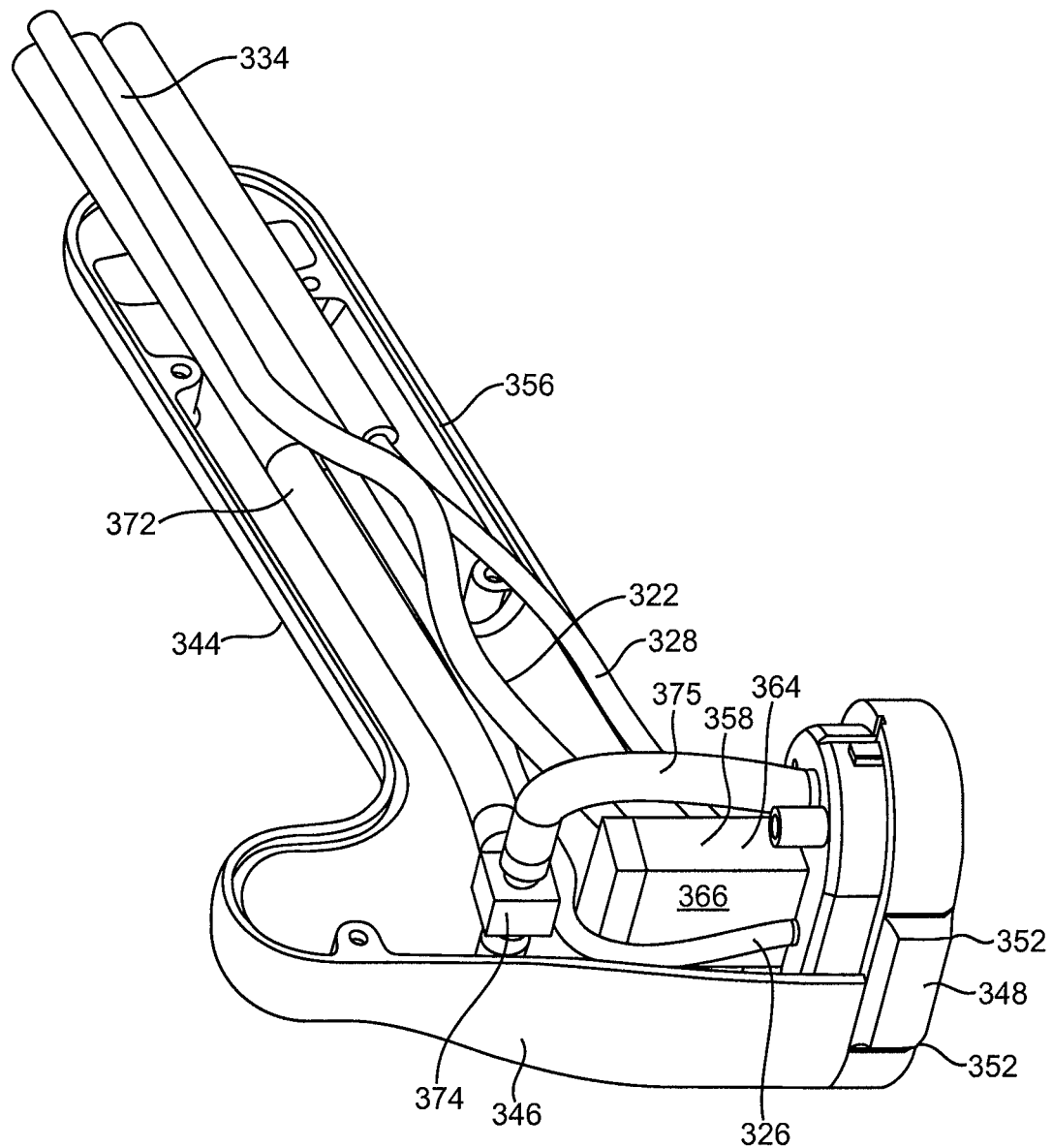
FIG. 10 is a top perspective partial cutaway view of a microwave applicator according to one embodiment of the invention.
Figure 11:
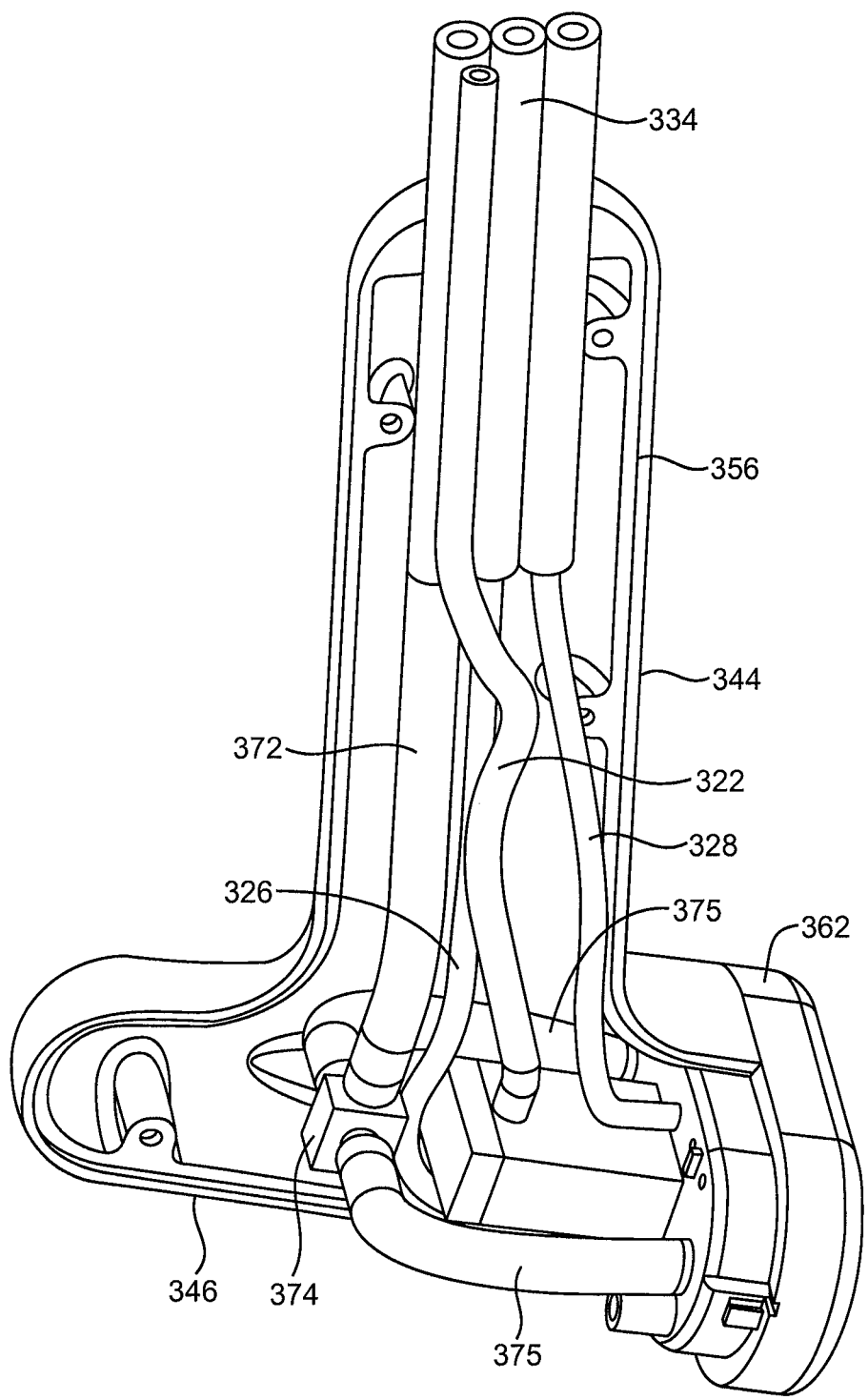
FIG. 11 is a side partial cutaway view of a microwave applicator according to one embodiment of the invention.

FIG. 9 is a side cutaway view of a microwave applicator according to one embodiment of the invention. FIG. 10 is a top perspective partial cutaway view of a microwave applicator according to one embodiment of the invention. FIG. 11 is a side partial cutaway view of a microwave applicator according to one embodiment of the invention. In the embodiment of the invention illustrated in FIGS. 9 through 11, applicator 320 includes applicator housing 356 and tissue head 362. In the embodiment of the invention illustrated in FIGS. 9 through 11, applicator housing 356 encloses applicator handle 344 and at least a portion of applicator head 346. In the embodiment of the invention illustrated in FIGS. 9 through 11 applicator cable 334 includes coolant tubing 324, inflow tubing 326, outflow tubing 328, signal cable 322 and vacuum cable 372. In the embodiment of the invention illustrated in FIGS. 9 through 11, vacuum cable 372 is connected to vacuum splitter 374. In the embodiment of the invention illustrated in FIGS. 9 through 11, applicator 320 includes antenna 358. In the embodiment of the invention illustrated in FIGS. 9 through 11, antenna 358 may include waveguide antenna 364. In the embodiment of the invention illustrated in FIGS. 9 through 11, waveguide antenna 364 may include dielectric filler 368 and waveguide tubing 366. In embodiments of the invention, cooling chamber 360 may be configured to facilitate the continuous flow of cooling fluid 361 across one surface of cooling plate 340. In the embodiment of the invention illustrated in FIGS. 9 through 11, signal cable 322 is connected to antenna 358 by antenna feed 370, which may be, for example a distal end of a semi-rigid coaxial cable or a panel mount connector and includes the center conductor of the cable or connector. In the embodiment of the invention illustrated in FIGS. 9 through 11, applicator 320 includes tissue head 362. In the embodiment of the invention illustrated in FIGS. 9 through 11, tissue head 362 includes tissue chamber 338, chamber wall 354, cooling plate 340 and cooling chamber 360. In the embodiment of the invention illustrated in FIGS. 9 through 11, cooling chamber 360 is connected to inflow tubing 326 and outflow tubing 328. In the embodiment of the invention illustrated in FIG. 10, vacuum cable 372 is connected to secondary vacuum cables 375. In the embodiment of the invention illustrated in FIG. 10, secondary vacuum cables 375 may be connected to vacuum ports 342 (not shown) in tissue head 362.

In the embodiment of the invention illustrated in FIG. 11, vacuum cable 372 is connected to secondary vacuum cables 375. In the embodiment of the invention illustrated in FIG. 11, secondary vacuum cables 375 may be connected to vacuum ports 342 (not shown) in tissue head 362.

Figure 12:
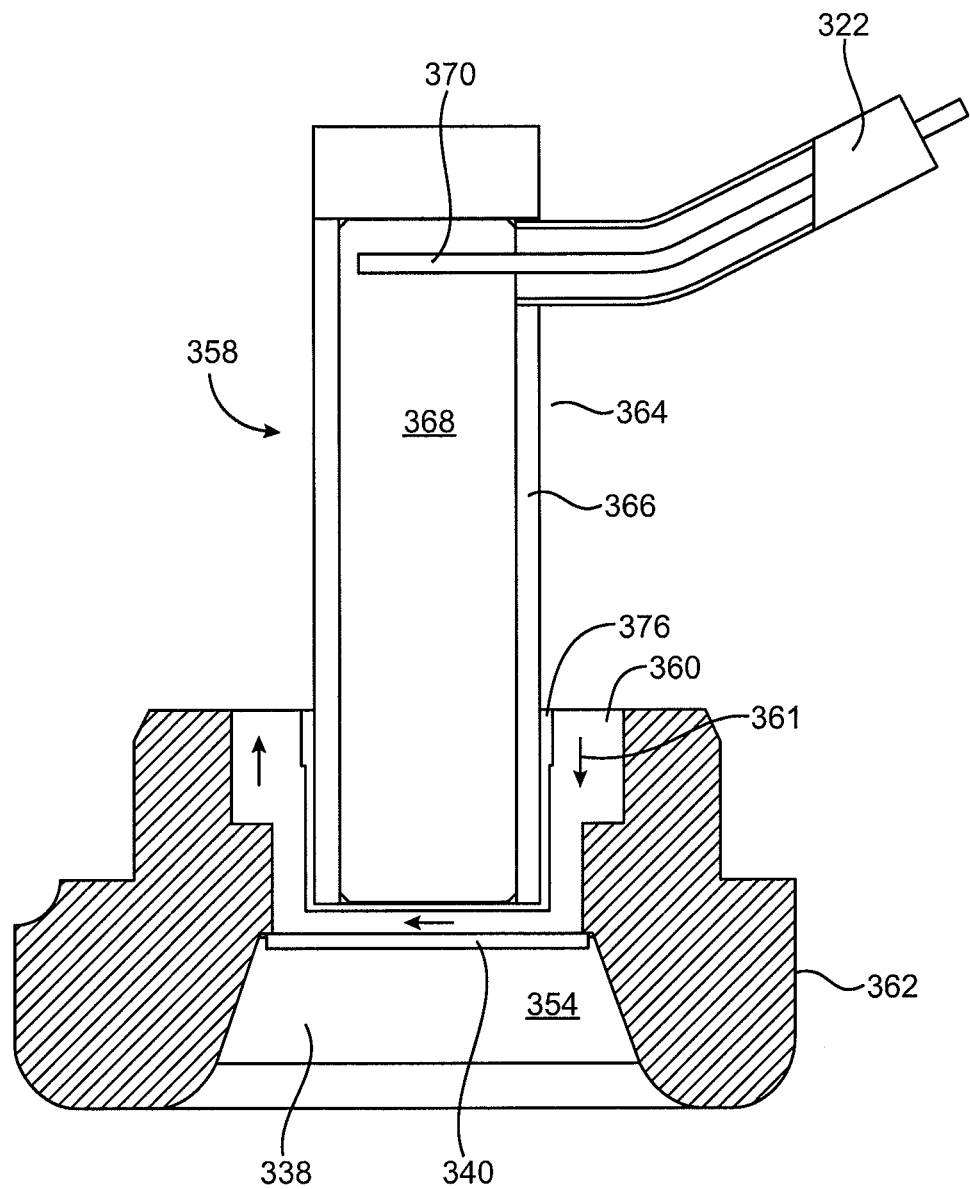
FIG. 12 is a cutaway view of a tissue head and antenna according to one embodiment of the invention.
Figure 13:
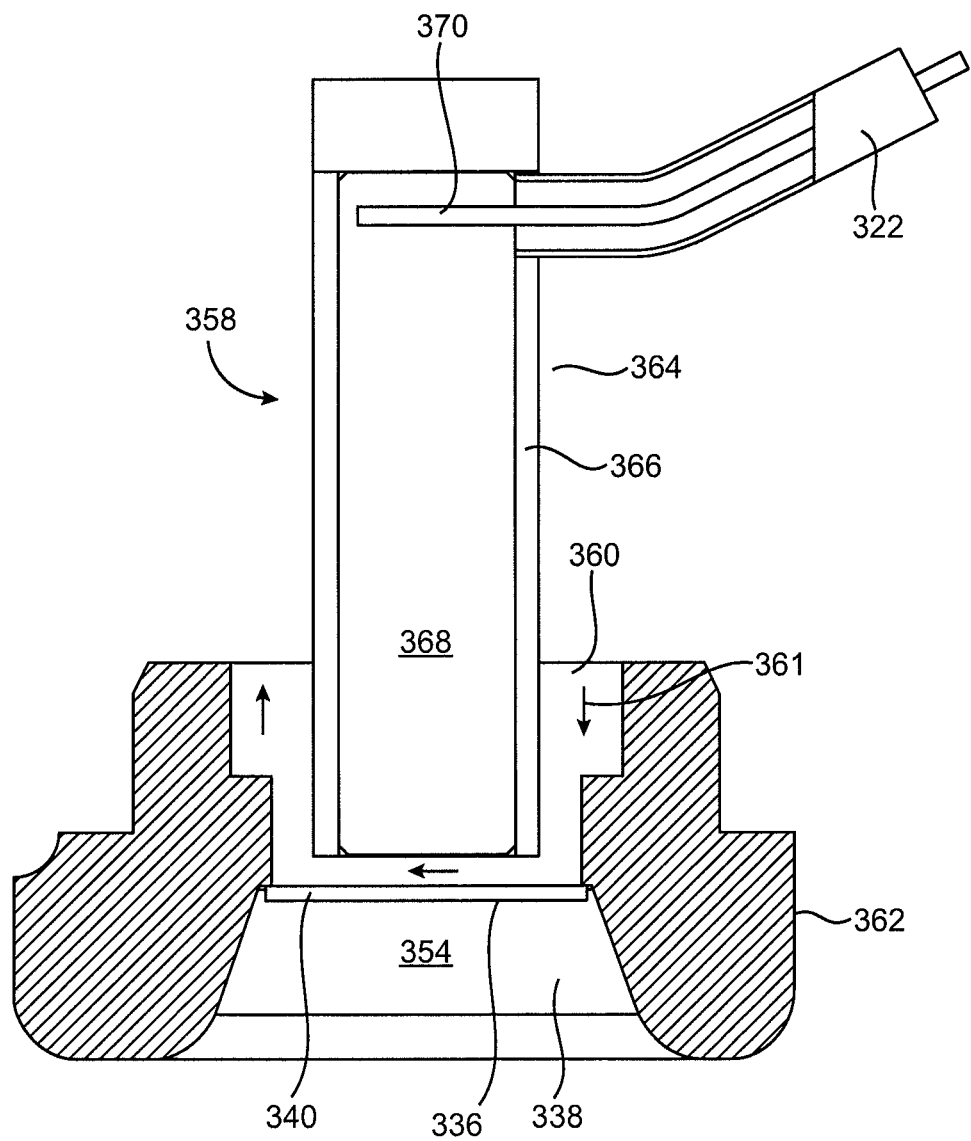
FIG. 13 is a cutaway view of a tissue head and antenna according to one embodiment of the invention.

FIGS. 12 and 13 are cutaway views of a tissue head and antenna according to one embodiment of the invention. FIGS. 14 through 18 are cutaway views of a tissue head, antenna and field spreader according to one embodiment of the invention. FIG. 19 is a cutaway view of a tissue head, antenna and field spreader with tissue engaged according to one embodiment of the invention. In the embodiments of the invention illustrated in FIGS. 12 through 19 antenna 358 may be, for example, a waveguide antenna 364. In the embodiments of the invention illustrated in FIGS. 12 through 19 waveguide antenna 364 may comprise, for example, waveguide tubing 366 and waveguide filler 368 and may be connected to signal cable 322 by, for example, antenna feed 370. In the embodiments of the invention illustrated in FIGS. 12 through 19 tissue head 362 may comprise, for example, tissue chamber 338, chamber wall 354, cooling plate 340 and cooling chamber 360. In the embodiments of the invention illustrated in FIGS. 12 through 19 cooling chamber 360 may include cooling fluid 361.

In the embodiment of the invention illustrated in FIG. 12 antenna 358 is isolated from cooling fluid 361 in coolant chamber 360 by standoff 376. In the embodiment of the invention illustrated in FIG. 13 at least a portion of antenna 358 is positioned in coolant chamber 360. In the embodiment of the invention illustrated in FIG. 13 at least a portion of waveguide antenna 364 is positioned in coolant chamber 360. In the embodiment of the invention illustrated in FIG. 13 waveguide antenna 364 is positioned in coolant chamber 360 such that at least a portion of waveguide tubing 366 and dielectric filler 368 contact cooling fluid 361 in coolant chamber 360.

Figure 14:
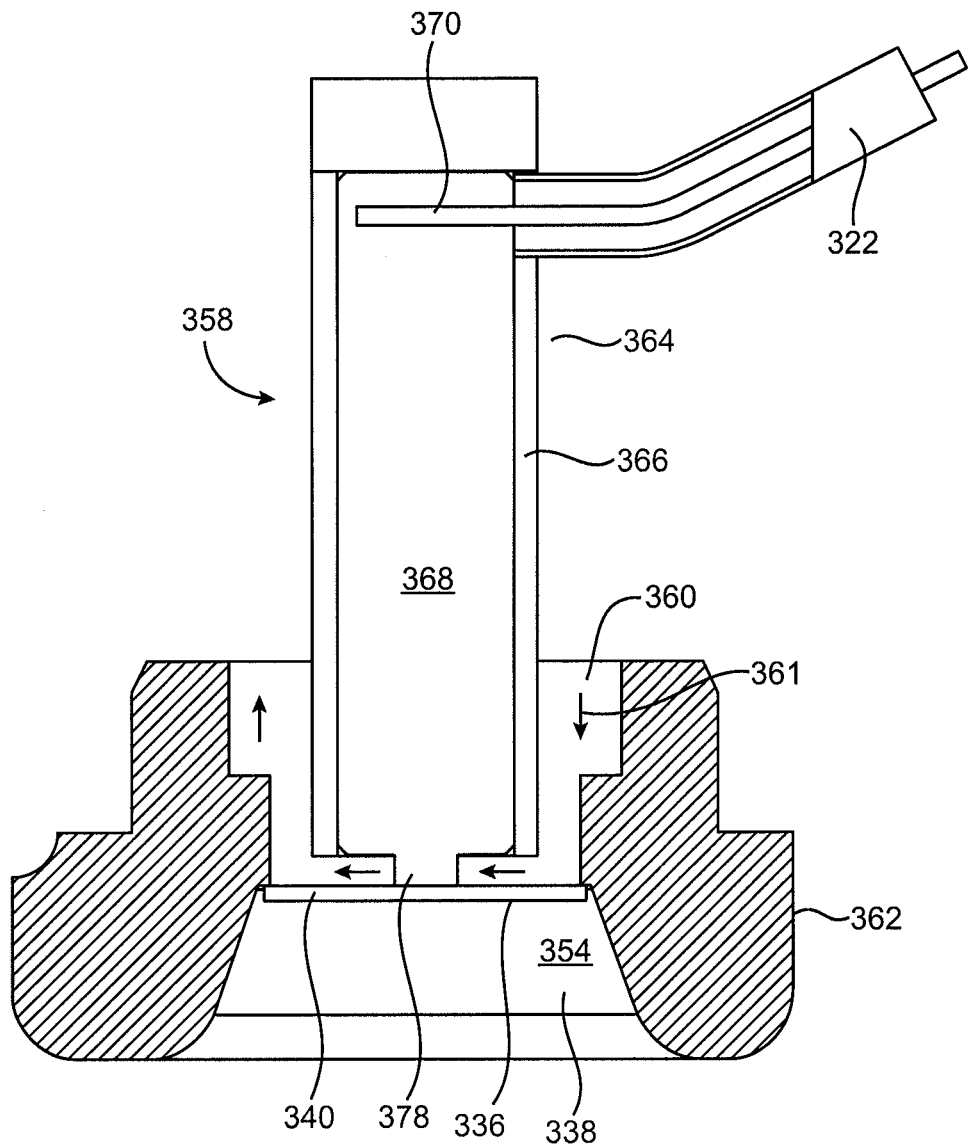
FIG. 14 is a cutaway view of a tissue head, antenna and field spreader according to one embodiment of the invention.

In one embodiment of the invention illustrated in FIG. 14 field spreader 378 is positioned at an output of waveguide antenna 364. In one embodiment of the invention illustrated in FIG. 14 field spreader 378 is an extension of dielectric filler 368 and is positioned at an output of waveguide antenna 364. In one embodiment of the invention illustrated in FIG. 14 field spreader 378 is an extension of dielectric filler 368 extending into coolant chamber 360. In one embodiment of the invention illustrated in FIG. 14 field spreader 378 is an extension of dielectric filler 368 extending through coolant chamber 360 to cooling plate 340.

Figure 15:
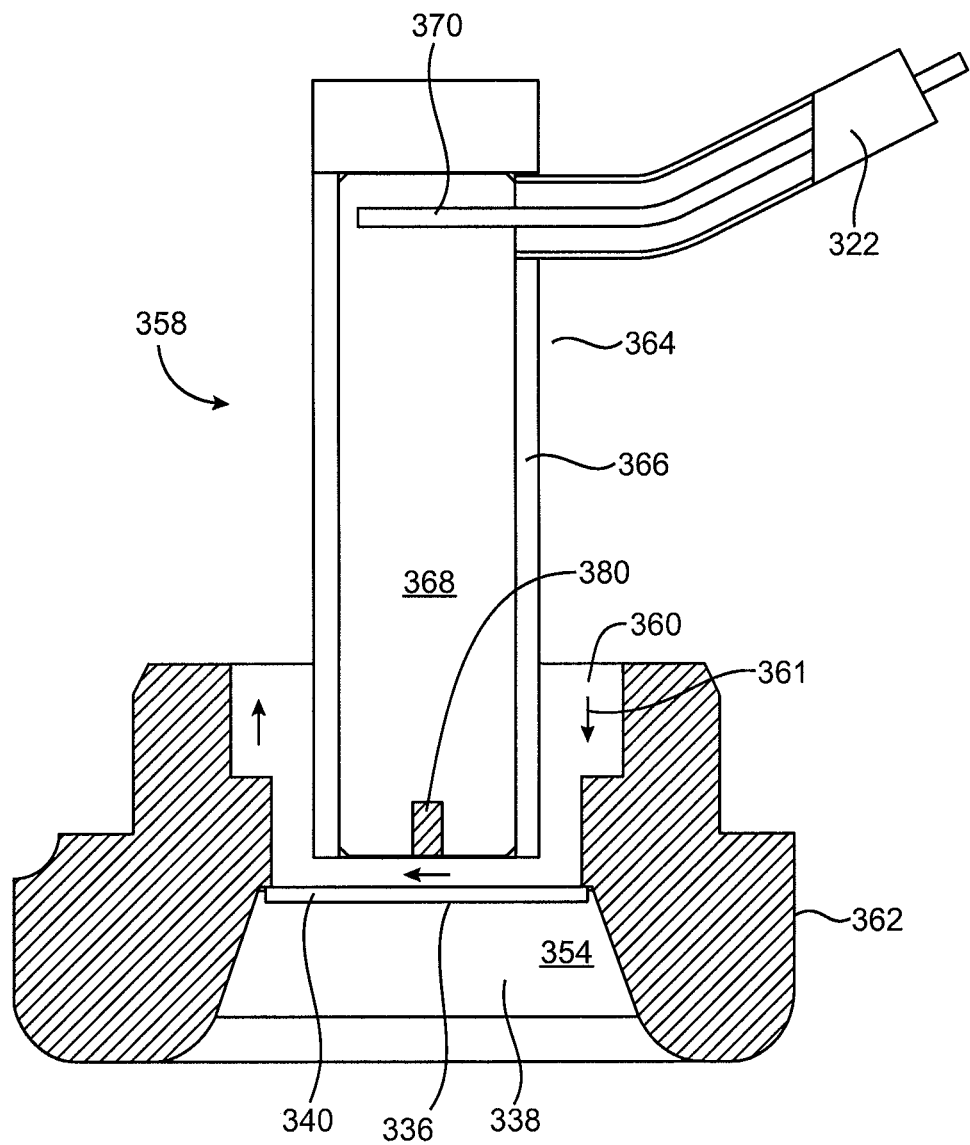
FIG. 15 is a cutaway view of a tissue head, antenna and field spreader according to one embodiment of the invention.

In one embodiment of the invention illustrated in FIG. 15 field spreader 380 is integrated into dielectric filler 368 of waveguide antenna 364. In one embodiment of the invention illustrated in FIG. 15 field spreader 380 is a region of dielectric filler 368 having a dielectric constant which differs from the dielectric constant of the remainder of dielectric filler 368. In one embodiment of the invention illustrated in FIG. 15 field spreader 380 is a region having a dielectric constant which is in the range of approximately 1 to 15.

Figure 16:
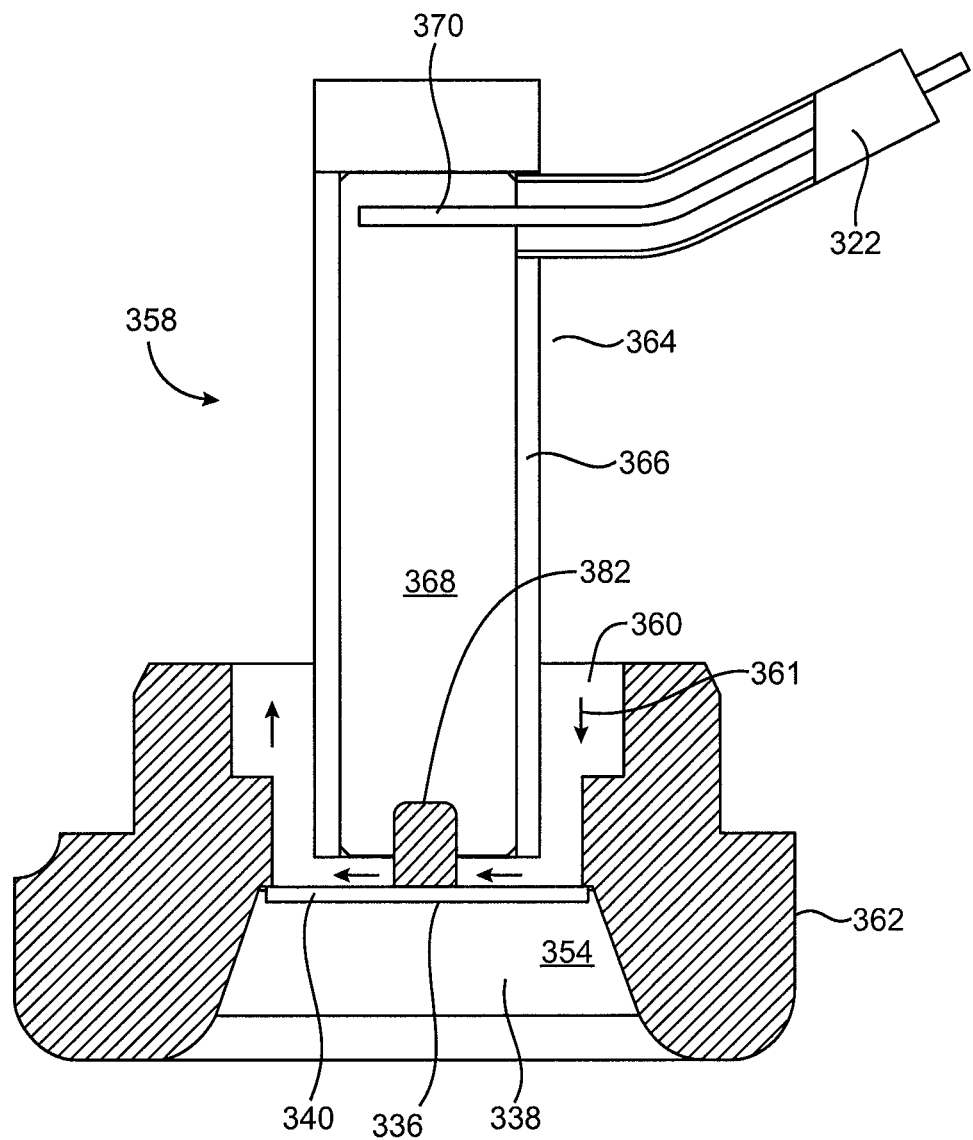
FIG. 16 is a cutaway view of a tissue head, antenna and field spreader according to one embodiment of the invention.
Figure 17:
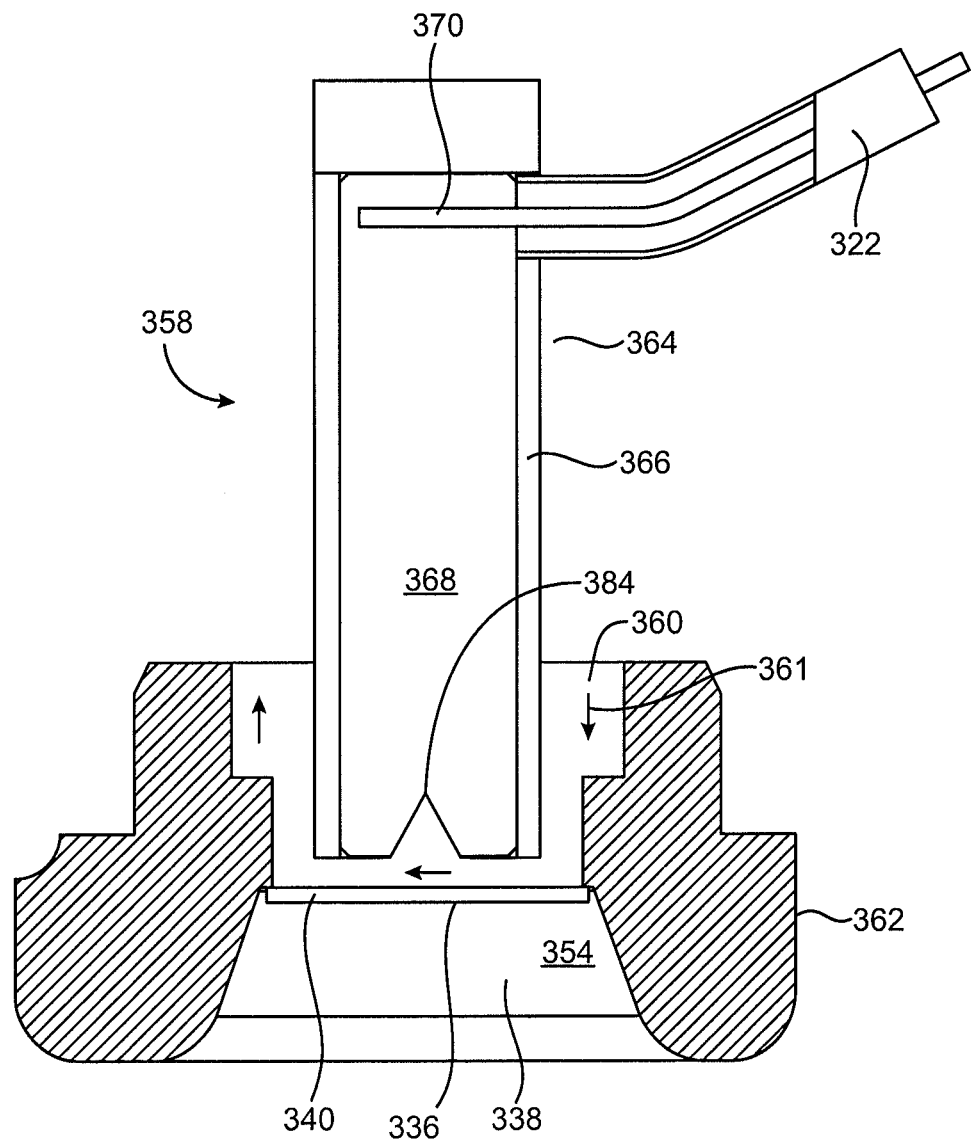
FIG. 17 is a cutaway view of a tissue head, antenna and field spreader according to one embodiment of the invention.

In one embodiment of the invention illustrated in FIG. 16 field spreader 382 is integrated into dielectric filler 368 of waveguide antenna 364 and extends into coolant chamber 360. In one embodiment of the invention illustrated in FIG. 16 field spreader 382 is integrated into dielectric filler 368 of waveguide antenna 364 and extends through coolant chamber 360 to cooling plate 340. In one embodiment of the invention illustrated in FIG. 16 field spreader 382 has a dielectric constant which differs from the dielectric constant of dielectric filler 368. In one embodiment of the invention illustrated in FIG. 15 field spreader 380 is a region having a dielectric constant which is in the range of approximately 1 to 15. In one embodiment of the invention illustrated in FIG. 17, a field spreader may be comprised of a notch 384 in dielectric filler 368. In one embodiment of the invention illustrated in FIG. 17, notch 384 is a cone shaped notch in dielectric filler 368. In one embodiment of the invention illustrated in FIG. 17, notch 384 is connected to cooling chamber 360 such that cooling fluid 361 in cooling chamber 360 at least partially fills notch 384. In one embodiment of the invention illustrated in FIG. 17, notch 384 is connected to cooling chamber 360 such that cooling fluid 361 in cooling chamber 360 fills notch 384.

Figure 18:
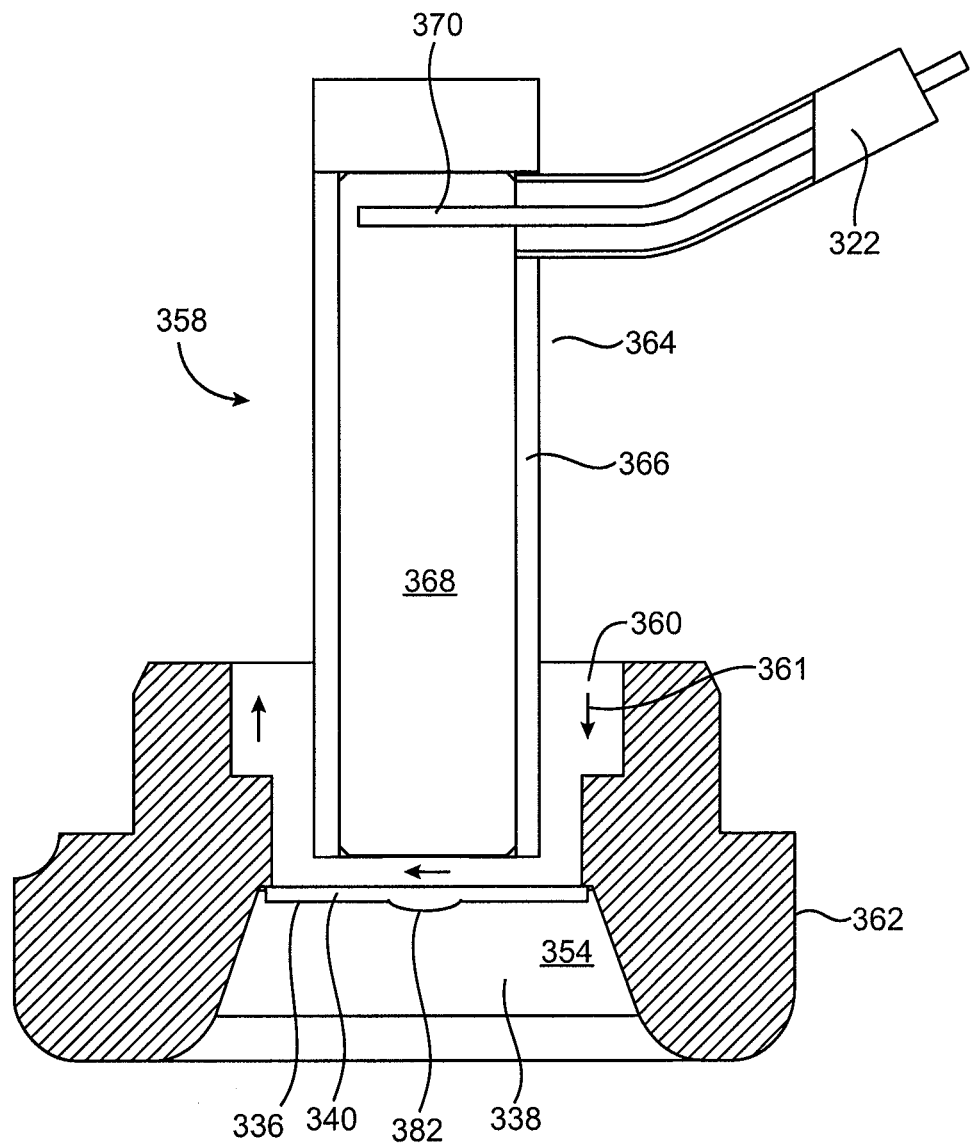
FIG. 18 is a is a cutaway view of a tissue head, antenna and field spreader according to one embodiment of the invention.
Figure 19:
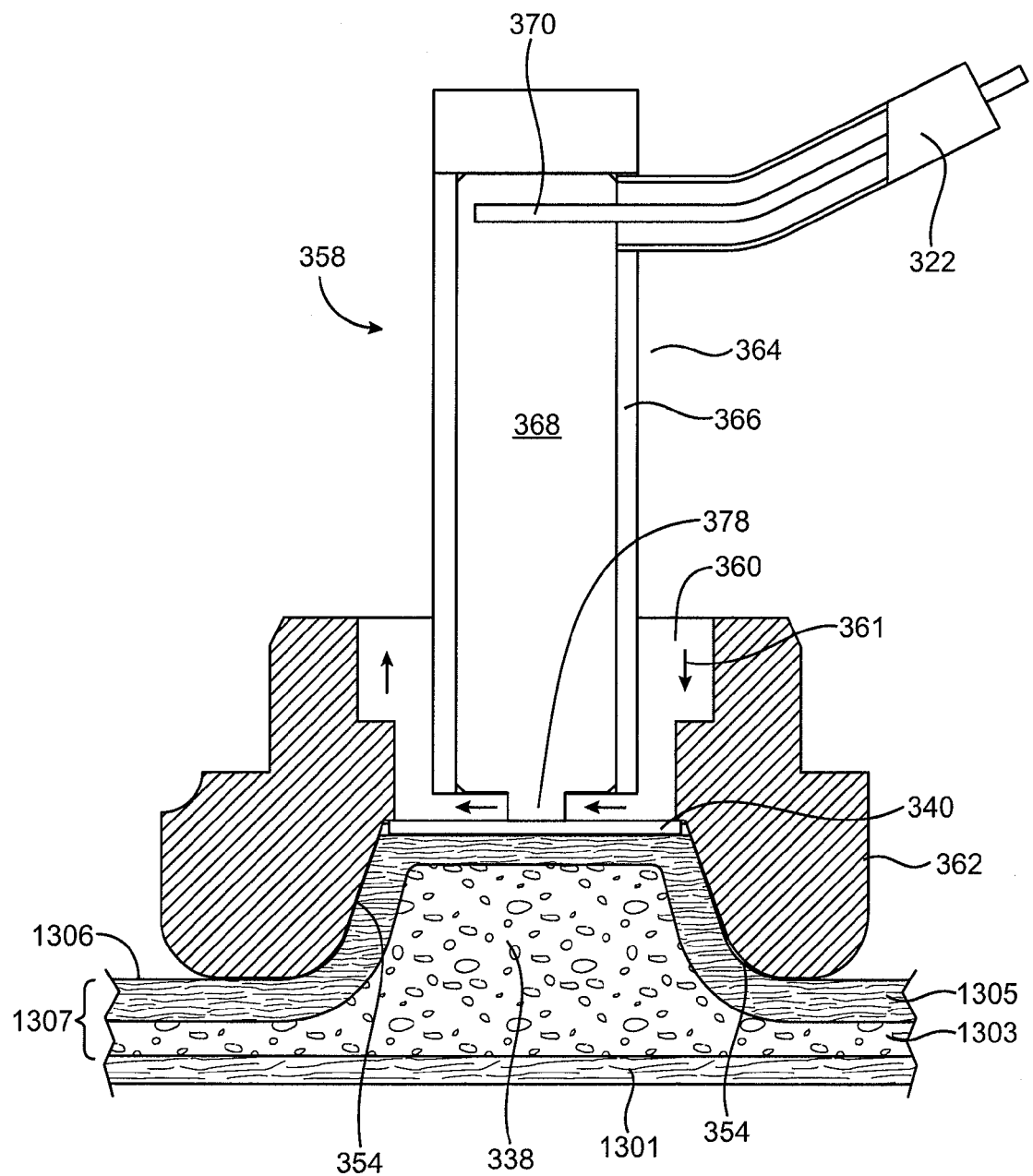
FIG. 19 is a cutaway view of a tissue head, antenna and field spreader with tissue engaged according to one embodiment of the invention.

In one embodiment of the invention illustrated in FIG. 18 field spreader 382 is integrated into or protrudes from cooling plate 340. In one embodiment of the invention illustrated in FIG. 18 field spreader 382 is integrated into or protrudes from cooling plate 340 at tissue interface 336. In one embodiment of the invention illustrated in FIG. 18 field spreader 382 is integrated into or protrudes from cooling plate 340 into tissue chamber 338. In one embodiment of the invention illustrated in FIG. 18 field spreader 382 may form at least a portion of tissue interface 336.

In the embodiment of the invention illustrated in FIG. 19 skin 1307 is engaged in tissue chamber 338. In the embodiment of the invention illustrated in FIG. 19 dermis 1305 and hypodermis 1303 are engaged in tissue chamber 338. In the embodiment of the invention illustrated in FIG. 19, skin surface 1306 is engaged in tissue chamber 338 such that skin surface 1306 is in contact with at least a portion of chamber wall 354 and cooling plate 340. In the embodiment of the invention illustrated in FIG. 19, skin surface 1306 is engaged in tissue chamber 338 such that skin surface 1306 is in contact with at least a portion of tissue interface 336. As illustrated in FIG. 19, a vacuum pressure may be used to elevate dermis 1305 and hypodermis 1303, separating dermis 1305 and hypodermis 1303 from muscle 1301. As illustrated in FIG. 19, a vacuum pressure may be used to elevate dermis 1305 and hypodermis 1303, separating dermis 1305 and hypodermis 1303 from muscle 1301 to, for example, protect muscle 1301 by limiting or eliminating the electromagnetic energy which reaches muscle 1301.

Figure 20:
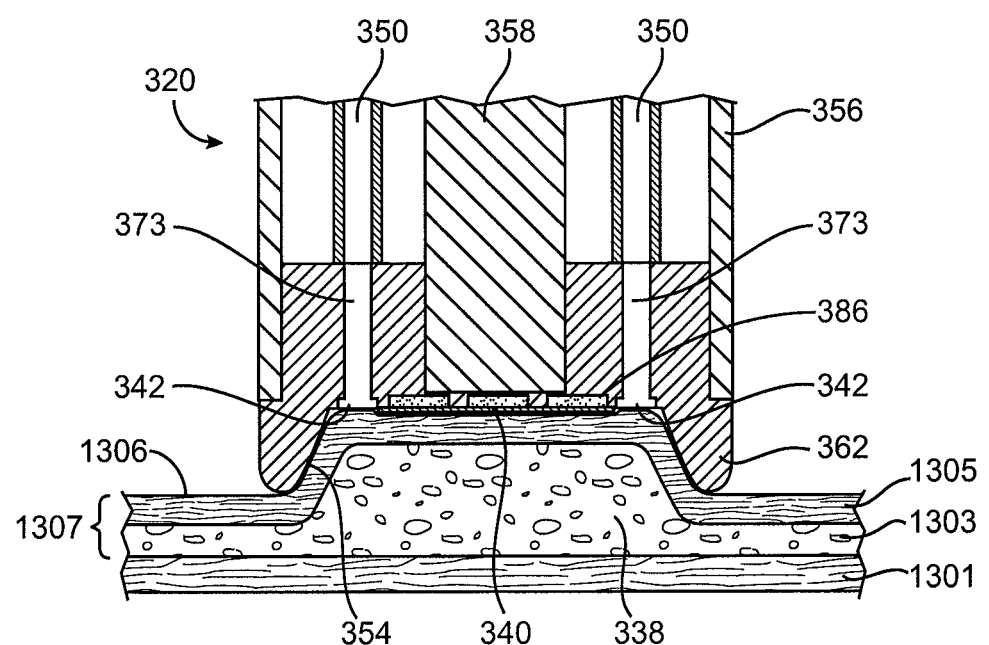
FIG. 20 is a cutaway view of a tissue head and antenna and with tissue engaged according to one embodiment of the invention.

FIG. 20 is a cutaway view of a tissue head and antenna with tissue engaged according to one embodiment of the invention. In the embodiment of the invention illustrated in FIG. 20 applicator 320 includes applicator housing 356, antenna 358, vacuum channels 350 and tissue head 362. In the embodiment of the invention illustrated in FIG. 20 tissue head 362 includes vacuum conduit 373, cooling elements 386 and cooling plate 340. In embodiments of the invention, cooling elements 386 may be, for example: solid coolants; heat sinks; liquid spray, gaseous spray, cooling plates, thermo-electric coolers; or and combinations thereof. In the embodiment of the invention illustrated in FIG. 20 vacuum channels 350 are connected to vacuum conduit 373 and vacuum port 342. In the embodiment of the invention illustrated in FIG. 20 skin surface 1306 is engaged in tissue chamber 338 by, for example a vacuum pressure at vacuum ports 342, such that skin surface 1306 is in contact with at least a portion of chamber wall 354 and cooling plate 340. In the embodiment of the invention illustrated in FIG. 20 skin surface 1306 is engaged in tissue chamber 338 by, for example a vacuum pressure at vacuum ports 342, such that skin surface 1306 is in contact with at least a portion of tissue interface 336. As illustrated in FIG. 20, a vacuum pressure at vacuum ports 342 may be used to elevate dermis 1305 and hypodermis 1303, separating dermis 1305 and hypodermis 1303 from muscle 1301. As illustrated in FIG. 20, a vacuum pressure at vacuum ports 342 may be used to elevate dermis 1305 and hypodermis 1303, separating dermis 1305 and hypodermis 1303 from muscle 1301 to, for example, protect muscle 1301 by limiting or eliminating the electromagnetic energy which reaches muscle 1301.

Figure 21:
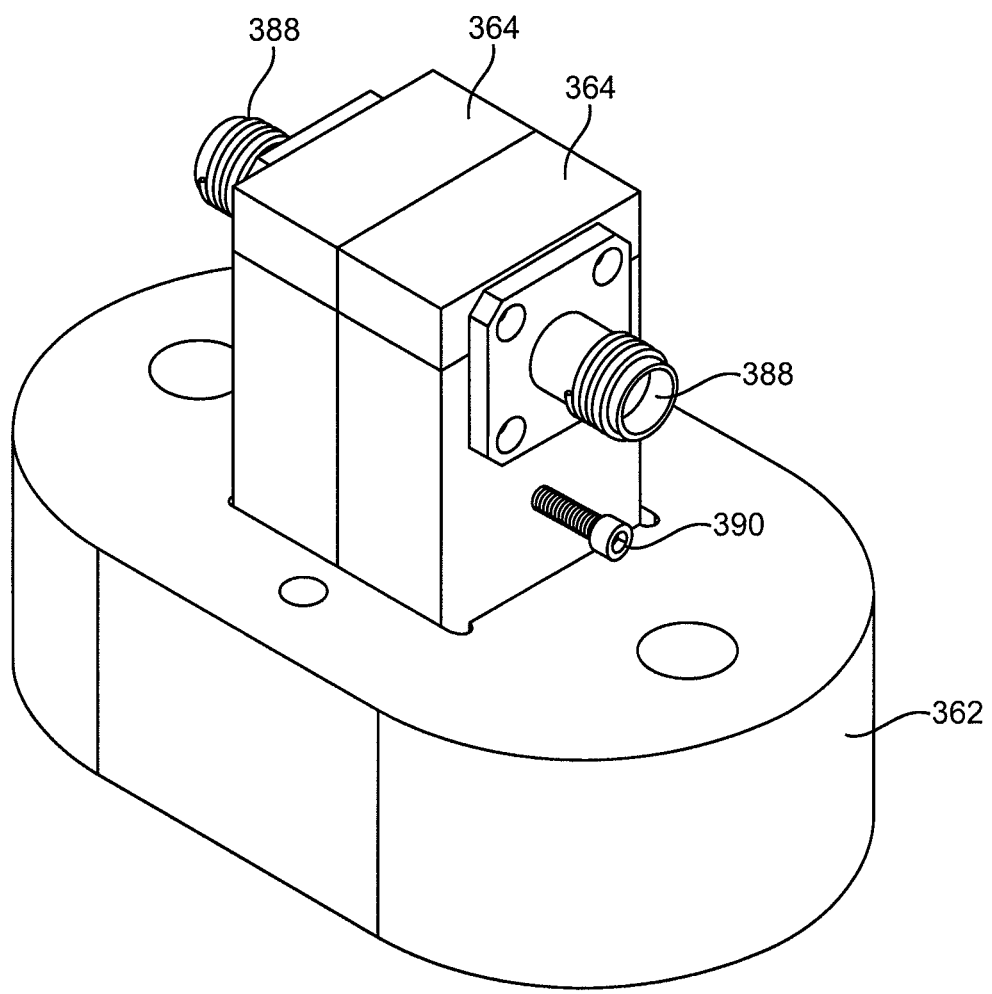
FIG. 21 illustrates a tissue head including a plurality of waveguide antennas according to one embodiment of the invention.
Figure 22:
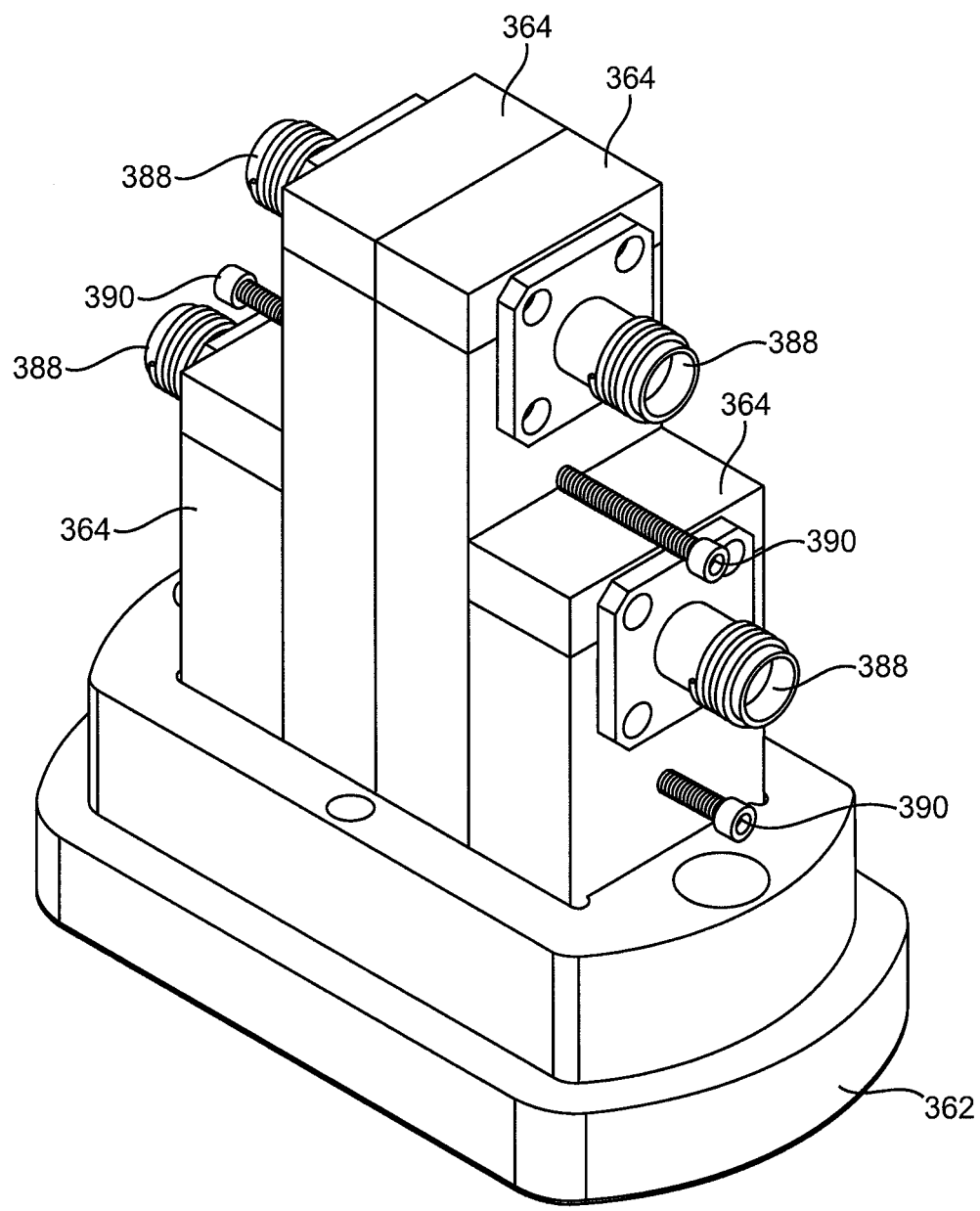
FIG. 22 illustrates a tissue head including a plurality of waveguide antennas according to one embodiment of the invention.
Figure 23:
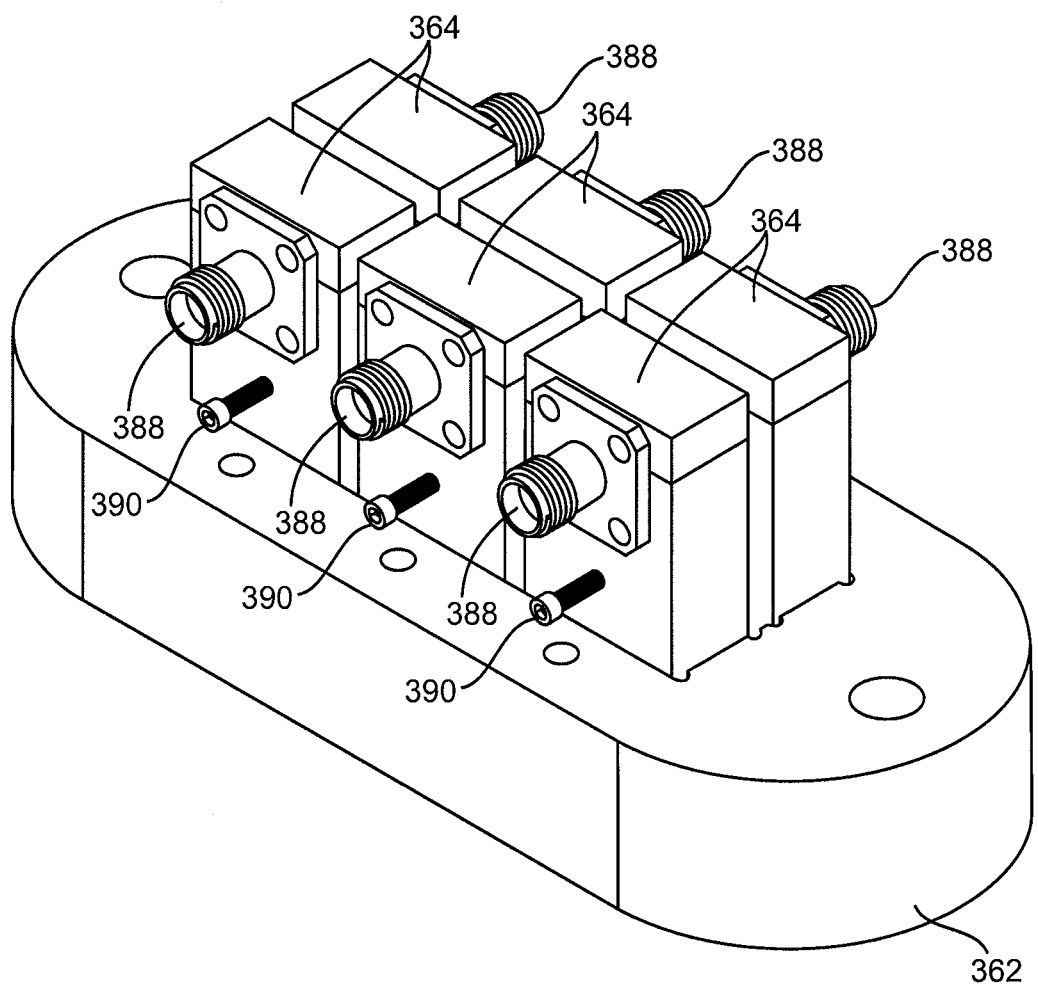
FIG. 23 illustrates a tissue head including a plurality of waveguide antennas according to one embodiment of the invention.

FIGS. 21 through 23 illustrate tissue heads including a plurality of waveguide antennas according to one embodiment of the invention. In the embodiments of the invention illustrated in FIGS. 21 through 23 a tissue head 362 includes a plurality of waveguide antennas 364 according to embodiments of the invention. In the embodiment of the invention illustrated in FIG. 21, two waveguide antennas 364 are positioned in tissue head 362. In the embodiment of the invention illustrated in FIG. 22, four waveguide antennas 364 are positioned in tissue head 362. In the embodiment of the invention illustrated in FIG. 23, six waveguide antennas 364 are positioned in tissue head 362. In the embodiment of the invention illustrated in FIGS. 21 through 23 waveguides 364 include feed connectors 388 and tuning screws 390.

Figure 24:
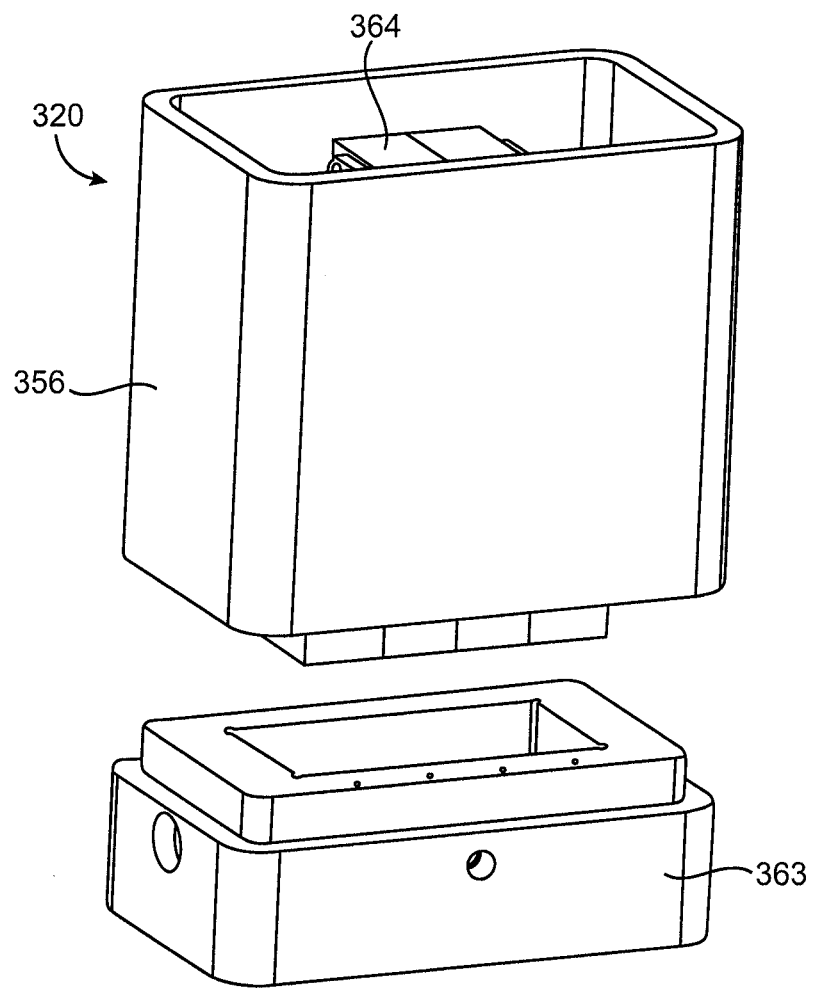
FIG. 24 illustrates a disposable tissue head for use with an applicator according to one embodiment of the invention.
Figure 25:
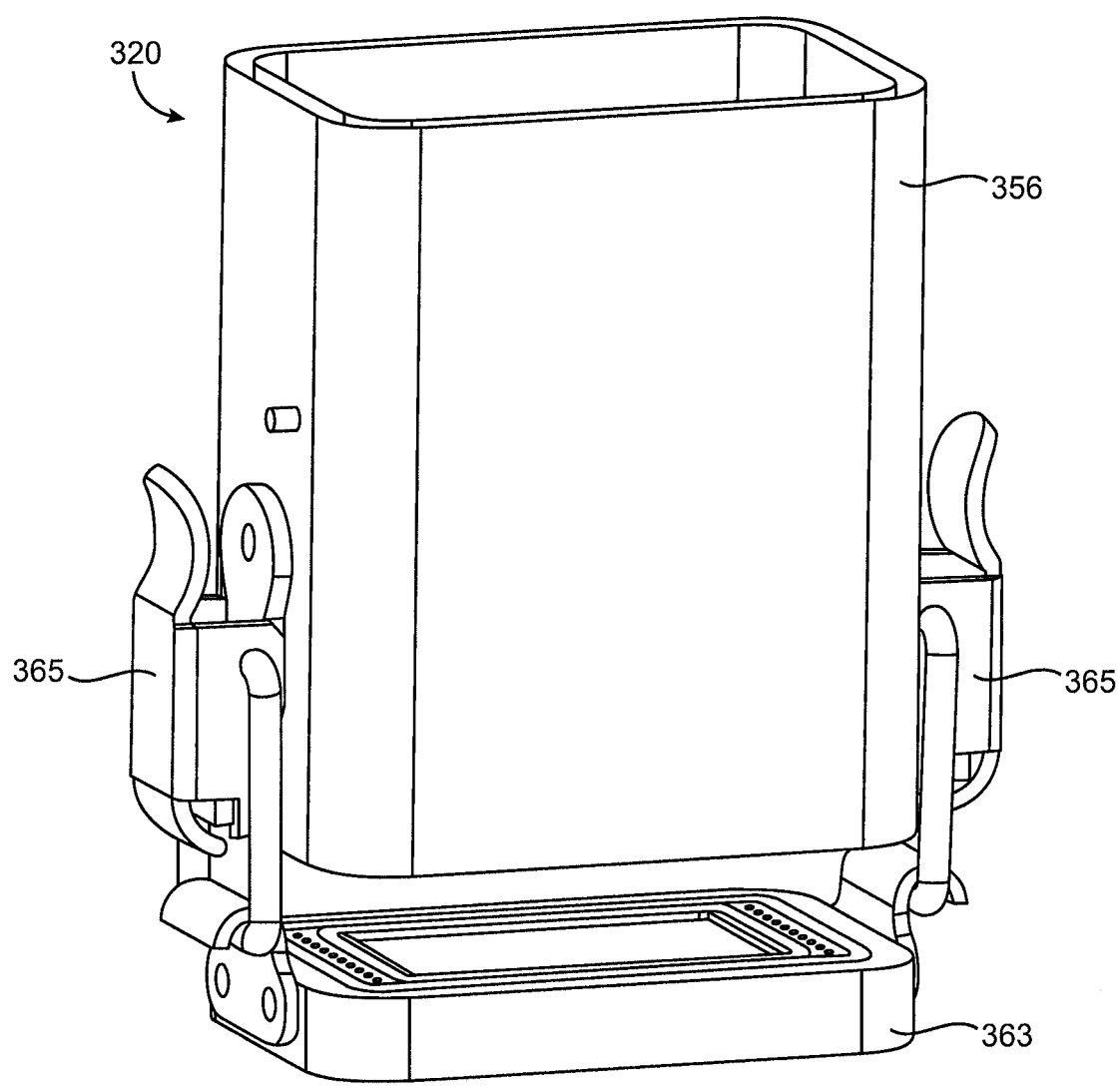
FIG. 25 illustrates a disposable tissue head for use with an applicator according to one embodiment of the invention.

FIG. 24 illustrates a disposable tissue head 363 for use with an applicator 320 according to one embodiment of the invention. In embodiments of the invention disposable tissue head 363 may have all of the elements of tissue head 362. In embodiments of the invention disposable tissue head 363 may include elements of tissue head 362, such as, for example, tissue interface 336, cooling plate 340, tissue chamber 338, or vacuum ports 342. In embodiments of the invention disposable tissue head 363 may include a cooling chamber 360. In embodiments of the invention disposable tissue head 363 may include a standoff 376. In the embodiment of the invention illustrated in FIG. 24 disposable tissue head 363 engages with applicator housing 356, positioning antennas 364 in disposable tissue head 363. FIG. 25 illustrates a disposable tissue head 363 for use with an applicator 320 according to one embodiment of the invention. In the embodiment of the invention illustrated in FIG. 25 disposable tissue head 363 engages with applicator housing 356 and is held in place with latches 365.

Tissue Profiles

FIGS. 26 through 51 illustrate a series of profiles, including, for example, profiles of power deposition, profiles of power loss density, profiles of specific absorption rates or profiles of tissue temperature, according to embodiments of the invention. In embodiments of the present invention, profiles such as for example, profiles of power deposition, profiles of power loss density, profiles of specific absorption rates or profiles of tissue temperature may be referred to as tissue profiles. In the embodiments of the invention illustrated in FIGS. 26 through 51 the illustrated tissue profiles may be representative of, for example, SAR profiles, power loss density profiles or temperature profiles. In some embodiments of the invention, the embodiments and components of embodiments of systems illustrated in FIGS. 2 through 25 as well as, e.g., those illustrated and described at FIGS. 3-7C and pp. 8-13 of U.S. Provisional App. No. 60/912,899; and FIGS. 3-9 and 20-26 and pp. 34-48 and FIGS. 20-26 of U.S. Provisional App. No. 61/013,274 both incorporated by reference in their entireties, as well as illustrated and described in, e.g., FIGS. 3A-7C and pp. 16-20 of Appendix 1 and FIGS. 20-26 and pp. 38-46 of Appendix 2 may be used to generate the tissue profiles illustrated in FIGS. 26 through 51.

FIGS. 26 through 35 illustrate a series of tissue profiles according to embodiments of the invention. In embodiments of the invention illustrated in FIGS. 26 through 35 antenna 358 may be, for example, a simple dipole antenna or a waveguide antenna. In embodiments of the invention illustrated in FIGS. 26 through 35 antenna 358 may be positioned in a medium 1318. In embodiments of the invention illustrated in FIGS. 26 through 35 antenna 358 radiates an electromagnetic signal through medium 1318 and into tissue, generating the patterns illustrated in FIGS. 26 through 35. In one embodiment of the invention, medium 1318 may be, for example, a dielectric material having a dielectric constant (which may also be referred to as permittivity) of approximately 10.

Figure 26:
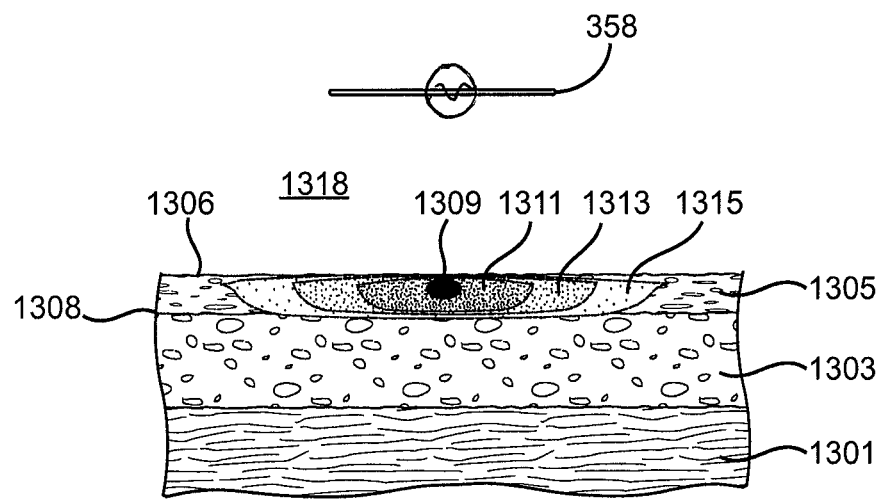
FIG. 26 illustrates a tissue profile according to one embodiment of the invention.
Figure 27:
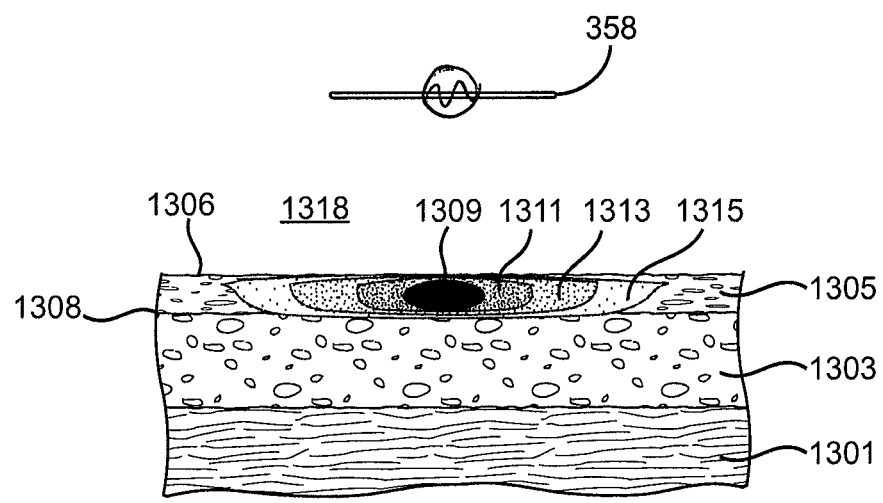
FIG. 27 illustrates a tissue profile according to one embodiment of the invention.
Figure 28:
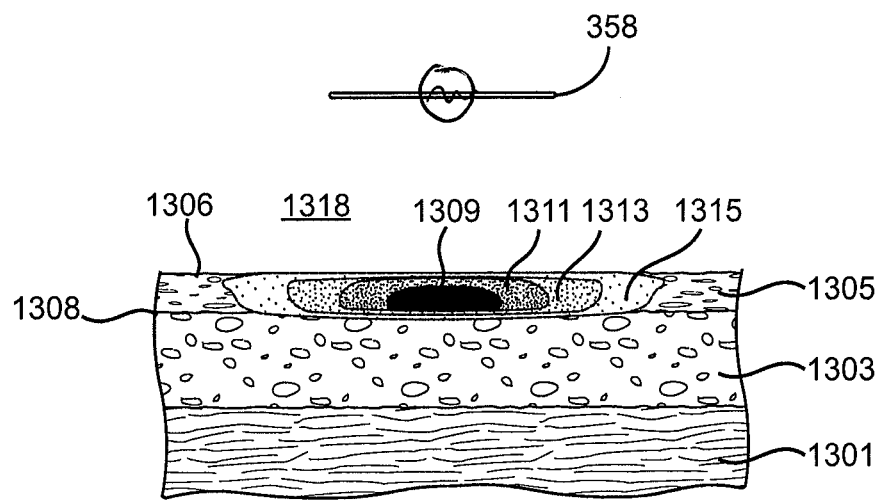
FIG. 28 illustrates a tissue profile according to one embodiment of the invention.
Figure 29:
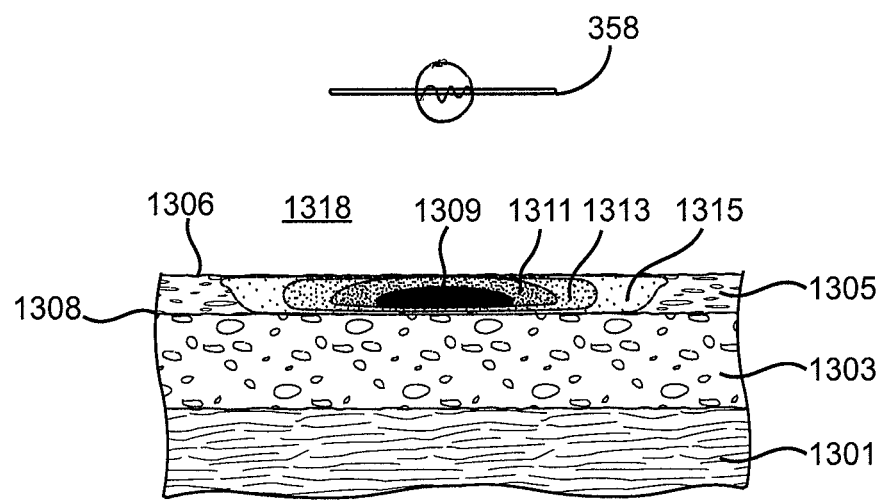
FIG. 29 illustrates a tissue profile according to one embodiment of the invention.
Figure 30:
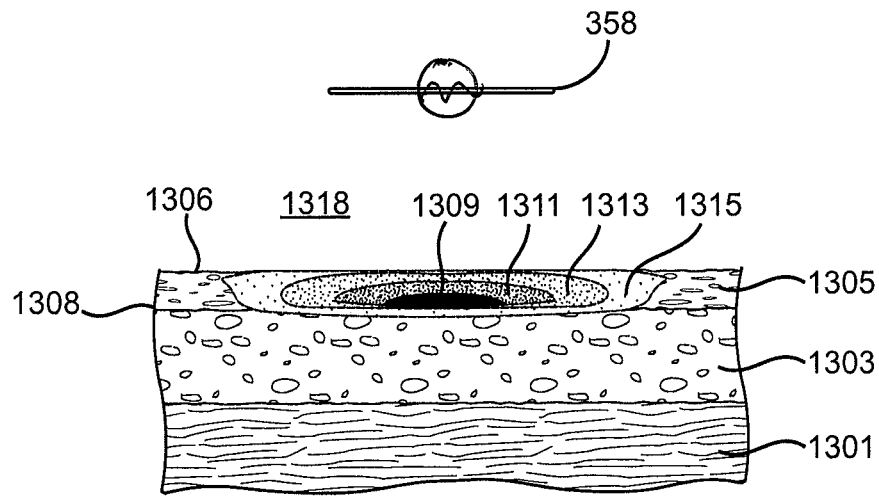
FIG. 30 illustrates a tissue profile according to one embodiment of the invention.
Figure 31:
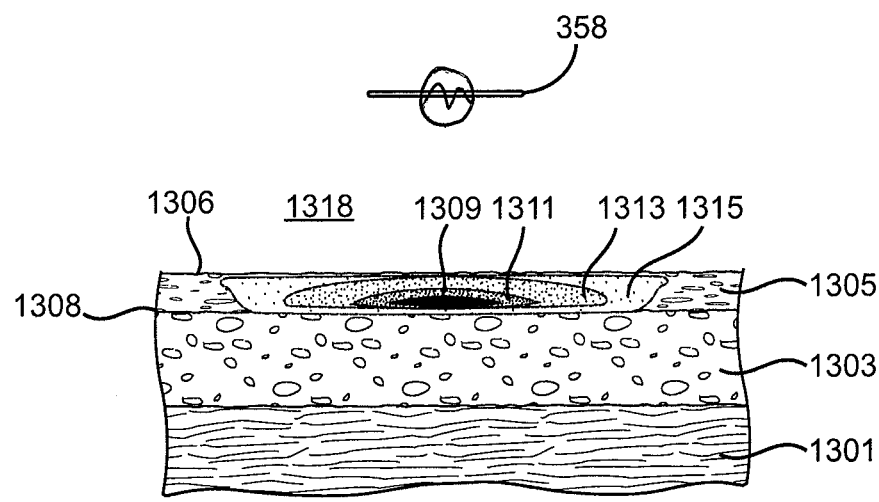
FIG. 31 illustrates a tissue profile according to one embodiment of the invention.
Figure 32:
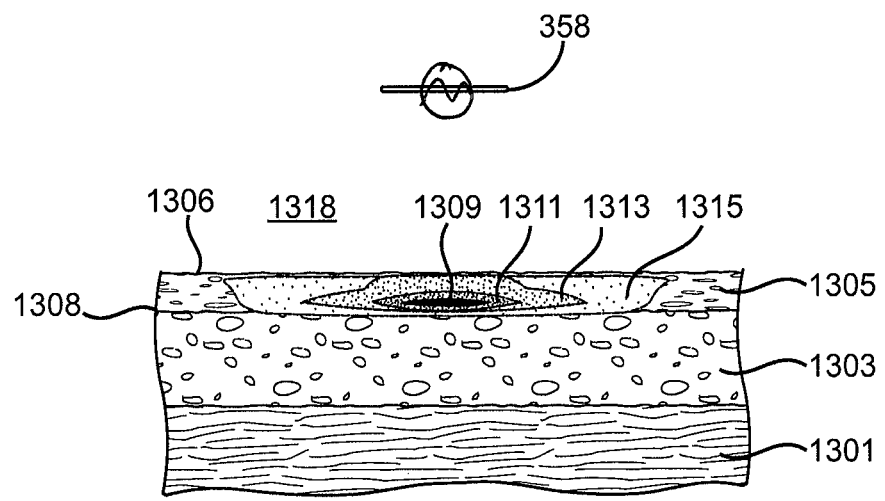
FIG. 32 illustrates a tissue profile according to one embodiment of the invention.
Figure 33:
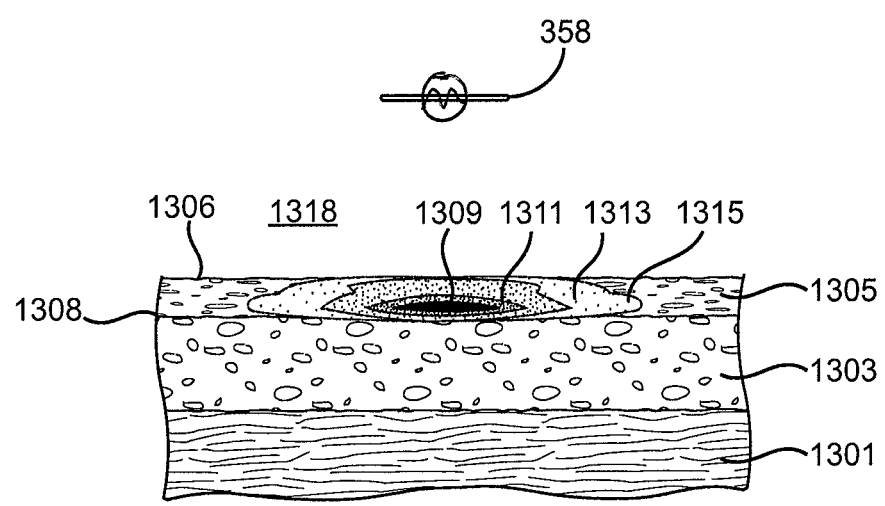
FIG. 33 illustrates a tissue profile according to one embodiment of the invention.

In the embodiment of the invention illustrated in FIG. 26 antenna 358 may radiate energy at a frequency of, for example, approximately 3.0 GHz. In the embodiment of the invention illustrated in FIG. 27 antenna 358 may radiate energy at a frequency of, for example, approximately 3.5 GHz. In the embodiment of the invention illustrated in FIG. 28 antenna 358 may radiate energy at a frequency of, for example, approximately 4.0 GHz. In the embodiment of the invention illustrated in FIG. 29 antenna 358 may radiate energy at a frequency of, for example, approximately 4.5 GHz. In the embodiment of the invention illustrated in FIG. 30 antenna 358 may radiate energy at a frequency of, for example, approximately 5.0 GHz. In the embodiment of the invention illustrated in FIG. 31 antenna 358 may radiate energy at a frequency of, for example, approximately 5.8 GHz. In the embodiment of the invention illustrated in FIG. 32 antenna 358 may radiate energy at a frequency of, for example, approximately 6.5 GHz. In the embodiment of the invention illustrated in FIG. 33 antenna 358 may radiate energy at a frequency of, for example, approximately 7.5 GHz. In the embodiment of the invention illustrated in FIG. 34 antenna 358 may radiate energy at a frequency of, for example, approximately 8.5 GHz. In the embodiment of the invention illustrated in FIG. 35 antenna 358 may radiate energy at a frequency of, for example, approximately 9.0 GHz. In one embodiment of the invention, a tissue profile, such as the profile illustrated in FIGS. 34 and 35 may include at least two constructive interference peaks, where in a first constructive interference peak is positioned in tissue below a second constructive interference peak. In one embodiment of the invention, a tissue profile, such as the profile illustrated in FIGS. 34 and 35 may include at least two constructive interference peaks, where in a second constructive interference peak is positioned near a skin surface.

Figure 34:
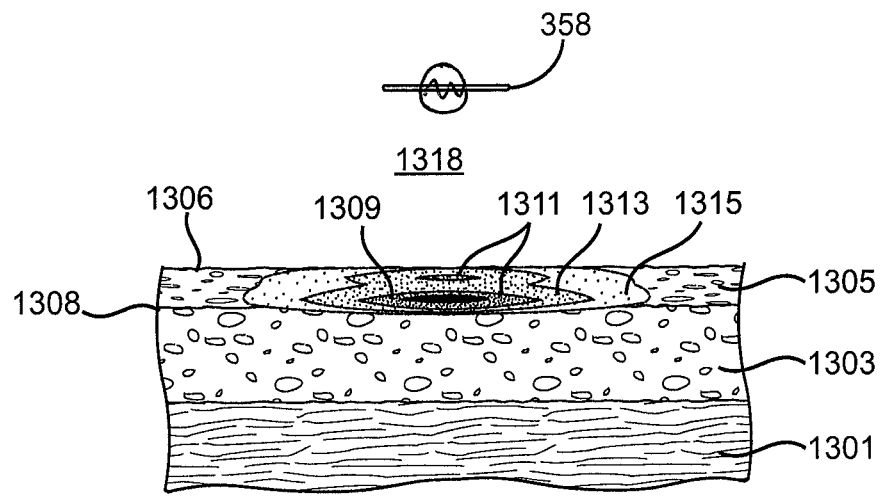
FIG. 34 illustrates a tissue profile according to one embodiment of the invention.
Figure 35:
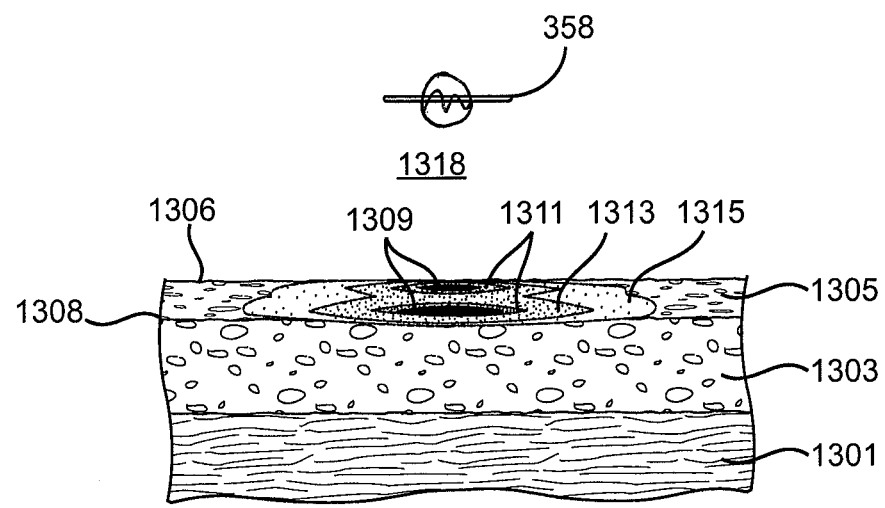
FIG. 35 illustrates a tissue profile according to one embodiment of the invention.
Figure 48:
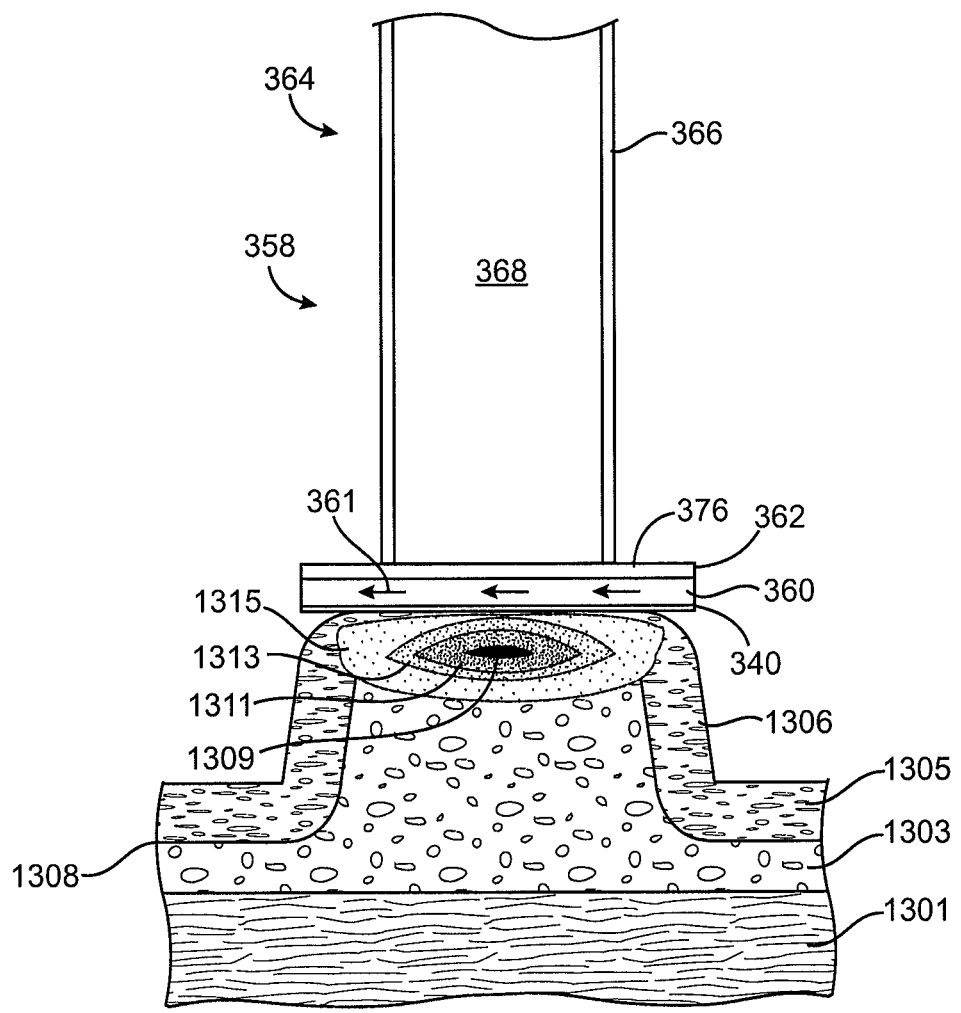
FIG. 48 illustrates a tissue profile according to one embodiment of the invention.

In embodiments of the invention, wherein antenna 358 is representative of a wave guide antenna such as, for example, the waveguide antenna illustrated in FIG. 48 radiating through, for example, at least a portion of a tissue head including a tissue interface, the frequencies at which particular tissue profiles, such as, for example, SAR profiles, power loss profiles or temperature profiles are created may vary from the frequencies at which that such profiles are generated by a dipole antenna. In one embodiment of the invention, a tissue head positioned between a waveguide antenna and a skin surface may comprise, for example, for example, a standoff 376, a cooling chamber 360 filled with cooling fluid 361, such as, for example de-ionized water and a cooling plate 340. In one embodiment of the invention, wherein antenna 358 is a waveguide, antenna 358 may be positioned a distance of approximately 1.5 millimeters from skin surface 1306. In one embodiment of the invention, FIG. 34 illustrates a resulting profile where antenna 358 is a waveguide antenna radiating energy through a tissue head at a frequency of, for example, approximately 10 GHz. In one embodiment of the invention, FIG. 35 illustrates a resulting profile where antenna 358 is a waveguide antenna radiating energy through a tissue head at a frequency of, for example, approximately 12 GHz.

In embodiments of the invention illustrated in FIGS. 26 through 35, antenna 358 may be a dipole antenna and may have a length of, for example, approximately one half wavelength (measured at the operational frequency). In embodiments of the invention illustrated in FIGS. 26 through 35, antenna 358 may be positioned in, for example, a radiating near field region with respect to skin surface 1306. In embodiments of the invention illustrated in FIGS. 26 through 35 antenna 358 may be positioned at a distance of, for example, approximately 10 millimeters from skin surface 1306. In embodiments of the invention illustrated in FIGS. 26 through 30 antenna 358 may be a dipole antenna having an antenna height of, for example, approximately 12 millimeters. In one embodiment of the invention illustrated in FIG. 31 antenna 358 may be a dipole antenna having an antenna height of, for example, approximately 8.5 millimeters. In embodiments of the invention illustrated in FIGS. 32 through 35 antenna 358 may be a dipole antenna having an antenna height of, for example, approximately 7 millimeters.

In embodiments of the invention illustrated in FIGS. 26 through 35 power from antenna 358 is transmitted through skin surface 1306, generating a profile, such as, for example, a SAR profile, a power loss density profile or a temperature profile, in, for example, dermis 1305. In embodiments of the invention illustrated in FIGS. 26 through 35 power transmitted from antenna 358 though skin surface 1306 generates a profile having a peak in first tissue region 1309. In embodiments of the invention illustrated in FIGS. 26 through 35 power transmitted from antenna 358 though skin surface 1306 generates a profile wherein the magnitude decreases from first tissue region 1309 to second tissue region 1311. In embodiments of the invention illustrated in FIGS. 26 through 35 power transmitted from antenna 358 though skin surface 1306 generates a profile wherein the magnitude decreases from second tissue region 1311 to third tissue region 1313. In embodiments of the invention illustrated in FIGS. 26 through 35 power transmitted from antenna 358 though skin surface 1306 generates a profile wherein the magnitude decreases from third tissue region 1313 to fourth tissue region 1315.

In one embodiment of the invention, illustrated in, for example, FIGS. 26 through 39, power transmitted from antenna 358 through skin surface 1306 is at least partially reflected off of interface 1308 such that a peak magnitude of, for example, SAR, power loss density or temperature, is generated in first tissue region 1309 below skin surface 1306. In the embodiment of the invention illustrated in FIG. 26 through 39, interface 1308 may be idealized as a substantially straight line for the purpose of simplified illustration, however, in actual tissue, interface 1308 may be expected to be a non-linear, non continuous, rough interface which may also include tissue structures and groups of tissue structures which cross and interrupt interface 1308. In one embodiment of the invention, a peak magnitude of, for example, SAR, power loss density or temperature is formed as a result of constructive interference between incident and reflected power. In one embodiment of the invention, a peak magnitude of, for example, SAR, power loss density or temperature formed as a result of constructive interference between incident and reflected power is positioned at first tissue region 1309 below a first layer of dermal tissue. In one embodiment of the invention, a minimum magnitude of, for example, SAR, power loss density or temperature is formed as a result of destructive interference between incident and reflected power. In one embodiment of the invention, a minimum magnitude of, for example, SAR, power loss density or temperature formed as a result of destructive interference between incident and reflected power is positioned in a first layer of dermal tissue near skin surface 1306. In one embodiment of the invention, interface 1308 may be, for example, an interface between dermis 1305 and hypodermis 1303. In one embodiment of the invention, first tissue region 1309 may be formed in the lower half of the dermis. In one embodiment of the invention, interface 1308 may be, for example, an interface between a high dielectric, high conductivity tissue layer and a low dielectric, low conductivity tissue layer. In one embodiment of the invention, interface 1308 may be, for example, an interface between a high dielectric, high conductivity tissue layer and a low dielectric tissue layer In one embodiment of the invention, interface 1308 may be, for example, an interface between a glandular layer and a layer of the hypodermis.

In one embodiment of the invention, energy transmitted through skin surface 1306 creates a peak temperature in first region 1309. In one embodiment of the invention, energy transmitted through skin surface 1306 raises a temperature in first region 1309 to a temperature sufficient to induce hyperthermia in tissue in region 1309. In one embodiment of the invention, energy transmitted through skin surface 1306 raises a temperature in first region 1309 to a temperature sufficient to ablate tissue in region 1309. In one embodiment of the invention, energy transmitted through skin surface 1306 raises a temperature in first region 1309 to a temperature sufficient to cause cell death in tissue in region 1309. In one embodiment of the invention, energy transmitted through skin surface 1306 raises a temperature in first region 1309 to a temperature sufficient to form a lesion core in first region 1309. In one embodiment of the invention, energy transmitted through skin surface 1306 raises a temperature in first region 1309 to a temperature sufficient to create a lesion in tissue in region 1309. In one embodiment of the invention, energy transmitted through skin surface 1306 raises the temperature of tissue in region 1309 by dielectric heating. In one embodiment of the invention, energy transmitted through skin surface 1306 preferentially raises the temperature of tissue in region 1309 above the temperature of surrounding regions. In one embodiment of the invention, energy transmitted through skin surface 1306 preferentially raises the temperature of tissue in region 1309 above the temperature of surrounding regions to a temperature sufficient to cause secondary effects, such as, for example the destruction of bacteria in such surrounding regions.

In one embodiment of the invention, energy transmitted through skin surface 1306 generates a temperature in first region 1309 sufficient to heat tissue around first region 1309, by, for example, thermal conductive heating. In one embodiment of the invention, energy transmitted through skin surface 1306 generates a temperature in first region 1309 sufficient to heat tissue structures, such as, for example, sweat glands or hair follicles, in tissue around first region 1309, by, for example, thermal conductive heating. In one embodiment of the invention, energy transmitted through skin surface 1306 generates a temperature in first region 1309 sufficient to cause hyperthermia in tissue around first region 1309, by, for example, thermal conductive heating. In one embodiment of the invention, energy transmitted through skin surface 1306 generates a temperature in first region 1309 sufficient to ablate tissue around first region 1309, by, for example, thermal conductive heating. In one embodiment of the invention, energy transmitted through skin surface 1306 generates a temperature in first region 1309 sufficient to kill bacteria in tissue or tissue structures around first region 1309, by, for example, thermal conductive heating. In one embodiment of the invention, energy transmitted through skin surface 1306 generates a temperature in first region 1309 sufficient to create a lesion in tissue around first region 1309, by, for example, thermal conductive heating. In one embodiment of the invention, energy transmitted through skin surface 1306 generates a temperature in first region 1309 sufficient to expand a lesion into tissue around first region 1309, by, for example, thermal conductive heating.

Near Field

FIGS. 36 through 39 illustrate a series of tissue profiles according to one embodiment of the invention. In the embodiment of the invention illustrated in FIGS. 36 through 39 antenna 358 may be, for example, a simple dipole antenna or a waveguide antenna. In the embodiment of the invention illustrated in FIG. 36 through 39 antenna 358 may be excited at a predetermined frequencies such as, for example, approximately 5.8 GHz. In embodiments of the invention illustrated in FIGS. 36 through 38, antenna 358 may be positioned in, for example, a radiating near field region with respect to skin surface 1306. In an embodiment of the invention illustrated in FIG. 39, antenna 358 may be positioned in, for example, a reactive near field region with respect to skin surface 1306. In embodiments of the invention illustrated in FIGS. 36 through 39 antenna 358 may be positioned at a distance A of, for example, between approximately 10 millimeters and approximately 2 millimeters from skin surface 1306. In embodiments of the invention illustrated in FIGS. 36 through 39 antenna 358 may be positioned in a medium 1318. In embodiments of the invention illustrated in FIGS. 36 through 39 antenna 358 may be a dipole antenna having an antenna height of approximately 8.5 millimeters. In the embodiments of the invention illustrated in FIGS. 36 through 39 antenna 358 may radiate energy at a frequency of, for example, approximately 5.8 GHz.

In embodiments of the invention illustrated in FIGS. 36 through 39 power from antenna 358 is transmitted through skin surface 1306, generating a tissue profile in dermis 1305. In embodiments of the invention illustrated in FIGS. 36 through 39 power transmitted from antenna 358 though skin surface 1306 generates a tissue profile having a peak in first tissue region 1309. In embodiments of the invention illustrated in FIGS. 36 through 39 power transmitted from antenna 358 though skin surface 1306 generates a tissue profile which may represent, for example, SAR, power loss density or temperature. In embodiments of the invention illustrated in FIGS. 36 through 39 power transmitted from antenna 358 though skin surface 1306 generates a tissue profile wherein the magnitude of, for example, SAR, power loss density or temperature, decreases from first tissue region 1309 to second tissue region 1311, from second tissue region 1311 to third tissue region 1313 and from third tissue region 1313 to fourth tissue region 1315.

In one embodiment of the invention, illustrated in, for example, FIG. 36, power transmitted from antenna 358 through skin surface 1306 is at least partially reflected off of interface 1308 such that a peak of, for example, SAR, power loss density or temperature, is generated in first tissue region 1309 below skin surface 1306. In one embodiment of the invention illustrated in, for example, FIG. 36, a peak of, for example, SAR, power loss density or temperature formed as a result of constructive interference between incident and reflected power is positioned at first tissue region 1309 below a first layer of dermal tissue. In one embodiment of the invention illustrated in, for example, FIG. 36, a peak of, for example, SAR, power loss density or temperature formed as a result of constructive interference between incident and reflected power is positioned at first tissue region 1309 in a lower half of dermis 1305. In one embodiment of the invention illustrated in FIG. 36 antenna 358 may be positioned at a distance A of, for example, approximately 10 millimeters from skin surface 1306. In one embodiment of the invention illustrated in FIG. 37 antenna 358 may be positioned at a distance A of, for example, approximately 5 millimeters from skin surface 1306. In one embodiment of the invention illustrated in FIG. 38 antenna 358 may be positioned at a distance A of, for example, approximately 3 millimeters from skin surface 1306. In one embodiment of the invention illustrated in FIG. 39 antenna 358 may be positioned at a distance A of, for example, approximately 2 millimeters from skin surface 1306. In one embodiment of the invention illustrated in FIGS. 36 through 38, tissue in region 1309 is preferentially heated with respect to tissue in layers above first tissue region 1309.

Figure 36:
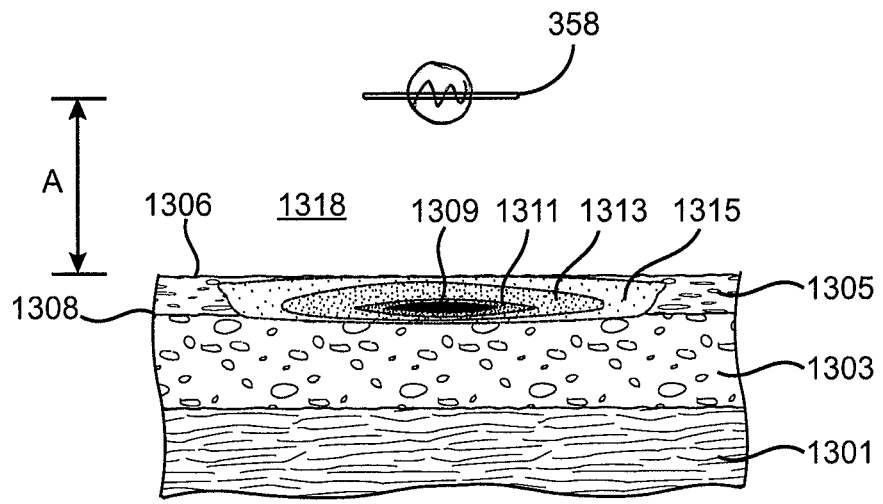
FIG. 36 illustrates a tissue profile according to one embodiment of the invention.
Figure 37:
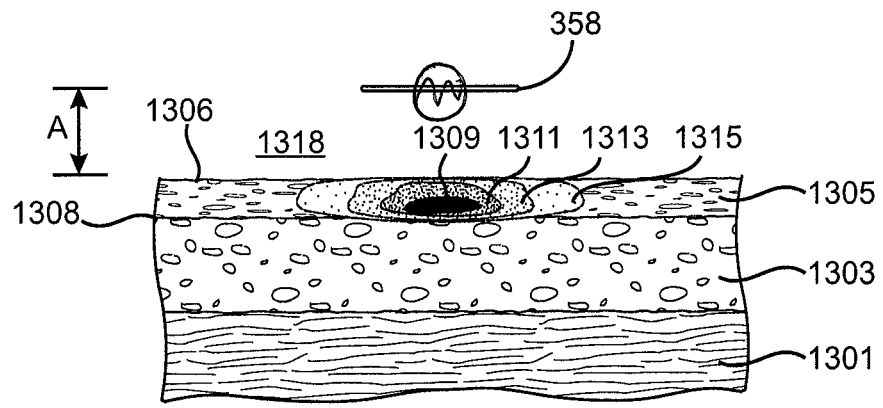
FIG. 37 illustrates a tissue profile according to one embodiment of the invention.
Figure 38:
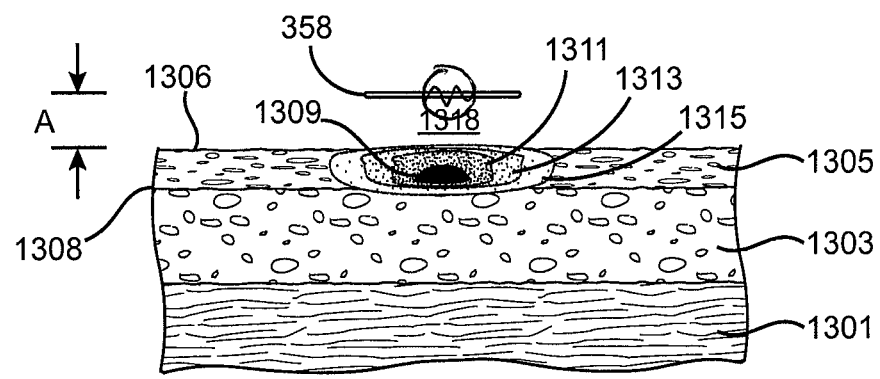
FIG. 38 illustrates a tissue profile according to one embodiment of the invention.
Figure 39:
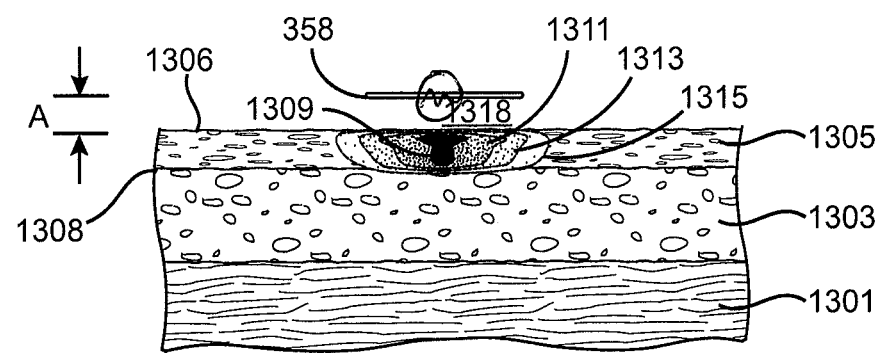
FIG. 39 illustrates a tissue profile according to one embodiment of the invention.

In one embodiment of the invention illustrated in FIG. 36 antenna 358 may be positioned at a distance A within a radiating near field of skin surface 1306. In one embodiment of the invention illustrated in FIG. 37 antenna 358 may be positioned at a distance A within a radiating near field of skin surface 1306. In one embodiment of the invention illustrated in FIG. 38 antenna 358 may be positioned at a distance A within a radiating near field of skin surface 1306. In one embodiment of the invention illustrated in FIG. 39 antenna 358 may be positioned at a distance A within a reactive near field of skin surface 1306. As illustrated in FIG. 39, in one embodiment of the invention, positioning an antenna in a reactive near field results in substantial reactive coupling, which increases power deposition at the upper skin layer and destroys the preferential heating profiles illustrated in FIGS. 36 thorough 38. In one embodiment of the invention, a reactive near field may be that distance which results in substantial reactive coupling between an antenna and adjacent tissue, increasing power deposition at the upper skin layer and destroying the preferential heating profiles illustrated in FIGS. 36 thorough 38

Preferential Heating—Dermis

FIGS. 40 through 43 illustrate tissue profiles according to one embodiment of the invention. In embodiments of the invention illustrated in FIGS. 40 through 43 dermis 1305 and hypodermis 1303 may contain tissue structures 1325 which may be, for example, sweat glands, including, for example, eccrine glands, apocrine glands or apoeccrine glands. In embodiments of the invention illustrated in FIGS. 40 through 43 dermis 1305 and hypodermis 1303 may contain tissue structures 1325 which may be, for example, sweat glands, including, for example, eccrine glands, apocrine glands or apoeccrine glands. In embodiments of the invention illustrated in FIGS. 40 through 43 dermis 1305 and hypodermis 1303 may contain tissue structures 1325 which may be, for example, hair follicles. In embodiments of the invention illustrated in FIGS. 40 through 43 tissue structures 1325 may include ducts 1329 extending from tissue structures 1325 to skin surface 1306. In embodiments of the invention, tissue structures 1325 include groups of tissue structures 1325.

Figure 40:
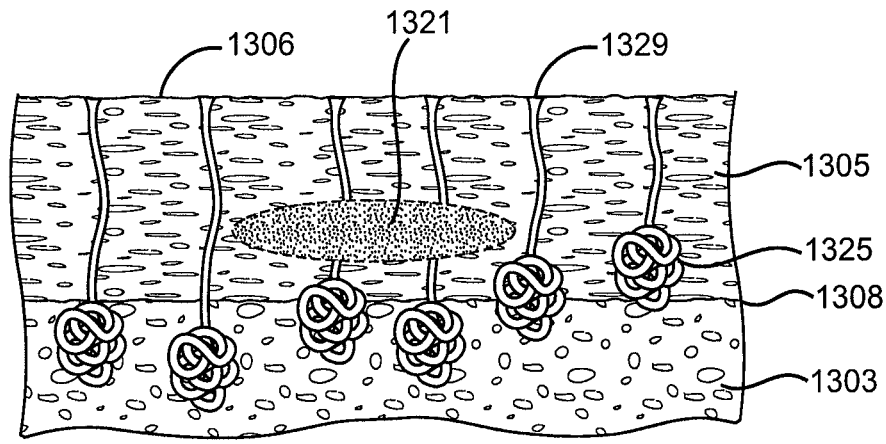
FIG. 40 illustrates a tissue profile according to one embodiment of the invention.

FIG. 40 illustrates a tissue profile according to one embodiment of the invention. In the embodiment of the invention illustrated in FIG. 40 a lesion core 1321 is created in a predetermined portion of dermis 1305 by, for example, irradiating dermis 1305 with electromagnetic radiation to generate dielectric heating in tissue at lesion core 1321. In one embodiment of the invention, lesion core 1321 may be, for example, a point or region within a tissue layer where a lesion starts to grow. In the embodiment of the invention illustrated in FIG. 40 lesion core 1321 is created by heat generated in dermal tissue by dielectric heating of lesion core 1321. In the embodiment of the invention illustrated in FIG. 40 lesion core 1321 expands as energy is added to dermis 1305. In the embodiment of the invention illustrated in FIG. 40 lesion core 1321 may be located in a region of dermis 1305 where a constructive interference peak is generated by electromagnetic energy transmitted through skin surface 1306. In the embodiment of the invention illustrated in FIG. 40 lesion core 1321 may be located in a region of dermis 1305 where a constructive interference peak is generated by electromagnetic energy transmitted through skin surface wherein at least a portion of the electromagnetic energy transmitted through skin surface 1306 reflects off of interface 1308 which may be, for example, an interface between high dielectric, high conductivity tissue and low dielectric, low conductivity tissue. In the embodiment of the invention illustrated in FIG. 40 lesion core 1321 may be located in a region of dermis 1305 where a constructive interference peak is generated by electromagnetic energy transmitted through skin surface 1306 wherein at least a portion of the electromagnetic energy transmitted through skin surface 1306 reflects off of interface 1308 which may be, for example, an interface between high dielectric, high conductivity tissue and low dielectric tissue. In the embodiment of the invention illustrated in FIG. 40 interface may be idealized as a substantially straight line for the purpose of simplified illustration, however, in actual tissue, interface 1308 may be a non-linear, non continuous, rough interface which may also include many tissue structures and groups of tissue structures which cross and interrupt the tissue interface. In the embodiment of the invention illustrated in FIG. 40 lesion core 1321 may be located in a region of dermis 1305 where a constructive interference peak is generated by electromagnetic energy transmitted through skin surface wherein at least a portion of the electromagnetic energy transmitted through skin surface 1306 reflects off of interface 1308 which may be, for example, an interface between dermis 1305 and hypodermis 1303.

Figure 41:
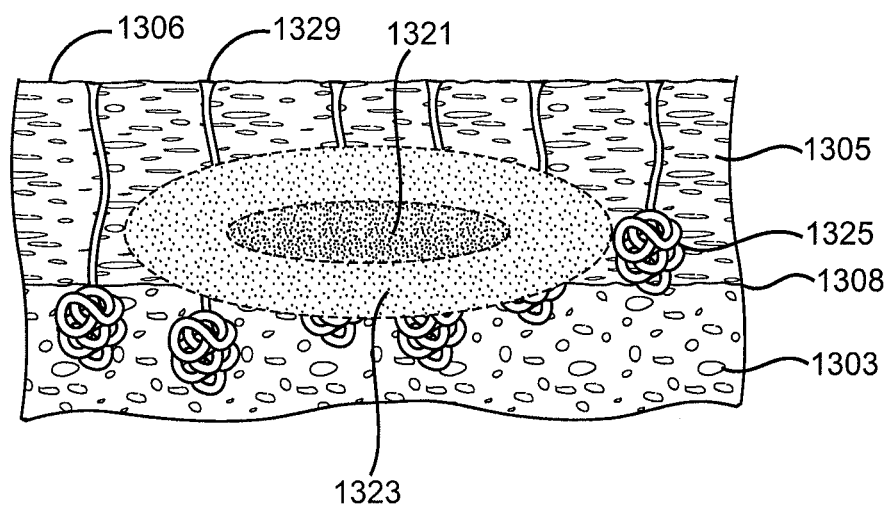
FIG. 41 illustrates a tissue profile according to one embodiment of the invention.

FIG. 41 illustrates a tissue profile according to one embodiment of the invention. In the embodiment of the invention illustrated in FIG. 41 lesion core 1321 expands as energy is added to dermis 1305, generating heat which is conducted into surrounding tissue creating expanded lesion

1323. In the embodiment of the invention illustrated in FIG. 41 heat conducted from lesion core 1321 into expanded lesion 1323 damages tissue, including tissue structures 1325 outside lesion 1321. In the embodiment of the invention illustrated in FIG. 41 heat conducted from lesion core 1321 into expanded lesion 1323 crosses interface 1308 and damages tissue below interface 1308, including tissue structures 1325 outside and below lesion core 1321.

Figure 42:
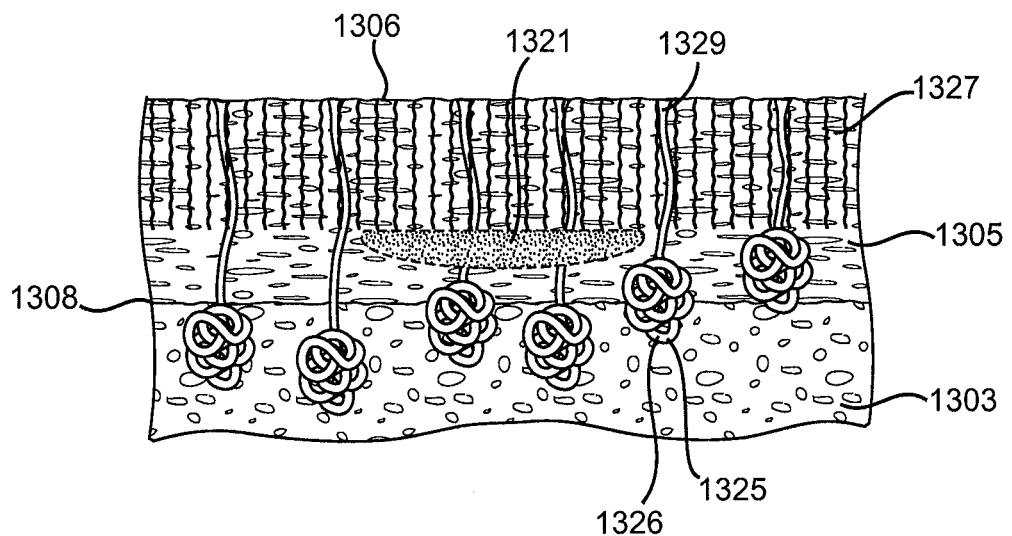
FIG. 42 illustrates a tissue profile according to one embodiment of the invention.

FIG. 42 illustrates a tissue profile according to one embodiment of the invention. In the embodiment of the invention illustrated in FIG. 42 a lesion core 1321 is created in a predetermined portion of dermis 1305 by, for example, irradiating dermis 1305 with electromagnetic radiation to generate dielectric heating in tissue at lesion core 1321. In the embodiment of the invention illustrated in FIG. 42 lesion core 1321 expands as energy is added to dermis 1305. In the embodiment of the invention illustrated in FIG. 42 heat is removed from skin surface 1306. In the embodiment of the invention illustrated in FIG. 42 heat is removed from dermis 1305 through skin surface 1306. In the embodiment of the invention illustrated in FIG. 42 heat is removed from dermis 1305 through skin surface 1306 by cooling skin surface 1306. In the embodiment of the invention illustrated in FIG. 42 heat removed from dermis 1305 through skin surface 1306 prevents lesion core 1321 and expanded lesion 1323 from growing in the direction of skin surface 1306. In the embodiment of the invention illustrated in FIG. 42 removed from dermis 1305 through skin surface 1306 prevents lesion core 1321 and expanded lesion 1323 from growing into cooled region 1327.

Figure 43:
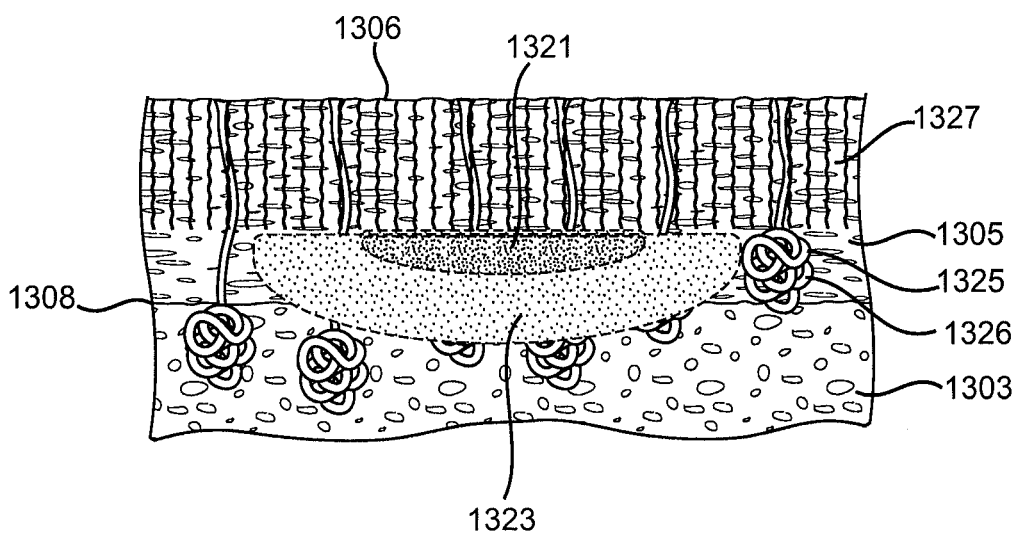
FIG. 43 illustrates a tissue profile according to one embodiment of the invention.

FIG. 43 illustrates a tissue profile according to one embodiment of the invention. In the embodiment of the invention illustrated in FIG. 43 a lesion core 1321 is created in a predetermined portion of dermis 1305 by, for example, irradiating dermis 1305 with electromagnetic radiation to generate dielectric heating in tissue at lesion core 1321 and expanded lesion 1323 is created by heat conducted from lesion core 1321. In the embodiment of the invention illustrated in FIG. 43 lesion core 1321 expands as energy is added to dermis 1305 and expanded lesion 1323 expands as heat is conducted from lesion core 1321. In the embodiment of the invention illustrated in FIG. 43 heat is removed from skin surface 1306. In the embodiment of the invention illustrated in FIG. 43 heat is removed from dermis 1305 through skin surface 1306. In the embodiment of the invention illustrated in FIG. 43 heat is removed from dermis 1305 through skin surface 1306 by cooling skin surface 1306. In the embodiment of the invention illustrated in FIG. 43 heat removed from dermis 1305 through skin surface 1306 prevents lesion core 1321 and expanded lesion 1323 from growing in the direction of skin surface 1306. In the embodiment of the invention illustrated in FIG. 43 removed from dermis 1305 through skin surface 1306 prevents lesion core 1321 and expanded lesion 1323 from growing into cooled region 1327.

Preferential Heating—Glandular Layer

FIGS. 44 through 47 illustrate tissue profiles according to embodiments of the invention. In embodiments of the invention illustrated in FIGS. 44 through 47 dermis 1305 and hypodermis 1303 may contain tissue structures 1325 which may be, for example, sweat glands, including, for example, eccrine glands, apocrine glands or apoeccrine glands. In embodiments of the invention illustrated in FIGS. 44 through 47 dermis 1305 and hypodermis 1303 may contain tissue structures 1325 which may be, for example, sweat glands, including, for example, eccrine glands, apocrine glands or apoeccrine glands. In embodiments of the invention illustrated in FIGS. 44 through 47 dermis 1305 and hypodermis 1303 may contain tissue structures 1325 which may be, for example, hair follicles. In embodiments of the invention illustrated in FIGS. 44 through 47 tissue structures 1325 may include ducts 1329 extending from tissue structures 1325 to skin surface 1306. In embodiments of the invention illustrated in FIGS. 44 through 47 tissue structures 1325 may be concentrated in a glandular layer 1331. In embodiments of the invention illustrated in FIGS. 44 through 47 tissue structures 1325 may be concentrated in a glandular layer 1331 wherein glandular layer 1331 has an upper interface 1335 and a lower interface 1333. In embodiments of the invention illustrated in FIGS. 44 through 47 glandular layer 1331 may have an upper interface 1335 between glandular layer 1331 and dermis 1305. In embodiments of the invention illustrated in FIGS. 44 through 47 glandular layer 1331 may have a lower interface 1333 between glandular layer 1331 and hypodermis 1303. In the embodiment of the invention illustrated in FIGS. 44 through 47 interface 1333 may be, in actual tissue a non-linear, non continuous, rough interface which may also include many tissue structures and groups of tissue structures and groups of tissue structures which add to the roughness and nonlinearity of tissue interface 1333.

In embodiments of the invention illustrated in FIGS. 44 through 47 tissue structures 1325 may be composed, at least in part of high dielectric/high conductivity tissue such as, for example, sweat glands. In embodiments of the invention illustrated in FIGS. 44 through 47 tissue structures 1325 may be composed, at least in part of tissue having a high water content, such as, for example, sweat glands. In embodiments of the invention illustrated in FIGS. 44 through 47 glandular layer 1331 may be composed, at least in part of high dielectric/high conductivity tissue. In embodiments of the invention illustrated in FIGS. 44 through 47 glandular layer 1331 may have an upper interface 1335 between glandular layer 1331 and high dielectric/high conductivity tissue, such as, for example, dermis 1305. In embodiments of the invention illustrated in FIGS. 44 through 47 glandular layer 1331 may have a lower interface 1333 between glandular layer 1331 and low dielectric/low conductivity tissue, such as, for example, hypodermis 1303. In embodiments of the invention illustrated in FIGS. 44 through 47 glandular layer 1331 may have a lower interface 1333 between glandular layer 1331 and low dielectric tissue.

Figure 44:
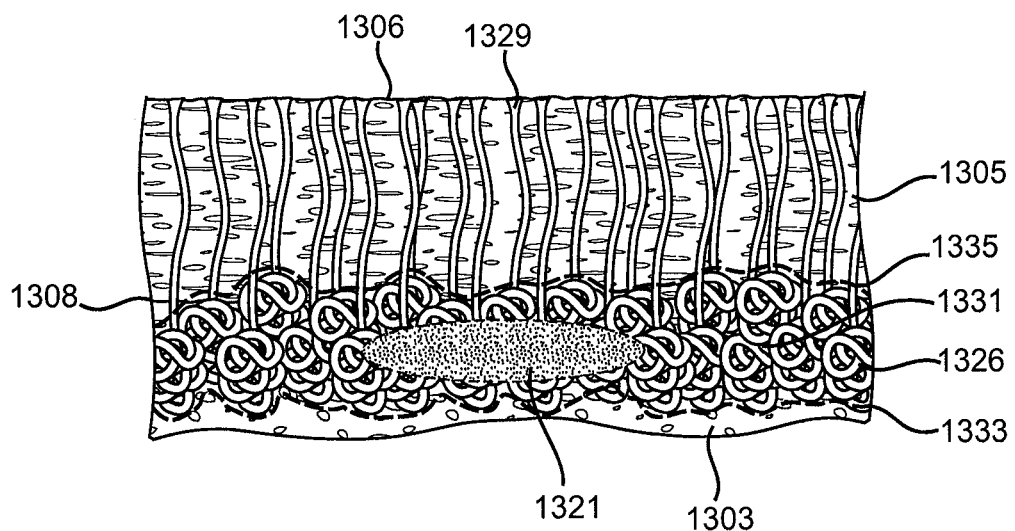
FIG. 44 illustrates a tissue profile according to one embodiment of the invention.

FIG. 44 illustrates a tissue profile according to one embodiment of the invention. In the embodiment of the invention illustrated in FIG. 44 a lesion core 1321 is created in a predetermined portion of glandular layer 1331 by, for example, irradiating glandular layer 1331 with electromagnetic radiation to generate dielectric heating in tissue at lesion core 1321. In the embodiment of the invention illustrated in FIG. 44 lesion core 1321 is created by heat generated in glandular layer 1331 by dielectric heating of lesion core 1321. In the embodiment of the invention illustrated in FIG. 44 lesion core 1321 expands as energy is added to glandular layer 1331. In the embodiment of the invention illustrated in FIG. 44 lesion core 1321 may be located in a region of glandular layer 1331 where a constructive interference peak of, for example, SAR, power loss density or temperature, is generated by electromagnetic energy transmitted through skin surface 1306. In the embodiment of the invention illustrated in FIG. 44 lesion core 1321 may be located in a region of glandular layer 1331 where a constructive interference peak of, for example, SAR, power loss density or temperature, is generated by electromagnetic energy transmitted through skin surface 1306 wherein at least a portion of the electromagnetic energy transmitted through skin surface 1306 reflects off of lower interface 1333. In the embodiment of the invention illustrated in FIG. 44 lesion core 1321 may be located in a region of glandular layer 1331 where a constructive interference peak of, for example, SAR, power loss density or temperature, is generated by electromagnetic energy transmitted through skin surface 1306 wherein at least a portion of the electromagnetic energy transmitted through skin surface 1306 reflects off of lower interface 1333 which may be, for example, an interface between glandular layer 1331 and hypodermis 1303.

Figure 45:
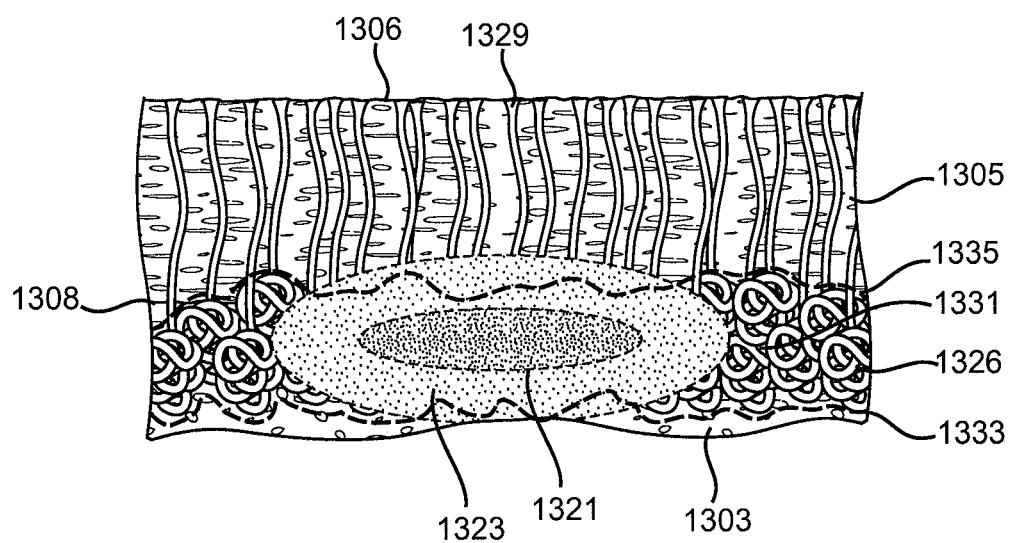
FIG. 45 illustrates a tissue profile according to one embodiment of the invention.

FIG. 45 illustrates a tissue profile according to one embodiment of the invention. In the embodiment of the invention illustrated in FIG. 45 lesion core 1321 expands as energy is added to glandular layer 1331, generating heat which is conducted into surrounding tissue, creating expanded lesion 1323. In the embodiment of the invention illustrated in FIG. 45 heat conducted from lesion core 1321 into expanded lesion 1323 damages tissue, including tissue structures 1325 out side lesion core 1321. In the embodiment of the invention illustrated in FIG. 45 heat conducted from lesion core 1321 into expanded lesion 1323 crosses lower interface 1333 and damages tissue below lower interface 1333 and outside lesion core 1321.

Figure 46:
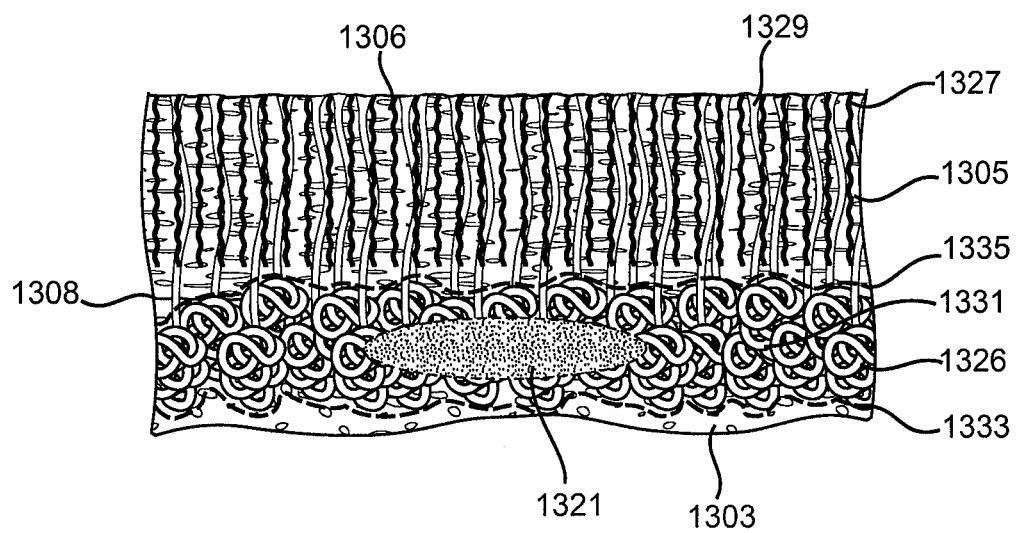
FIG. 46 illustrates a tissue profile according to one embodiment of the invention.
Figure 47:
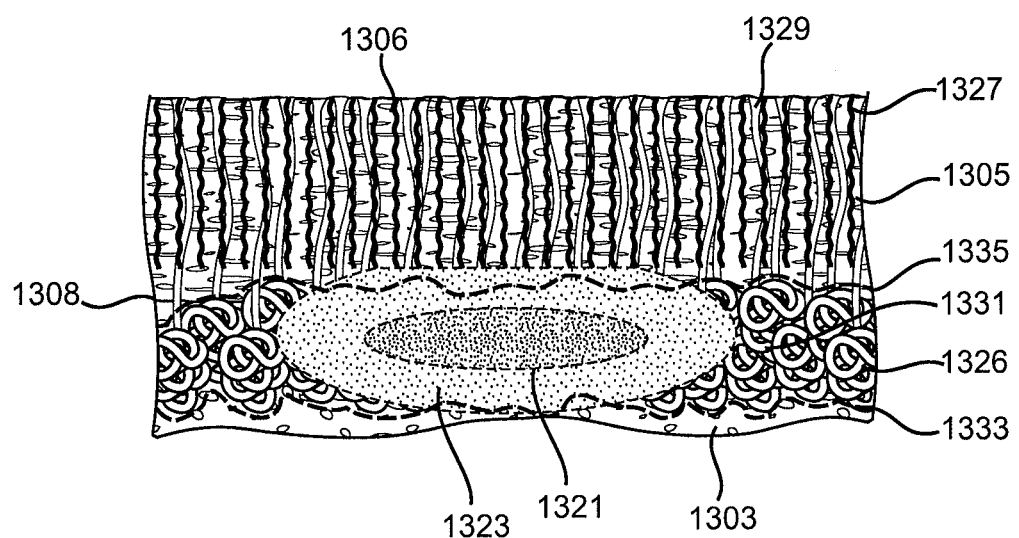
FIG. 47 illustrates a tissue profile according to one embodiment of the invention.

FIGS. 46 and 47 illustrate tissue profiles according to one embodiment of the invention. In the embodiment of the invention illustrated in FIGS. 46 and 47 a lesion core 1321 is created in a portion of glandular layer 1331 by, for example, irradiating glandular layer 1331 with electromagnetic radiation to generate dielectric heating in tissue at lesion core 1321. In the embodiments of the invention illustrated in FIGS. 46 and 47 lesion core 1321 expands as energy is added to glandular layer 1331 and expanded lesion 1323 is created by heat conducted from lesion core 1323. In the embodiments of the invention illustrated in FIGS. 46 and 47 heat is removed from skin surface 1306. In the embodiments of the invention illustrated in FIGS. 46 and 47 heat is removed from dermal layer 1305 through skin surface 1306. In the embodiments of the invention illustrated in FIGS. 46 and 47 heat is removed from dermal layer 1305 through skin surface 1306 by cooling skin surface 1306, creating cooled region 1307 in dermis 1305. In the embodiment of the invention illustrated in FIG. 47 heat removed from dermal layer 1305 through skin surface 1306 prevents expanded lesion 1323 from growing in the direction of skin surface 1306. In the embodiment of the invention illustrated in FIG. 46 heat removed from glandular layer 1331 through skin surface 1306 prevents expanded lesion 1323 from growing into cooled region 1327.

FIGS. 48 through 51 illustrate tissue profiles and apparatuses according to embodiments of the invention. In FIGS. 48 through 51, antenna 358 may be, for example, waveguide antenna 364. In the embodiment of the invention illustrated in FIGS. 48 and 49, waveguide antenna 364 may include, for example, waveguide tubing 366 and dielectric filler 368. In the embodiment of the invention illustrated in FIGS. 48 and 49 electromagnetic energy may be radiated into dermis 1305 through a tissue head 362 which may include, for example, standoff 376, coolant chamber 360 and cooling plate 340. In the embodiment of the invention illustrated in FIG. 48 a peak which may be, for example, a peak SAR, peak power loss density or peak temperature, is generated in first tissue region 1309. In the embodiment of the invention illustrated in FIG. 48 a reduced magnitude which may be, for example, a reduced SAR, reduced power loss density or reduced temperature, is generated in second tissue region 1311 with further reduced magnitudes in third tissue region 1313 and fourth tissue region 1315. In the embodiment of the invention illustrated in FIG. 48 dermis 1305 is separated from hypodermis 1303 by interface 1308. In the embodiment of the invention illustrated in FIG. 48 interface 1308 may be idealized as a substantially straight line for the purposes of simplified illustration, however, in actual tissue, interface 1308 may be a non-linear, non continuous, rough interface which may also include many tissue structures and groups of tissue structures which cross and interrupt the tissue interface. In the embodiment of the invention illustrated in FIG. 48 hypodermis 1303 lies over muscle tissue 1301. In the embodiment of the invention illustrated in FIG. 48 electromagnetic radiation may be radiated at a frequency of, for example, between 5 and 6.5 GHz. In the embodiment of the invention illustrated in FIG. 48 electromagnetic radiation may be radiated at a frequency of, for example, approximately 5.8 GHz. In the embodiment of the invention illustrated in FIG. 48 dermis 1305 may be assumed have a dielectric constant of, for example, approximately 38 and a conductivity of, for example, approximately 4.5 siemens per meter. In the embodiment of the invention illustrated in FIG. 48 hypodermis 1303 may be assumed to have a dielectric constant of, for example, approximately 5 and a conductivity of, for example, approximately 0.31 siemens per meter. In the embodiment of the invention illustrated in FIG. 48 muscle tissue 1301 may be assumed to have a dielectric constant of, for example, approximately 42 and a conductivity of, for example, approximately 5.2 siemens per meter. In the embodiment of the invention illustrated in FIG. 48 standoff 376 may be, for example, polycarbonate and may have a dielectric constant of, for example, approximately 3.4 and a conductivity of, for example, approximately 0.0051 siemens per meter. In the embodiment of the invention illustrated in FIG. 48 cooling plate 340 may be, for example, alumina (99.5%) and may have a dielectric constant of, for example, approximately 9.9 and a conductivity of, for example, approximately $3 \times 10^{-4}$ siemens per meter. In the embodiment of the invention illustrated in FIG. 48 cooling fluid 361 may be, for example, de-ionized water and may have, for example, a dielectric constant of, for example, approximately 81 and a conductivity of, for example, approximately 0.0001 siemens per meter.

Figure 49:
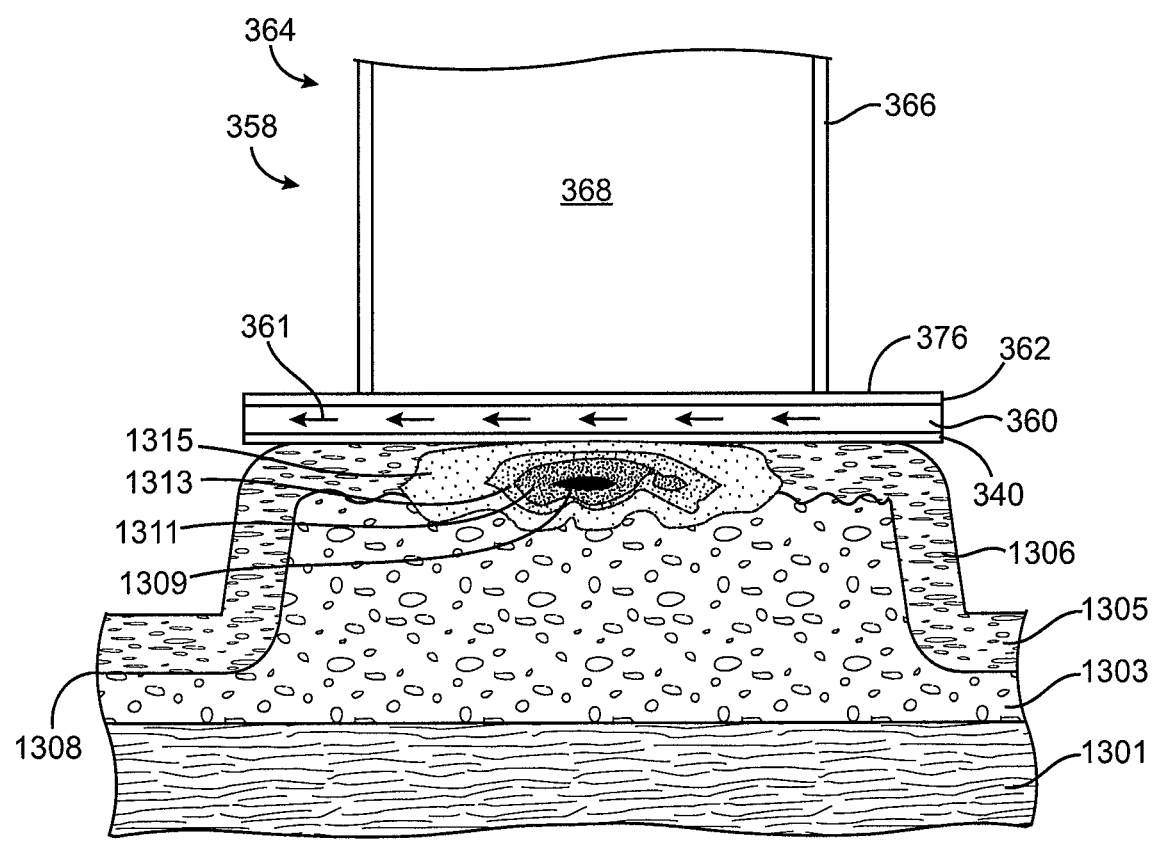
FIG. 49 illustrates a tissue profile according to one embodiment of the invention.

In the embodiment of the invention illustrated in FIG. 49 a peak, which may be, for example, a peak SAR, peak power loss density or peak temperature, is generated in first tissue region 1309. In the embodiment of the invention illustrated in FIG. 48 a reduced magnitude which may be, for example, a reduced SAR, reduced power loss density or reduced temperature, is generated in second tissue region 1311 with further reduced magnitudes in third tissue region 1313 and fourth tissue region 1315. In the embodiment of the invention illustrated in FIG. 49 dermis 1305 is separated from hypodermis 1303 by interface 1308. In the embodiment of the invention illustrated in FIG. 49 interface 1308 may be modeled as a nonlinear interface, to more closely resemble an actual interface between dermal and hypodermal tissue. In the embodiment of the invention illustrated in FIG. 49 hypodermis 1303 lies over muscle tissue 1301. In the embodiment of the invention illustrated in FIG. 49 electromagnetic radiation may be radiated at a frequency of, for example, 5.8 GHz. In the embodiment of the invention illustrated in FIG. 49 dermis 1305 may be assumed to have a dielectric constant of, for example, 38.4 and a conductivity of, for example 4.54 siemens per meter. In the embodiment of the invention illustrated in FIG. 49 hypodermis 1303 may be assumed to have, for example, a dielectric constant of, example, 4.9 and a conductivity of, for example, 0.31 siemens per meter. In the embodiment of the invention illustrated in FIG. 49 muscle tissue 1301 may be assumed to have, for example, a dielectric constant of, for example, 42.22 and a conductivity of, for example, 5.2 siemens per meter. In the embodiment of the invention illustrated in FIG. 49 standoff 376 may be, for example, polycarbonate and may have, for example, a dielectric constant of, for example, 3.4 and a conductivity of, for example, 0.0051 siemens per meter. In the embodiment of the invention illustrated in FIG. 49 cooling plate 340 may be, for example, alumina (99.5%) and may have, for example, a dielectric constant of, for example, 9.9 and a conductivity of, for example, $3 \times 10^{-4}$ siemens per meter. In the embodiment of the invention illustrated in FIG. 49 cooling fluid 361 may be, for example, de-ionized water and may have, for example, a dielectric constant of, for example, 81 and a conductivity of, for example, 0.0001 siemens per meter.

Figure 50:
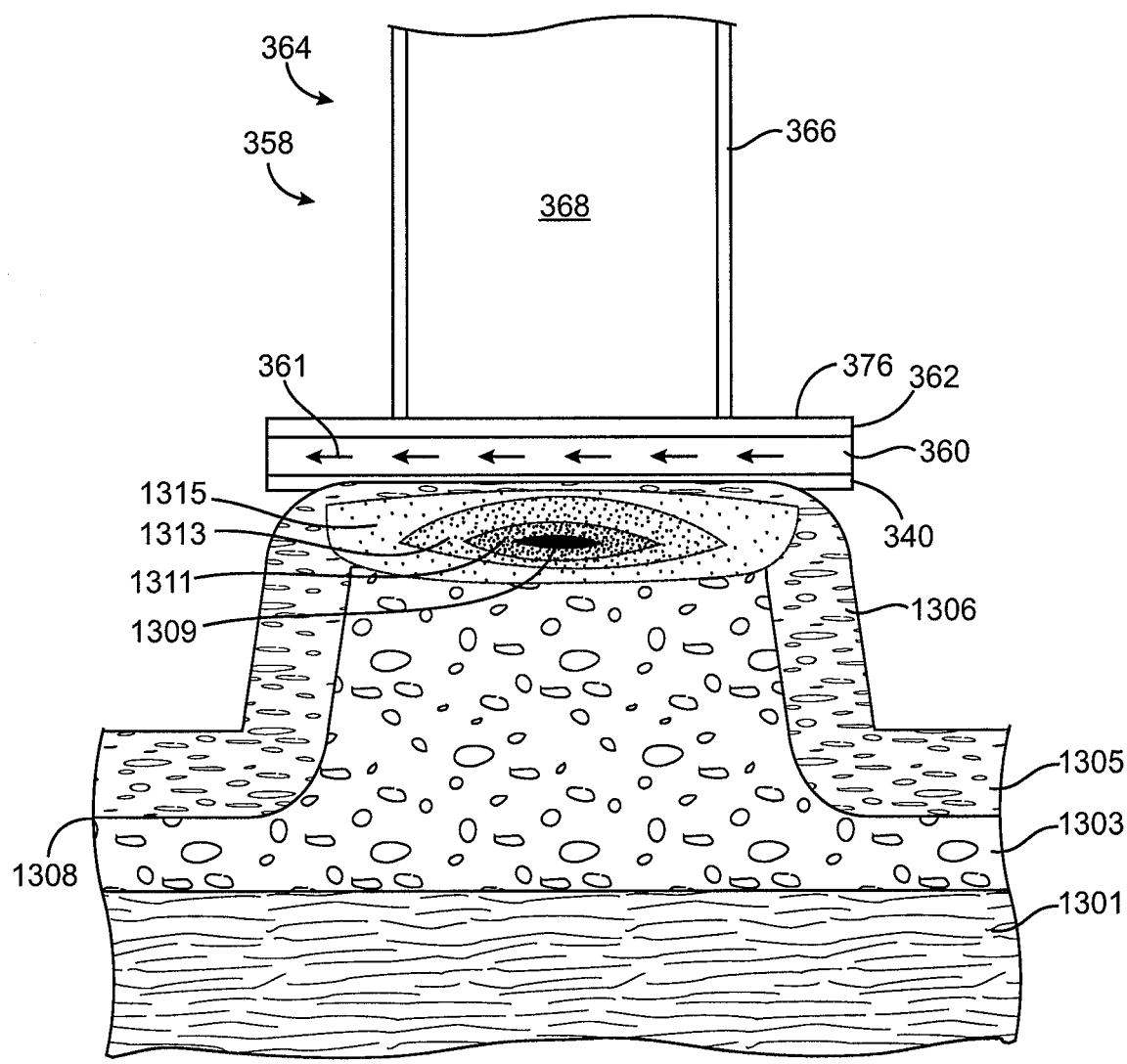
FIG. 50 illustrates a tissue profile according to one embodiment of the invention.
Figure 51:
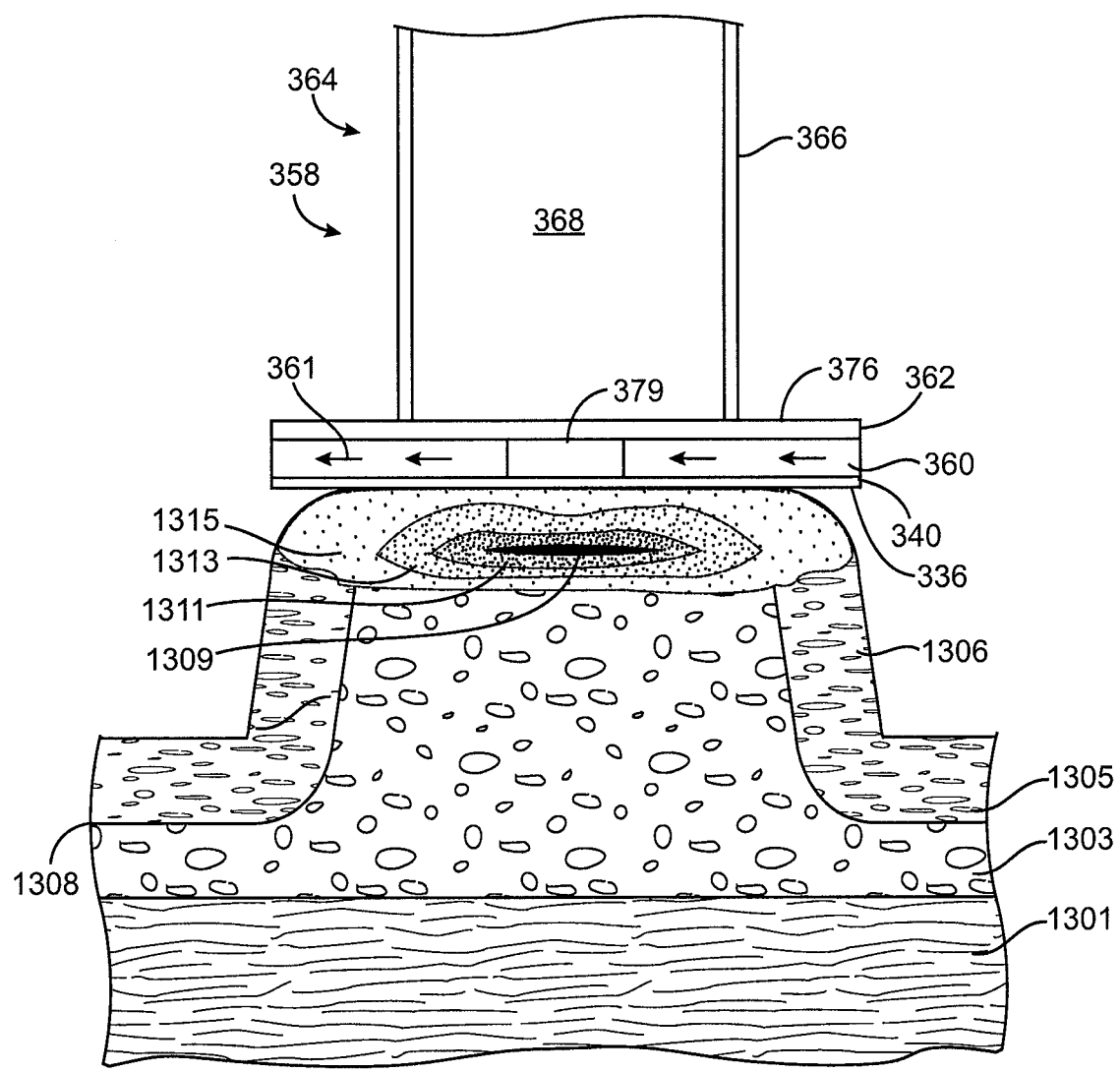
FIG. 51 illustrates a tissue profile according to one embodiment of the invention.

FIG. 50 illustrates a tissue profile according to one embodiment of the invention. FIG. 51 illustrates a tissue profile according to one embodiment of the invention. In the embodiment of the invention illustrated in FIGS. 50 and 51, antenna 358 may be, for example, a waveguide antenna 364. In one embodiment of the invention, waveguide antenna 364 may have a dielectric filler 368. In one embodiment of the invention, antenna 358 may be positioned on, for example, a tissue head 362 comprising, for example, standoff 376, coolant chamber 360 and cooling plate 340. In one embodiment of the invention, cooling chamber 340 may contain cooling fluid 361, which may be, for example de-ionized water. In one embodiment of the invention, a tissue head 362 may include a tissue chamber (not shown) adapted to position tissue against tissue interface 336. In one embodiment of the invention, antenna 358 is adapted to transmit electromagnetic radiation through skin surface 1306 creating a tissue profile which may be representative of, for example, a SAR profile, a power loss density profile or a temperature profile. In one embodiment of the invention, the tissue profile includes first tissue region 1309, second tissue region 1311, third tissue region 1313 and fourth tissue region 1315. In one embodiment of the invention, first tissue region 1309 may represent, for example, a peak SAR, peak power loss density or peak temperature. In one embodiment of the invention, first tissue region 1309 may be located in, for example, dermis 1305, near an interface 1308 between dermis 1305 and hypodermis 1303, which overlies muscle 1301. In the embodiment of the invention illustrated in FIG. 51, field spreader 379 is located in coolant chamber 360. In the embodiment of the invention illustrated in FIG. 51, field spreader 379 may be used to, for example, spread and flatten first tissue region 1309. In the embodiment of the invention illustrated in FIG. 51 field spreader 379 may be used to, for example, spread and flatten lesions formed in first tissue region 1309.

Further General Embodiments

Procedure

In one embodiment of the invention, electromagnetic power is delivered to the skin for a predetermined period of time. In one embodiment of the invention skin is engaged in, for example, a tissue chamber prior to the delivery of energy. In one embodiment of the invention, skin is cooled prior to the application of electromagnetic energy. In one embodiment of the invention, skin is cooled during the application of electromagnetic energy. In one embodiment of the invention, skin is cooled after the application of electromagnetic energy. In one embodiment of the invention, energy is delivered to the skin by applying a predetermined amount of power to an antenna positioned in close proximity, which may also be referred to as proximal, to the surface of the skin. In one embodiment of the invention, skin is positioned in close proximity to an electromagnetic energy device. In one embodiment of the invention, skin is positioned in close proximity to an electromagnetic energy delivery device using vacuum pressure to hold the skin in position. In one embodiment of the invention a region to be treated is anesthetized prior to treatment. In one embodiment of the invention anesthesia in the anesthetized region may change the dielectric properties of the tissue to be treated. In one embodiment of the invention, characteristics of the electromagnetic radiation irradiated through the skin are modified to account for variables, such as, for example the dielectric properties of the anesthesia, which determine anesthesia's influence on the treatment. Variables that may determine anesthesia's influence on treatment may include, for example: time from administration; vasodilatation or vasoconstriction characteristics of anesthetic; volume of anesthesia administered; anesthesia type (liquid injected, topical); location/depth in tissue anesthesia is administered; method of administration, such as, for example, one or multiple locations. In one embodiment of the invention, a template may be used to align a handpiece adapted to deliver electromagnetic energy to tissue. In one embodiment of the invention, a template may be used to align a handpiece as the handpiece is moved from position to position in, for example, the axilla. In one embodiment of the invention, a template is used to align an injection site for the delivery of, for example, anesthesia which may be, for example, lidocaine. In one embodiment of the invention, a template is used to facilitate treatment by indicating regions which have been previously treated. In one embodiment of the invention, a template may be aligned by, for example, using henna, sharpie marks or tattoos.

Tissue Structure

Regions

In one embodiment of the invention, tissue to be treated may be made up of layers having particular dielectric and conductivity characteristics. In one embodiment of the invention tissue having a high dielectric constant, also referred to as high dielectric tissue, may have a dielectric constant greater than approximately 25. In one embodiment of the invention tissue having a low dielectric constant, also referred to as low dielectric tissue, may have a dielectric constant less than approximately 10. In one embodiment of the invention tissue having a high conductivity, also referred to as high conductivity tissue, may have a conductivity greater than approximately 1.0 siemens per meter. In one embodiment of the invention tissue having a low conductivity, also referred to as high dielectric tissue, may have a conductivity of less than approximately 1.0 siemens per meter.

In one embodiment of the invention, low dielectric, low conductivity tissue may be, for example the hypodermis. In one embodiment of the invention, low dielectric tissue, low conductivity tissue, such as, for example, fat, may be tissue found in the hypodermis. In one embodiment of the invention, low dielectric, low conductivity tissue may be, for example a layer of the hypodermis below a glandular layer. In one embodiment of the invention, low dielectric tissue may be, for example the hypodermis. In one embodiment of the invention, low dielectric tissue, such as, for example, fat, may be tissue found in the hypodermis. In one embodiment of the invention, low dielectric tissue may be, for example a layer of the hypodermis below a glandular layer.

In one embodiment of the invention, high dielectric, high conductivity tissue may be, for example tissue found in the dermis. In one embodiment of the invention, high dielectric, high conductivity tissue may be, for example tissue found in the dermis. In one embodiment of the invention, high dielectric, high conductivity tissue may be, for example, tissue found in a glandular layer. In one embodiment of the invention, high dielectric, high conductivity tissue may be, for example, muscle tissue.

Glandular Layer

In one embodiment of the invention, a glandular layer may be, for example a layer of high dielectric, high conductivity tissue. In one embodiment of the invention, a glandular layer may be a layer of tissue with high water content. In one embodiment of the invention, a glandular layer may be a tissue layer in the region of an interface between the dermis and hypodermis which contains sufficient glandular tissue to raise the dielectric constant and conductivity of the glandular layer to a magnitude sufficient to create a standing wave pattern having a peak E-field in the glandular layer. In one embodiment of the invention, glandular tissue may occupy an average thickness of three to five millimeters in a five millimeter thick piece of human skin. In one embodiment of the invention, a glandular layer may include both apocrine gland lobules and eccrine gland lobules within the glandular layer. In one embodiment of the invention, a glandular layer may be a layer in the human axilla where substantially all of the sweat glands are localized. In one embodiment of the invention, wherein a glandular layer includes both apocrine and eccrine gland lobules, the apocrine gland modules may be more numerous and larger than the eccrine gland lobules. In one embodiment of the invention, a glandular layer may be a layer of tissue which includes a concentration of glands, such as, for example, eccrine, apoeccrine and/or apocrine sweat glands, sufficient to raise the conductivity of tissue surrounding the glands. In one embodiment of the invention, a glandular layer may be a layer of tissue which includes a concentration of glands, such as, for example, eccrine, apoeccrine and/or apocrine sweat glands, sufficient to raise the dielectric constant of tissue surrounding the glands. In one embodiment of the invention, a glandular layer may be a region of the hypodermis with sufficient glandular tissue to raise the dielectric constant of that region of the hypodermis to a magnitude sufficient to reduce or eliminate reflected electromagnetic radiation at the dermal, hypodermal interface. In one embodiment of the invention, a glandular layer may be a region of the hypodermis with sufficient glandular tissue to raise the dielectric constant of that region of the hypodermis to a magnitude sufficient to reduce or eliminate reflected electromagnetic radiation at the dermal, hypodermal interface, moving a standing wave into the hypodermis. In one embodiment of the invention, a glandular layer may be a region of the hypodermis with sufficient glandular tissue to raise dielectric constant to match the dielectric constant of the adjoining dermis. In one embodiment of the invention, a glandular layer may be a region of the hypodermis with sufficient glandular tissue to raise dielectric constant of the glandular layer to match the dielectric constant of surrounding hypodermis. In one embodiment of the invention, a glandular layer may be a region of the hypodermis with sufficient glandular tissue to raise dielectric constant of the glandular layer to exceed the dielectric constant of surrounding hypodermis. In one embodiment of the invention, a glandular layer may have a dielectric constant of greater than approximately 20. In one embodiment of the invention, a glandular layer may have a conductivity of greater than approximately 2.5 siemens per meter.

Interface

In one embodiment of the invention, a critical interface, which may also be referred to as a dielectric interface or a dielectric discontinuity, may be an interface between a layer of tissue having a high dielectric constant and high conductivity and a layer of tissue having a low dielectric constant. In one embodiment of the invention, a dielectric interface may be an interface between a layer of tissue having a high dielectric constant and high conductivity and a layer of tissue having a low dielectric constant and low conductivity. In one embodiment of the invention, a critical interface may exist at the interface between the dermis and a glandular layer. In one embodiment of the invention, a critical interface may be an interface between the dermis and the hypodermis. In one embodiment of the invention, a critical interface may be an interface between the dermis and a portion of the hypodermis. In one embodiment of the invention, a critical interface may be an interface between the dermis and a portion of the hypodermis having a limited number of sweat glands. In one embodiment of the invention, a critical interface may be an interface between the dermis and a region of the hypodermis which does not include a glandular region. In one embodiment of the invention, a critical interface may be an interface between the dermis and a region of the hypodermis which does not include a significant number of tissue structures.

Treatment

In embodiments of the invention, tissue to be treated may be treated by, for example, raising the temperature of the tissue. In embodiments of the invention, tissue to be treated may be treated by, for example, raising the temperature of the tissue to a temperature sufficient to cause a change in the tissue. In embodiments of the invention, tissue to be treated may be treated by, for example, raising the temperature of the tissue to a temperature sufficient to damage the tissue. In embodiments of the invention, tissue to be treated may be treated by, for example, raising the temperature of the tissue to a temperature sufficient to destroy the tissue. In embodiments of the invention, electromagnetic radiation is used to heat tissue to create a lesion where the lesion starts as a result of damage from heat generated by dielectric heating of tissue and the lesion is enlarged at least in part as consequence of thermal conduction of heat generated by the dielectric heating. In embodiments of the invention electromagnetic radiation may be used to heat the contents, such as, for example, sebum, of a tissue structure, such as, for example a hair follicle. In embodiments of the invention electromagnetic radiation may be used to heat the contents, such as, for example, sweat of a tissue structure, such as, for example a hair follicle. In embodiments of the invention electromagnetic radiation may be used to heat the contents, such as, for example, sebum of a tissue structure, such as, for example a hair follicle to a temperature sufficient to damage or destroy, for example, bacteria in the contents. In one embodiment of the invention, electromagnetic radiation may be used to heat tissue to a temperature sufficient to cause secondary effects in surrounding tissue or tissue structures, such as, for example, heating bacteria in surrounding tissue or surrounding tissue structures. In one embodiment of the invention, electromagnetic radiation may be used to heat tissue to a temperature sufficient to cause secondary effects in surrounding tissue or tissue structures, such as, for example, killing bacteria in surrounding tissue or surrounding tissue structures.

Target Tissue

In embodiments of the invention tissue to be treated as, for example, by raising the temperature of the tissue, may be referred to as target tissue.

Tissue to be Treated

Tissue Layers

In embodiments of the invention target tissue may be tissue adjacent to a dermal, hypodermal interface. In embodiments of the invention target tissue may be tissue in a dermal layer, in close proximity to a dermal, hypodermal interface. In embodiments of the invention target tissue may be deep dermal tissue. In embodiments of the invention target tissue may be tissue adjacent to a skin, fat interface. In embodiments of the invention target tissue may be tissue adjacent to a critical interface. In embodiments of the invention target tissue may be tissue adjacent to an interface between a glandular layer and a low dielectric layer. In embodiments of the invention target tissue may be tissue adjacent to an interface between a glandular layer and a layer of the hypodermis.

Physical Structures

In embodiments of the invention target tissue may be axillary tissue. In embodiments of the invention target tissue may be tissue in a hair bearing area. In embodiments of the invention target tissue may be tissue located in a region having at least 30 sweat glands per square centimeter. In embodiments of the invention target tissue may be tissue located in a region having an average of 100 sweat glands per square centimeter. In embodiments of the invention target tissue may be tissue located approximately 0.5 millimeters to 6 millimeters below the surface of the skin. In embodiments of the invention target tissue may be tissue located in a region where sweat glands, including, for example, apocrine and eccrine glands are located. In embodiments of the invention target tissue may be tissue located in a region where hair follicles are located.

Tissue Properties

In embodiments of the invention target tissue may be tissue subject to dielectric heating. In embodiments of the invention target tissue may be tissue having a high dipole moment. In embodiments of the invention, target tissue may be, for example, tissue containing exogenous materials. In embodiments of the invention target tissue may include tissue with bacteria. In embodiments of the invention target tissue may be, for example, collagen, hair follicles, cellulite, eccrine glands, apocrine glands, sebaceous glands or spider veins. In embodiments of the invention target tissue may be, for example, hair follicles. In embodiments of the invention target tissue may be, for example, regions of a hair follicle, including the lower segment (bulb and suprabulb), the middle segment (isthmus), and the upper segment (infundibulum). In embodiments of the invention target tissue may be, for example, structures associated with a hair follicle, such as, for example, stem cells.

Tissue Types

In embodiments of the invention target tissue may be human tissue. In embodiments of the invention target tissue may be porcine tissue. In embodiments of the invention target tissue may be, for example, wound tissue. In embodiments of the invention target tissue may be, for example, tissue to be insulted, as for example, skin tissue prior to surgery. In embodiments of the invention target tissue may be, for example, vessels, including veins, capillaries or arteries, supplying blood to tissue structures.

Effect

In embodiments of the invention, target tissue may be, for example, a volume of tissue defined by a region with a SAR greater than or equal to approximately fifty percent of peak SAR. In embodiments of the invention, target tissue may be, for example, a volume of tissue defined by a region with a SAR greater than or equal to between thirty and seventy percent of peak SAR Methods Tissue & Structures In one embodiment of the invention a method of treating target tissue is described. In one embodiment of the invention a method of damaging glands is described. In one embodiment of the invention a method of damaging hair follicles is described. In one embodiment of the invention a method of destroying tissue is described. In one embodiment of the invention a method of treating skin tissue is described. In one embodiment of the invention a method of preventing damage to tissue is described. In one embodiment of the invention a method of preventing the growth of a lesion toward a skin surface is described. In one embodiment of the invention, a method of damaging or destroying stem cells associated with hair follicles is described. In one embodiment of the invention, a method of aligning electromagnetic fields to preferentially treat tissue is described. In one embodiment of the invention, a method of aligning electromagnetic fields to preferentially treat tissue having a high water content is described. In embodiments of the invention, electromagnetic energy is used to heat sebum. In one embodiment of the invention, a method of creating a lesion in selected tissue regions is described. In one embodiment of the invention, a method of selectively depositing energy in selected tissue regions is described. In one embodiment of the invention, a method of selectively heating regions of tissue is described. In one embodiment of the invention, a method of preferentially heating regions of tissue is described.

Radiation

In one embodiment of the invention, a method of controlling power deposition in tissue is described. In one embodiment of the invention, a method of controlling E-field pattern in tissue is described. In one embodiment of the invention a method of creating a volume of high power deposition in tissue is described. In one embodiment of the invention a method of controlling output of a microwave device is described.

Lesion

In one embodiment of the invention a method of creating a lesion in tissue is described. In one embodiment of the invention a method of creating a subdermal lesion in tissue is described.

Gradients

In one embodiment of the invention a method of creating a temperature gradient within tissue is described. In one embodiment of the invention a method of creating a temperature gradient having a peak at a dermal, hypodermal interface is described. In one embodiment of the invention a method of creating a temperature gradient having a peak in dermal tissue adjacent the dermal, hypodermal interface is described. In one embodiment of the invention a method of creating a temperature gradient having a peak in glandular tissue is described. In one embodiment of the invention a method of creating a temperature gradient having a peak in glandular tissue adjacent an interface between glandular tissue and hypodermal tissue is described. In one embodiment of the invention a method of creating a temperature gradient having a peak adjacent a critical interface is described. In one embodiment of the invention a method of creating an inverse power gradient in tissue is described.

Clinical Indications

In one embodiment of the invention a method of reducing sweat is described. In one embodiment of the invention a method of reducing sweat production in a patient is described. In one embodiment of the invention a method of treating axillary hyperhidrosis is described. In one embodiment of the invention a method of treating hyperhidrosis is described. In one embodiment of the invention a method of removing hair is described. In one embodiment of the invention a method of preventing the re-growth of hair is described. In one embodiment of the invention, a method of treating osmidrosis is described. In one embodiment of the invention, a method of denervating tissue is described. In one embodiment of the invention, a method of treating port wine stains is described. In one embodiment of the invention, a method of treating hemangiomas is described. In one embodiment of the invention, a method of treating psoriasis is described. In one embodiment of the invention, a method of reducing sweat is described. In one embodiment of the invention, a method of reducing sweat is described. In embodiments of the invention, electromagnetic energy is used to treat acne. In one embodiment of the invention, a method of treating sebaceous glands is described. In one embodiment of the invention, a method of destroying bacteria is described. In one embodiment of the invention, a method of destroying propionibacterium is described. In one embodiment of the invention, a method of treating reducing inflammation is described. Further conditions and structures that can be treated in some embodiments are described in, for example, pp. 3-7 of U.S. Provisional App. No. 60/912,899; and pp. 1-10 of U.S. Provisional App. No. 61/013,274 both incorporated by reference in their entireties, as well as illustrated and described in, for example, pp. 8-12 of Appendix 1 and pp. 5-14 of Appendix 2.

In one embodiment of the invention electromagnetic energy may be used to reduce sweat. In one embodiment of the invention electromagnetic energy may be used to reduce sweat production in a patient. In one embodiment of the invention electromagnetic energy may be used to treat axillary hyperhidrosis. In one embodiment of the invention electromagnetic energy may be used to treat hyperhidrosis. In one embodiment of the invention electromagnetic energy may be used to remove hair. In one embodiment of the invention electromagnetic energy may be used to prevent the re-growth of hair. In one embodiment of the invention electromagnetic energy may be used to treat osmidrosis. In one embodiment of the invention, electromagnetic energy may be used to denervate tissue. In one embodiment of the invention electromagnetic energy may be used to treat port wine stains. In one embodiment of the invention electromagnetic energy may be used to treat hemangiomas. In one embodiment of the invention electromagnetic energy may be used to treat psoriasis. In one embodiment of the invention electromagnetic energy may be used to reduce sweat. In embodiments of the invention, electromagnetic energy may be used to treat acne. In embodiments of the invention, electromagnetic energy may be used to treat sebaceous glands. In embodiments of the invention, electromagnetic energy may be used to destroy bacteria. In embodiments of the invention, electromagnetic energy may be used to destroy propionibacterium. In embodiments of the invention, electromagnetic energy may be used to clear sebum from a hair follicle. In embodiments of the invention, electromagnetic energy may be used to clear obstructed hair follicles. In embodiments of the invention, electromagnetic energy may be used to reverse comedogenesis. In embodiments of the invention, electromagnetic energy may be used to clear blackheads. In embodiments of the invention, electromagnetic energy may be used to clear whiteheads. In embodiments of the invention, electromagnetic energy may be used to reducing inflammation.

Positioning

In one embodiment of the invention a method of positioning skin is described. In one embodiment of the invention a method of positioning a dermal, hypodermal interface is described. In one embodiment of the invention a method of positioning a critical interface is described. In one embodiment of the invention a method of positioning a skin, fat interface is described. In one embodiment of the invention a method of positioning an interface between a glandular layer and a layer of hypodermal tissue is described. In one embodiment of the invention a method of separating target tissue from muscle is described. In one embodiment of the invention a method of separating skin tissue from muscle is described.

Power Loss Density or Specific Absorption Rate

Skin

In one embodiment of the invention, irradiating tissue through the surface of skin with electromagnetic radiation results in a region of localized high power loss density or SAR below the skin surface. In one embodiment of the invention, irradiating tissue through the surface of skin with electromagnetic radiation results in a region of localized high power loss density or SAR in a region of the skin below an upper layer of the skin. In one embodiment of the invention, irradiating tissue through the surface of skin with electromagnetic radiation generates a region of localized high power loss density or SAR in a layer of the skin adjacent a critical interface. In one embodiment of the invention, irradiating tissue through the surface of skin with electromagnetic radiation generates a region of localized high power loss density or SAR in a layer of the skin adjacent a critical interface and between the skin surface and the critical interface.

Dermis

In one embodiment of the invention, irradiating tissue through the surface of skin with electromagnetic radiation generates a region of localized high power loss density or SAR in a region of the dermis. In one embodiment of the invention, radiating the surface of skin with electromagnetic radiation generates a region of localized high power loss density or SAR in a region of the dermis below an upper layer of the dermis. In one embodiment of the invention, irradiating tissue through the surface of skin with electromagnetic radiation generates a region of localized high power loss density or SAR in a region of the dermis adjacent an interface between the dermis and the epidermis. In one embodiment of the invention, irradiating tissue through the surface of skin with electromagnetic radiation generates a region of localized high power loss density or SAR in a region of the dermis adjacent a critical interface.

In embodiments of the invention, regions of localized high power loss density or regions of localized high specific absorption rate result in the deposition of sufficient energy into those regions to raise the temperature of those regions above the temperature of surrounding regions. In embodiments of the invention, regions of localized high power loss density or regions of localized high specific absorption rate result in the deposition of sufficient energy into those regions to raise the temperature of those regions to a temperature sufficient to create lesions in those regions. In embodiments of the invention, regions of localized high power loss density or regions of localized high specific absorption rate result in the deposition of sufficient energy into those regions to raise the temperature of those regions to a temperature sufficient to heat surrounding regions by, for example, thermal conductive heating.

Glandular Layer

In one embodiment of the invention, irradiating tissue through the surface of skin with electromagnetic radiation generates a region of localized high power loss density or SAR in a glandular layer. In one embodiment of the invention, irradiating tissue through the surface of skin with electromagnetic radiation generates a region of localized high power loss density or SAR in a glandular layer adjacent a critical interface. In one embodiment of the invention, irradiating tissue through the surface of skin with electromagnetic radiation generates a region of localized high power loss density or SAR in a glandular layer adjacent a critical interface and below a first layer of skin. In one embodiment of the invention, irradiating tissue through the surface of skin with electromagnetic radiation generates a region of localized high power loss density or SAR in a glandular layer adjacent a critical interface and below at least a portion of the dermis.

Temperature Gradient

Skin

In one embodiment of the invention, irradiating tissue through the surface of skin with electromagnetic radiation generates a temperature gradient having a peak in a region below the skin surface. In one embodiment of the invention, irradiating tissue through the surface of skin with electromagnetic radiation generates a temperature gradient having a peak in a region of the skin below an upper layer of the skin. In one embodiment of the invention, irradiating tissue through the surface of skin with electromagnetic radiation generates a temperature gradient having a peak in a layer of the skin adjacent to a critical interface. In one embodiment of the invention, irradiating tissue through the surface of skin with electromagnetic radiation generates a temperature gradient having a peak in a layer of the skin adjacent to a critical interface and between a critical interface and the surface of the skin.

Dermis

In one embodiment of the invention, electromagnetic radiation generates a temperature gradient where the temperature gradient has a peak in a layer of the dermis below the surface of the skin. In one embodiment of the invention, electromagnetic radiation generates a temperature gradient where the temperature gradient has a peak in a layer of the dermis below an upper layer of the dermis. In one embodiment of the invention, electromagnetic radiation generates a temperature gradient where the temperature gradient has a peak in a region of the dermis adjacent an interface between the dermis and the hypodermis. In one embodiment of the invention, electromagnetic radiation generates a temperature gradient where the temperature gradient has a peak in a region of the dermis adjacent a critical interface.

Glandular Layer

In one embodiment of the invention irradiating tissue through the surface of skin with electromagnetic radiation generates a temperature gradient having a peak in a glandular layer below the skin surface. In one embodiment of the invention, irradiating tissue through the surface of skin with electromagnetic radiation generates a temperature gradient having a peak in a glandular layer adjacent a critical interface. In one embodiment of the invention, irradiating tissue through the surface of skin with electromagnetic radiation generates a temperature gradient having a peak in a glandular layer adjacent a critical interface and below a first layer of skin.

Inverse Power Gradient

Skin

In one embodiment of the invention, irradiating tissue through the surface of skin with electromagnetic radiation generates an inverse power gradient having a peak in a region below the skin surface. In one embodiment of the invention, irradiating tissue through the surface of skin with electromagnetic radiation generates an inverse power gradient having a peak in a region of the skin below an upper layer of the skin. In one embodiment of the invention, irradiating tissue through the surface of skin with electromagnetic radiation generates an inverse power gradient having a peak in a layer of the skin adjacent to a critical interface. In one embodiment of the invention, irradiating tissue through the surface of skin with electromagnetic radiation generates an inverse power gradient having a peak in a layer of the skin adjacent to a critical interface and between a critical interface and the surface of the skin.

Dermis

In one embodiment of the invention, electromagnetic radiation generates an inverse power gradient where the inverse power gradient has a peak in a layer of the dermis below the surface of the skin. In one embodiment of the invention, electromagnetic radiation generates an inverse power gradient where the inverse power gradient has a peak in a layer of the dermis below an upper layer of the dermis. In one embodiment of the invention, electromagnetic radiation generates an inverse power gradient where the inverse power gradient has a peak in a region of the dermis adjacent an interface between the dermis and the hypodermis. In one embodiment of the invention, electromagnetic radiation generates an inverse power gradient where the inverse power gradient has a peak in a region of the dermis adjacent a critical interface.

Glandular Layer

In one embodiment of the invention irradiating tissue through the surface of skin with electromagnetic radiation generates an inverse power gradient having a peak in a glandular layer below the skin surface. In one embodiment of the invention, irradiating tissue through the surface of skin with electromagnetic radiation generates an inverse power gradient having a peak in a glandular layer adjacent a critical interface. In one embodiment of the invention, irradiating tissue through the surface of skin with electromagnetic radiation generates an inverse power gradient having a peak in a glandular layer adjacent a critical interface and below a first layer of skin.

Lesion

Skin

In one embodiment of the invention, electromagnetic radiation is used to create a lesion in a region below the skin surface. In one embodiment of the invention, electromagnetic radiation is used to create a lesion in a region below the skin surface where the lesion starts in a layer below an upper layer of the skin. In one embodiment of the invention, is used to create a lesion in skin where the lesion starts in a layer of the skin adjacent a critical interface. In one embodiment of the invention, is used to create a lesion in skin where the lesion starts in a layer of the skin adjacent a critical interface and between the skin surface and the critical interface.

Dermis

In one embodiment of the invention, electromagnetic radiation is used to create a lesion in skin where the lesion starts in a layer of the dermis below the surface of the skin. In one embodiment of the invention, electromagnetic radiation is used to create a lesion in skin where the lesion starts in a layer of the dermis below an upper layer of the dermis. In one embodiment of the invention, electromagnetic radiation is used to create a lesion in skin, where the lesion starts in a region of the dermis in close proximity to the interface between the dermis and the hypodermis. In one embodiment of the invention, electromagnetic radiation is used to create a lesion in skin, where the lesion starts in a region of the dermis adjacent a critical interface.

Glandular Layer

In one embodiment of the invention, electromagnetic radiation is used to create a lesion which starts in a glandular layer. In one embodiment of the invention, electromagnetic radiation is used to create a lesion which starts in a glandular layer adjacent a critical interface. In one embodiment of the invention, electromagnetic radiation is used to create a lesion which starts in a glandular layer adjacent a critical interface and below a first layer of skin.

Skin

In one embodiment of the invention, electromagnetic radiation is used to create a lesion in a region below the skin surface in the absence of any external mechanism for removing heat from the surface of the skin. In one embodiment of the invention, electromagnetic radiation is used to create a lesion in a region below the skin surface where the lesion starts in a layer below an upper layer of the skin in the absence of any external mechanism for removing heat from the surface of the skin. In one embodiment of the invention, is used to create a lesion in skin where the lesion starts in a layer of the skin adjacent a critical interface in the absence of any external mechanism for removing heat from the surface of the skin. In one embodiment of the invention, is used to create a lesion in skin where the lesion starts in a layer of the skin adjacent a critical interface and between the skin surface and the critical interface in the absence of any external mechanism for removing heat from the surface of the skin.

Dermis

In one embodiment of the invention, electromagnetic radiation is used to create a lesion in skin where the lesion starts in a layer of the dermis below the surface of the skin in the absence of any external mechanism for removing heat from the surface of the skin. In one embodiment of the invention, electromagnetic radiation is used to create a lesion in skin where the lesion starts in a layer of the dermis below an upper layer of the dermis in the absence of any external mechanism for removing heat from the surface of the skin. In one embodiment of the invention, electromagnetic radiation is used to create a lesion in skin, where the lesion starts in a region of the dermis in close proximity to the interface between the dermis and the hypodermis in the absence of any external mechanism for removing heat from the surface of the skin. In one embodiment of the invention, electromagnetic radiation is used to create a lesion in skin, where the lesion starts in a region of the dermis adjacent a critical interface in the absence of any external mechanism for removing heat from the surface of the skin.

Glandular Layer

In one embodiment of the invention, electromagnetic radiation is used to create a lesion which starts in a glandular layer in the absence of any external mechanism for removing heat from the surface of the skin. In one embodiment of the invention, electromagnetic radiation is used to create a lesion which starts in a glandular layer adjacent a critical interface in the absence of any external mechanism for removing heat from the surface of the skin. In one embodiment of the invention, electromagnetic radiation is used to create a lesion which starts in a glandular layer adjacent a critical interface and below a first layer of skin in the absence of any external mechanism for removing heat from the surface of the skin.

Lesion Origin

In one embodiment of the invention, a lesion origin may be located at a point or region in high dielectric, high conductivity tissue adjacent low dielectric tissue. In one embodiment of the invention, a lesion origin may be a point or region in tissue where a tissue reaches a temperature sufficient to allow a lesion to begin to grow. In one embodiment of the invention, a lesion origin may be located at a point or region in high dielectric, high conductivity tissue adjacent a critical interface. In one embodiment of the invention, the lesion origin may be located at a point or region where microwave energy radiated through the surface of the skin generates a standing wave pattern having a peak E-field. In one embodiment of the invention, the lesion origin may be located in high dielectric/high conductivity tissue near a critical interface where microwave energy radiated through the surface of the skin generates constructive interference.

Electromagnetic Radiation Characteristics

In one embodiment of the invention, skin is irradiated by electromagnetic radiation having specific characteristics and, more particularly, specific E-field characteristics. In one embodiment of the invention, skin is irradiated with electromagnetic radiation wherein the polarization of the E-field component of the electromagnetic radiation is substantially parallel to the skin's outer surface. In one embodiment of the invention, skin is irradiated with electromagnetic radiation wherein the E-field component of the electromagnetic radiation is substantially parallel to at least one interface between tissue layers within the skin. In one embodiment of the invention, skin is irradiated with electromagnetic radiation wherein the E-field component of the electromagnetic radiation is substantially parallel to a critical interface. In one embodiment of the invention, skin is irradiated with electromagnetic radiation wherein the E-field component of the electromagnetic radiation is substantially parallel to the interface between the dermis and the hypodermis. In one embodiment of the invention, skin is irradiated with electromagnetic radiation wherein the E-field component of the electromagnetic radiation is substantially parallel to the interface between a glandular layer and a portion of the hypodermis. In one embodiment of the invention, an E-field component may be considered to be substantially parallel to, for example, a critical interface when such E-field component is substantially parallel to an idealized average interface, such as, for example, the idealized interface 1308 or 1333 used in the Figures. In one embodiment of the invention, an E-field component may be considered to be substantially parallel to, for example, a critical interface when such E-field component is substantially parallel to at least a portion of such interface, such as, for example, a portion of such interface underlying an aperture of an antenna radiating the E-field.

In one embodiment of the invention, skin is irradiated by electromagnetic radiation having specific characteristics and, more particularly, specific polarization characteristics. In one embodiment of the invention, skin is irradiated with electromagnetic radiation wherein the electromagnetic radiation is polarized such that the E-field component of the electromagnetic radiation is substantially parallel to the skin's outer surface. In one embodiment of the invention, skin is irradiated with electromagnetic radiation wherein the electromagnetic radiation is polarized such that the E-field component of the electromagnetic radiation is substantially parallel to at least one interface between tissue layers within the skin. In one embodiment of the invention, skin is irradiated with electromagnetic radiation wherein the electromagnetic radiation is polarized such that the E-field component of the electromagnetic radiation is substantially parallel to the interface between the dermis and the hypodermis. In one embodiment of the invention, skin is irradiated with electromagnetic radiation wherein the electromagnetic radiation is polarized such that the E-field component of the electromagnetic radiation is substantially parallel to an interface between a glandular layer and the hypodermis.

In one embodiment of the invention, an E-field may be made up of at least two E-field components, wherein one of said E-field components is parallel to a skin surface or a critical interface and a second E-field component is perpendicular to the first E-field component. In one embodiment of the invention, an E-field may be substantially parallel to a surface or interface when the magnitude of an E-field component parallel to that surface or interface is greater than 75 percent of the total E-field magnitude. In one embodiment of the invention, an E-field may be made up of a transverse E-field component and a perpendicular E-field component. In one embodiment of the invention, an E-field may be made up a transverse E-field component may be parallel to a skin surface or a critical interface. In one embodiment of the invention, an E-field may be substantially parallel to a surface or interface when the magnitude of a transverse E-field component is greater than 75 percent of the total E-field magnitude.

In one embodiment of the invention, skin is irradiated by electromagnetic radiation having specific characteristics and, more particularly, specific frequency characteristics. In one embodiment of the invention, skin is irradiated by electromagnetic radiation having a frequency of approximately 5.8 GHz. In one embodiment of the invention, skin is irradiated by electromagnetic radiation having a frequency of between 5 GHz and 6.5 GHz. In one embodiment of the invention, skin is irradiated by electromagnetic radiation having a frequency of between 4.0 GHz and 10 GHz.

In one embodiment of the invention, skin is irradiated by electromagnetic radiation having specific characteristics and, more particularly, specific characteristics within tissue. In one embodiment of the invention, skin is irradiated by electromagnetic radiation which generates a constructive interference pattern having a peak within the skin. In one embodiment of the invention, skin is irradiated by electromagnetic radiation which generates a constructive interference pattern in the dermis, wherein the constructive interference pattern has a peak in a region of the dermis which is below a first layer of the dermis and where destructive interference occurs in the first layer of the dermis. In one embodiment of the invention, skin is irradiated by electromagnetic radiation which generates a constructive interference pattern, wherein the constructive interference pattern has a peak adjacent a critical interface. In one embodiment of the invention, skin is irradiated by electromagnetic radiation which generates a constructive interference pattern having a peak in a glandular layer. In one embodiment of the invention, skin irradiated with electromagnetic radiation generates a constructive interference pattern that generates a peak electric field in a tissue layer. In one embodiment of the invention, skin irradiated with electromagnetic radiation generates a constructive interference pattern that generates a region of localized high power loss density, SAR or tissue temperature.

In one embodiment of the invention, skin is irradiated by electromagnetic radiation having specific characteristics and, more particularly, specific characteristics within skin. In one embodiment of the invention, skin is irradiated by electromagnetic radiation which generates a destructive interference pattern within the skin. In one embodiment of the invention, skin irradiated with electromagnetic radiation generates a destructive interference pattern that generates a minimum electric field in a tissue layer. In one embodiment of the invention, skin irradiated with electromagnetic radiation generates a destructive interference pattern that generates a region of localized low power loss density, SAR or tissue temperature. In one embodiment of the invention, skin is irradiated by electromagnetic radiation which generates a destructive interference pattern in the dermis, wherein the destructive interference pattern has a peak in a region of the dermis which is above a deep layer of the dermis. In one embodiment of the invention, skin is irradiated by electromagnetic radiation which generates a destructive interference pattern having a peak in tissue between a skin surface and a glandular layer.

In one embodiment of the invention, skin is irradiated by electromagnetic radiation having specific characteristics and, more particularly, specific characteristics within tissue. In one embodiment of the invention, skin is irradiated by electromagnetic radiation which generates a standing wave pattern within the skin. In one embodiment of the invention, skin is irradiated by electromagnetic radiation which generates a standing wave pattern having a peak in the dermis below a first layer of the dermis. In one embodiment of the invention, skin is irradiated by electromagnetic radiation which generates a standing wave pattern having a peak adjacent a critical interface. In one embodiment of the invention, skin is irradiated by electromagnetic radiation which generates a standing wave pattern having a peak in a glandular layer. In one embodiment of the invention, skin irradiated with electromagnetic radiation generates a standing wave pattern that generates a peak electric field. In one embodiment of the invention, skin irradiated with electromagnetic radiation generates a standing wave pattern that generates a region of localized high power loss density, SAR or tissue temperature. In one embodiment of the invention, skin irradiated with electromagnetic radiation generates a standing wave pattern that generates a region of localized low power loss density, SAR or tissue temperature.

Antenna

In one embodiment of the invention, skin is irradiated by electromagnetic radiation having specific characteristics and, more particularly, specific characteristics resulting from the position of the antenna radiating the electromagnetic radiation. In one embodiment of the invention, skin is irradiated by electromagnetic radiation generated by an antenna positioned in close proximity to the skin surface. In one embodiment of the invention, skin is irradiated by an antenna located in the radiating near field region with respect to the surface of adjacent skin. In one embodiment of the invention, skin is irradiated by an antenna located substantially in the radiating near field region with respect to the surface of adjacent skin. In one embodiment of the invention, skin is irradiated by an antenna located less than one half of one wavelength from the surface of adjacent skin. In one embodiment of the invention, skin is irradiated by an antenna located less than one half of one wavelength from the surface of adjacent skin, wherein a wavelength is measured in dielectric material separating the antenna from the skin surface. In one embodiment of the invention, skin is irradiated by an antenna located less than one half of one wavelength from the surface of adjacent skin, wherein a wavelength is measured in cooling fluid separating the antenna from the skin surface. In one embodiment of the invention, skin is irradiated by an antenna located less approximately 3 millimeters from the skin surface. In one embodiment of the invention, skin is irradiated by an antenna located less approximately 1.5 millimeters from the skin surface. In one embodiment of the invention, wavelength of a radiated signal is the wavelength in air divided by the square root of the dielectric constant of materials separating the antenna from the skin surface. In one embodiment of the invention, wavelength of a radiated signal is the wavelength in air divided by the square root of the dielectric constant of cooling fluid separating the antenna from the skin surface.

In one embodiment of the invention, skin is irradiated by electromagnetic radiation having specific characteristics and, more particularly, specific characteristics resulting from the position of the output of the antenna radiating the electromagnetic radiation. In one embodiment of the invention, skin is irradiated by an antenna having an output in the radiating near field region with respect to the surface of adjacent skin. In one embodiment of the invention, skin is irradiated by an antenna having an output outside the reactive near field region with respect to the surface of adjacent skin. In one embodiment of the invention, skin is irradiated by an antenna having an output which is not in the far field region with respect to the surface of adjacent skin.

In one embodiment of the invention, skin is irradiated by electromagnetic radiation having specific characteristics and, more particularly, specific characteristics related to the position of a radiating aperture in the antenna radiating the electromagnetic radiation. In one embodiment of the invention, skin is irradiated by an antenna having a radiating aperture in the radiating near field region with respect to the surface of adjacent skin. In one embodiment of the invention, skin is irradiated by an antenna having a radiating aperture outside the reactive near field with respect to the surface of adjacent skin. In one embodiment of the invention, skin is irradiated by an antenna having a radiating aperture which is not in the far field region with respect to the surface of adjacent skin.

In one embodiment of the invention, a reactive near field region may be, for example, that portion of the near field region immediately surrounding the antenna where the near reactive field predominates. In one embodiment of the invention, an antenna may be located a distance from a skin surface which may be approximately 0.62 times the square root of $D^3$/Lambda, where D is the largest physical dimension of the antenna aperture and Lambda is the wavelength of the electromagnetic radiation transmitted by the antenna measured in the medium positioned between the antenna output and skin surface. In one embodiment of the invention, a radiating near field region may be, for example, that that region of the field of an antenna between the reactive near field region and the far field region wherein radiation fields predominate. In one embodiment of the invention, an antenna may be located a maximum distance from a skin surface which may be approximately 2 times $D^2$/Lambda, where D is the largest physical dimension of the antenna aperture and Lambda is the wavelength of the electromagnetic radiation transmitted by the antenna measured in the medium positioned between the antenna output and skin surface. In one embodiment of the invention, an antenna may be located a less than approximately 2 times $D^2$/Lambda In one embodiment of the invention, a far field region may be, for example, that region of the field of an antenna where the angular field distribution is essentially independent of the distance from the antenna.

In one embodiment of the invention, skin is irradiated by electromagnetic radiation having specific characteristics and, more particularly, specific characteristics resulting from the configuration of the antenna which radiates the electromagnetic radiation. In one embodiment of the invention, skin is irradiated by an antenna configured to radiate a field pattern primarily in the TE mode. In one embodiment of the invention, skin is irradiated by an antenna configured to radiate a field pattern primarily in the $TE_{10}$ mode. In one embodiment of the invention, skin is irradiated by an antenna configured to radiate a field pattern solely in $TE_{10}$ mode. In one embodiment of the invention, skin is irradiated by an antenna configured to radiate a field pattern primarily in the TEM mode. In one embodiment of the invention, skin is irradiated by an antenna configured to radiate a field pattern solely in TEM mode. In embodiments of the invention, TE, TEM and $TE_{10}$ are particularly useful as they are modes in which radiated electromagnetic energy includes E-Fields in the transverse direction. Thus, where an antenna is positioned appropriately, an antenna transmitting electromagnetic energy in a TE, TEM or $TE_{10}$ mode will generate an E-field which may be parallel or substantially parallel to a skin surface adjacent the antenna or to a critical interface, such as, for example, an interface between the dermis and the hypodermis.

In one embodiment of the invention, skin is irradiated by electromagnetic radiation having specific characteristics and, more particularly, specific characteristics resulting from the configuration of the antenna which radiates the electromagnetic radiation. In one embodiment of the invention, skin is irradiated by an antenna configured to radiate electromagnetic energy having an E-field component which is substantially parallel to the surface of the skin. In one embodiment of the invention, skin is irradiated by an antenna configured to radiate electromagnetic energy having an E-field component which is substantially parallel to a critical interface. In one embodiment of the invention, skin is irradiated by an antenna configured to radiate electromagnetic energy having an E-field component which is substantially parallel to the interface between the dermis and the hypodermis. In one embodiment of the invention, skin is irradiated by an antenna configured to radiate electromagnetic energy having an E-field component which is substantially parallel to an interface between a glandular region and a portion of the hypodermis.

In one embodiment of the invention, skin is irradiated by electromagnetic radiation having specific characteristics and, more particularly, specific characteristics resulting from the configuration of the antenna which radiates the electromagnetic radiation. In one embodiment of the invention, skin is irradiated by an antenna configured to generate a standing wave in adjacent tissue. In one embodiment of the invention, skin is irradiated by an antenna configured to generate a standing wave in adjacent tissue wherein the standing wave has a peak adjacent a critical interface. In one embodiment of the invention, skin is irradiated by an antenna configured to generate a standing wave in adjacent tissue wherein the standing wave has a peak in dermal tissue adjacent a dermal, subdermal interface. In one embodiment of the invention, skin is irradiated by an antenna configured to generate a standing wave in adjacent tissue wherein the standing wave has a peak in a glandular layer.

In one embodiment of the invention, skin is irradiated by electromagnetic radiation having specific characteristics and, more particularly, specific characteristics resulting from the configuration of the antenna which radiates the electromagnetic radiation. In one embodiment of the invention, skin is irradiated by an antenna configured to generate constructive interference in adjacent tissue. In one embodiment of the invention, skin is irradiated by an antenna configured to generate constructive interference in adjacent tissue wherein the constructive interference has a peak adjacent a critical interface. In one embodiment of the invention, skin is irradiated by an antenna configured to generate constructive interference in adjacent tissue wherein the standing wave has a peak in dermal tissue adjacent a dermal, subdermal interface. In one embodiment of the invention, skin is irradiated by an antenna configured to generate constructive interference in adjacent tissue wherein the standing wave has a peak in a glandular layer.

Heating Tissue/Tissue Structures

In one embodiment of the invention, tissue is heated by conducting heat generated in a lesion to specified tissue. In one embodiment of the invention, tissue is heated by conducting heat generated in a lesion through intermediate tissue wherein heat in the lesion is generated primarily by dielectric heating. In one embodiment of the invention, tissue located below a critical interface is heated by conducting heat generated in a lesion across the critical interface. In one embodiment of the invention, a method is described for heating tissue located below a critical interface by conducting heat generated in a lesion located above the critical interface wherein heat generated in the lesion is generated primarily by dielectric heating and heat below the critical interface is generated primarily by conduction of heat from the lesion through intermediate tissue to tissue located below a dielectric barrier.

In one embodiment of the invention, tissue structures, such as, for example sweat glands or hair follicles, located in the region of the skin near a critical interface are heated. In one embodiment of the invention, tissue structures located near a critical interface are heated primarily by conduction of heat from a lesion. In one embodiment of the invention, tissue structures located near a critical interface are heated primarily by conduction of heat from a lesion, wherein the lesion is created by dielectric heating. In one embodiment of the invention, tissue structures located in a first tissue layer are heated by heat generated in the first tissue layer as a result of a standing wave generated in the first tissue layer by reflections off a critical interface.

In one embodiment of the invention, tissue structures located in the region of the skin where the dermis and hypodermis layer meet are heated. In one embodiment of the invention, tissue structures located in a glandular layer are heated. In one embodiment of the invention, tissue structures located in the region of the skin where the dermis and hypodermis layer meet are damaged. In one embodiment of the invention, tissue structures located in a glandular layer are damaged. In one embodiment of the invention, tissue structures located in the region of the skin where the dermis and hypodermis layer meet are destroyed. In one embodiment of the invention, tissue structures located in a glandular layer are destroyed. In one embodiment of the invention, tissue elements are heated by conducting heat generated in a lesion through intermediate tissue to the tissue elements, wherein heat in the lesion is generated primarily by dielectric heating. In one embodiment of the invention, tissue structures located below a critical interface are heated by conducting heat generated in a lesion above the critical interface primarily by dielectric heating through intermediate tissue to tissue structures located below a the critical interface.

In one embodiment of the invention a region adjacent a critical interface may be heated by depositing more energy into that region than into surrounding tissue. In one embodiment of the invention, tissue in the dermal layer, adjacent to the interface between the dermal layer and the subdermal layer is preferentially heated. In one embodiment of the invention, tissue in a glandular layer is preferentially heated. In one embodiment of the invention, tissue in a glandular layer adjacent a critical interface is preferentially heated.

Cooling

In one embodiment of the invention, heat generated in tissue below the surface of the skin is prevented from damaging tissue adjacent the surface of the skin by removing heat from the surface of the skin. In one embodiment of the invention, heat generated in tissue below the surface of the skin is prevented from damaging tissue adjacent the surface of the skin by cooling the surface of the skin.

In one embodiment of the invention, a method is described for preventing heat generated in a lesion by dielectric heating from damaging tissue in a skin layer positioned between the lesion and the surface of the skin. In one embodiment of the invention, a method is described for preventing heat generated in a lesion by dielectric heating from damaging tissue in a skin layer positioned between the lesion and the surface of the skin by removing heat from a skin surface. In one embodiment of the invention, a method is described for preventing heat generated in a lesion by dielectric heating from damaging tissue in a skin layer positioned between the lesion and the surface of the skin by cooling a skin surface.

In one embodiment of the invention, a method is described for preventing heat generated in a lesion having an origin in a layer of tissue from damaging tissue in a layer of tissue positioned between the lesion origin and the surface of the skin. In one embodiment of the invention, a method is described for preventing heat generated in a lesion having an origin in a layer of tissue from damaging tissue in a skin layer positioned between the lesion and the surface of the skin by removing heat from a skin surface. In one embodiment of the invention, a method is described for preventing heat generated in a lesion having an origin in a layer of tissue from damaging tissue in a skin layer positioned between the lesion and the surface of the skin by cooling a skin surface.

In one embodiment of the invention, a method is described for preventing lesion from growing toward the surface of the skin. In one embodiment of the invention, a method is described for preventing lesion from growing toward the surface of the skin by removing heat from the skin surface. In one embodiment of the invention, a method is described for preventing lesion from growing toward the surface of the skin by cooling the skin surface.

In one embodiment of the invention, cooling may be turned off for a period after energy is delivered and resumed thereafter. In one embodiment of the invention, cooling may be turned off for a period of for example, approximately 2 seconds after energy is delivered. In one embodiment of the invention, cooling turned on and off in a pulsed manner to control the amount of heat removed through the skin surface.

Antenna System

Antenna Types

In embodiments of the invention, antenna 358 may be, for example: a coaxial single slot antenna; a coaxial multiple slot antenna; a printed slot antenna; a waveguide antenna; a horn antenna; a patch antenna; a patch trace antenna; a Vivaldi antenna; or a waveguide antenna. In embodiments of the invention, an antenna may be, for example an array of antennas. In embodiments of the invention, an antenna may be, for example an array of antennas wherein one or more of the antennas radiate electromagnetic energy at the same time. In embodiments of the invention, an antenna may be, for example an array of antennas wherein at least one but not all of the antennas radiate electromagnetic energy at the same time. In embodiments of the invention, an antenna may be, for example, two or more different types of antennas. In embodiments of the invention, specific antennas in an array may be selectively activated or deactivated. Additional embodiments of antennas that can be used in conjunction with embodiments and components of the present application can be found, for example, in U.S. Provisional Application No. 60/912,899, entitled METHODS AND APPARATUS FOR REDUCING SWEAT PRODUCTION, filed Apr. 19, 2007, incorporated by reference in its entirety, e.g., in FIGS. 3, 4, 5, 6C, 12F, 34A, and 38 and the accompanying description, as well as in U.S. Provisional Application No. 61/013,274, entitled METHODS, DEVICES, AND SYSTEMS FOR NON-INVASIVE DELIVERY OF MICROWAVE THERAPY, filed Dec. 12, 2007 and incorporated by reference in its entirety, e.g., in FIGS. 2C, 3A, 5, 6, 11A, 11B, 20, 21A, 21B, 22, 22A and 23.

Return Loss/Bandwidth

In one embodiment of the invention, an antenna has an optimized return loss ($S_{11}$) profile centered on 5.8 GHz. S11 in dB or return loss (the magnitude of $S_{11}$ in dB) is a measure of reflected power measured at antenna feed divided by the incident power at the antenna feed, which it may be used as a power transfer measurement. In one embodiment of the invention, an antenna has an optimal coupling value may be, for example, −15 dB or below, which corresponds to 97% power return loss. At 97% power coupling, 97% of the input power available to the antenna (e.g. from a microwave generator) is coupled into the antenna's input port. Alternatively, in one embodiment of the invention, an antenna has an optimal coupling value of, for example, −10 dB or below, which corresponds to 90% power coupling. Alternatively, in one embodiment of the invention, an antenna has an optimal coupling value which may be, for example, −7 dB or below, which corresponds to 80% power coupling. In one embodiment of the invention, an antenna, such as, for example, a wave guide antenna may include tuning screws. In one embodiment of the invention, tuning screws may be used to, for example, optimize the return loss (magnitude of $S_{11}$) for the expected load.

In one embodiment of the invention, an antenna is optimized to maintain the power coupled into the antenna with a return of −10 dB or better over an optimal frequency band. An optimal bandwidth may be, for example, approximately 0.25 GHz (0.125 GHz on either side of the center frequency), at frequencies of interest, such as, for example, 5.8 GHz. An optimal bandwidth may be, for example, approximately 1.0 GHz (0.5 GHz on either side of the center frequency), at frequencies of interest, such as, for example, 5.8 GHz.

Dielectric Filler

In embodiments of the invention, dielectric filler may have a dielectric constant of approximately 10. In embodiments of the invention, dielectric filler may have a dielectric constant of between approximately 9.7 and 10.3. In embodiments of the invention, dielectric filler may be impervious to fluid, including cooling fluid in cooling chamber. In embodiments of the invention, dielectric filler may be configured to prevent liquid from entering waveguide tubing. In embodiments of the invention, dielectric filler may be configured to efficiently couple energy from an antenna feed into tissue. In embodiments of the invention, dielectric filler may be configured to match a waveguide tubing, coolant chamber, including cooling fluid and skin at a predetermined frequency of, for example frequencies in the range of: between approximately 4 GHz and 10 GHz; between approximately 5 GHz and 6.5 GHZ; or frequencies of approximately 5.8 GHz. In embodiments of the invention, dielectric filler may be configured to generate a field having minimal electric field perpendicular to a tissue surface. In embodiments of the invention, dielectric filler may be configured to generate a TE, $TE_{10}$, or TEM field in target tissue frequencies in the range of: between approximately 4 GHz and 10 GHz; between approximately 5 GHz and 6.5 GHZ; or frequencies of approximately 5.8 GHz.

In one embodiment of the invention, a waveguide fabricated using a cross sectional inner geometry, such as, for example, the cross-sectional inner geometry of a WR62 waveguide tube, having a width of 15.8 millimeters and a height of 7.9 millimeters is optimized at a predetermined frequency by selecting an appropriate dielectric filler. In one embodiment of the invention, an antenna, such as a waveguide antenna fabricated using a WR62 waveguide tube, is optimized at a predetermined frequency by selecting an appropriate filler material. In one embodiment of the invention, an antenna, such as a waveguide antenna fabricated using a wr62 waveguide tube, is optimized at a predetermined frequency by selecting a filler material having a dielectric constant in the range of between 3 and 12. In one embodiment of the invention, an antenna, such as a waveguide antenna fabricated using a wr62 waveguide tube, is optimized at a predetermined frequency by selecting a filler material having a dielectric constant of approximately 10. In one embodiment of the invention, an antenna, such as a waveguide antenna fabricated using a wr62 waveguide tube, is optimized at a predetermined frequency by selecting a dielectric filler material which is impervious to fluids, such as, for example cooling fluids. In one embodiment of the invention, an antenna, such as a waveguide antenna fabricated using a wr62 waveguide tube, is optimized at a predetermined frequency by selecting a dielectric filler material which is, for example, Eccostock. In one embodiment of the invention, an antenna, may be optimized at a predetermined frequency by selecting a dielectric filler material which is, for example, polycarbonate, Teflon, plastic or air.

Field Spreader

In one embodiment of the invention, an antenna may include a dielectric element, which may be referred to as a field spreader, at the antenna output that perturbs or scatters the microwave signal in such a way that the E-field is applied to tissue over a wider area. In one embodiment of the invention, the field spreader causes the E-field to diverge as it exits the antenna. In one embodiment of the invention, a field spreader may have a dielectric constant of between 1 and 80. In one embodiment of the invention, a field spreader may have a dielectric constant of between 1 and 15. In embodiments of the invention, field spreaders may be used to, for example, spread and flatten peak SAR regions, peak temperature regions or peak power loss density regions in tissue. In embodiments of the invention, field spreaders may be used to, for example, spread and flatten lesions in tissue.

In one embodiment of the invention, a field spreader may be a dielectric element. In one embodiment of the invention, a field spreader may be configured to spread an E-field. In one embodiment of the invention, a field spreader may be configured to extend from an output of an antenna to a cooling plate. In one embodiment of the invention, a field spreader may be configured to extend from a dielectric filler to a cooling plate. In one embodiment of the invention, a field spreader may be positioned at least partially in a cooling chamber. In one embodiment of the invention, a field spreader may be positioned at least partially in a cooling fluid. In one embodiment of the invention, a field spreader may be configured to have rounded features. In one embodiment of the invention, a field spreader may be oval. In one embodiment of the invention, a field spreader positioned at least partially in a cooling fluid may have a contoured shape. In one embodiment of the invention, a field spreader positioned at least partially in a cooling fluid may be configured to prevent eddy currents in the cooling fluid. In one embodiment of the invention, a field spreader positioned at least partially in a cooling fluid may be configured to prevent air bubbles from forming in the cooling fluid. In one embodiment of the invention, a system may have multiple field spreaders.

In one embodiment of the invention, a field spreader may be configured to have a dielectric constant which matches a dielectric filler. In one embodiment of the invention, a field spreader may be configured to have a dielectric constant which differs from a dielectric filler. In one embodiment of the invention, a field spreader may be configured to increase the effective field size (EFS) by reducing field strength in the center of a waveguide. In one embodiment of the invention, field spreader may be configured to increase the ratio of 50% SAR contour area at depth in a cross section of the target tissue compared to the surface area of the radiating aperture by, for example, reducing field strength in center of a waveguide. In one embodiment of the invention, field spreader may be configured to increase the lateral size of 50% SAR contour area at depth in a cross section of in the target tissue compared to the surface area of the radiating aperture by, for example, reducing field strength in the center of a waveguide. In one embodiment of the invention, a field spreader may be configured to cause a signal emitted from an antenna to diverge around the field spreader creating local E-field peaks that re-combine. In one embodiment of the invention, a field spreader may be configured to cause a signal emitted from an antenna to diverge around the field spreader creating local E-field peaks that re-combine to form larger peak power loss density, SAR or tissue temperature regions in adjacent tissue. In one embodiment of the invention, a field spreader may be configured to cause a signal emitted from an antenna to diverge around the field spreader creating local E-field peaks that re-combine to laterally enlarge lesions in adjacent tissue. In one embodiment of the invention, a field spreader may be configured to cause a signal emitted from an antenna to diverge around the field spreader creating local E-field peaks that re-combine to form laterally enlarged peak power loss density, SAR or tissue temperature regions in adjacent tissue. In one embodiment of the invention, a field spreader may be configured to cause a signal emitted from an antenna to diverge around the field spreader creating local E-field peaks that re-combine to form laterally enlarged lesions in adjacent tissue. In one embodiment of the invention, a field spreader may have a cross sectional which is between approximately two percent and 50 percent of the inner face of a waveguide antenna. In one embodiment of the invention, the field spreader may have a rectangular cross section. In one embodiment of the invention, the field spreader may have a rectangular cross section of 6 millimeters by 10 millimeters. In one embodiment of the invention, the field spreader may have a rectangular cross section of 6 millimeters by 10 millimeters when used with a waveguide having an inner face of 15.8 millimeters by 7.9 millimeters. In one embodiment of the invention, a field spreader may have a rectangular cross section of approximately 60 square millimeters. In one embodiment of the invention, a field spreader may have a rectangular cross section of approximately 60 square millimeters when used with a waveguide having an inner face with an area of approximately 124 square millimeters. In one embodiment of the invention, the field spreader may be comprised of, for example, alumina, having a dielectric constant of, for example 10. In one embodiment of the invention, a field spreader may be configured to consist of a dielectric region embedded in a waveguide. In one embodiment of the invention, a field spreader may be configured to consist of a dielectric region positioned in a cooling chamber. In one embodiment of the invention, a field spreader may be configured to consist of a notch in dielectric filler. In one embodiment of the invention, a field spreader may be configured to consist of a notch in dielectric filler which is configured to allow cooling fluid, such as, for example, water to flow in the notch. In one embodiment of the invention, a field spreader may be configured to consist of cooling fluid. In one embodiment of the invention, a field spreader may be configured to consist of one or more air gaps. In one embodiment of the invention, a field spreader may be positioned in the center of an aperture of an adjacent antenna. In one embodiment of the invention, a field spreader may comprise multiple field spreaders. In one embodiment of the invention, a field spreader may have a racetrack or ovoid shape. In one embodiment of the invention, a field spreader may have a racetrack shape and a length of, for example, 7 millimeters. In one embodiment of the invention, a field spreader may have a racetrack shape and a width of, for example, 4 millimeters.

Efficiency/Fringing

In one embodiment of the invention, an antenna, such as, for example, a waveguide antenna, is optimized to reduce or eliminate free space radiation due to fringing fields. In one embodiment of the invention, an antenna, such as, for example, a waveguide antenna, is optimized to redirect fringing fields towards tissue. In one embodiment of the invention, an antenna, such as, for example, a waveguide antenna is optimized to improve the efficiency of the antenna, which efficiency may be measured by, for example comparing the energy available at the input of the antenna to the energy which is coupled into adjacent tissue. In one embodiment of the invention, an antenna, such as, for example, a waveguide antenna is optimized to improve the efficiency of the antenna such that at least seventy percent of the energy available at the input of the antenna is deposited in tissue adjacent to an output of the antenna. In one embodiment of the invention, an antenna, such as, for example, a waveguide antenna, may be optimized by positioning the output of the antenna such that at lease an outer edge of the waveguide tube of the waveguide antenna is in contact with fluid. In one embodiment of the invention, an antenna, such as, for example, a waveguide antenna, may be optimized by positioning the output of the antenna such that the output of the antenna is in contact with fluid. In one embodiment of the invention, an antenna, such as, for example, a waveguide antenna, may be optimized by positioning the output of the antenna such that an output of the antenna is covered by an insulator which separates the output from a fluid, the insulator having a thickness which reduces the free space radiation due to the fringing fields at the output of the waveguide. In one embodiment of the invention, an antenna, such as, for example, a waveguide antenna, may be optimized by positioning the output of the antenna such that an output of the antenna is covered by an insulator which separates the output from a fluid, such as, for example, a cooling fluid the insulator having a thickness of less than 0.005". In one embodiment of the invention power transfer from an antenna, such as, for example, a waveguide antenna, through a cooling fluid and into adjacent tissue is optimized by reducing the thickness of an isolation layer between the output of the antenna and the cooling fluid. In one embodiment of the invention power transfer from an antenna, such as, for example, a waveguide antenna, through a cooling fluid and into adjacent tissue is optimized by placing the output of the antenna into the cooling fluid. In one embodiment of the invention an antenna, such as, for example, a waveguide antenna, may be optimized by covering the output of the antenna with an insulator, such as, for example, polycarbonate having a dielectric constant which is less than a dielectric constant of an antenna filler material. In one embodiment of the invention an antenna, such as, for example, a waveguide antenna, may be optimized by covering the output of the antenna with an insulator, such as, for example, polycarbonate having a dielectric constant which is less than a dielectric constant of an antenna filler material, the thickness of the insulator being between approximately 0.0001" and 0.006". In one embodiment of the invention an antenna, such as, for example, a waveguide antenna, may be optimized by covering the output of the antenna with an insulator the thickness of the insulator being between approximately 0.015". In one embodiment of the invention an antenna, such as, for example, a waveguide antenna, may be optimized by covering the output of the antenna with an insulator, such as, for example, polycarbonate having a dielectric constant which is less than a dielectric constant of an antenna filler material, the thickness of the insulator being between approximately 0.0001" and 0.004". In one embodiment of the invention an antenna, such as, for example, a waveguide antenna, may be optimized by covering the output of the antenna with an insulator, such as, for example, polycarbonate having a dielectric constant which is less than a dielectric constant of an antenna filler material, the thickness of the insulator is approximately 0.002". In one embodiment of the invention an antenna, such as, for example, a waveguide antenna, may be optimized by covering the output of the antenna with an insulator, such as, for example, alumina having a dielectric constant which is substantially equal to the a dielectric constant of an antenna filler material.

Polarization

In one embodiment of the invention, an antenna may be optimized by, for example, optimizing the design of the antenna to ensure that the antenna radiates in a TE mode. In one embodiment of the invention, an antenna may be optimized by, for example, optimizing the design of the antenna to ensure that the antenna radiates in a TEM mode. In one embodiment of the invention, an antenna, such as, for example, a waveguide antenna may be optimized by, for example, optimizing the design of the antenna to ensure that the antenna radiates in a substantially pure $TE_{10}$ mode.

Cooling System

In one embodiment of the invention, a cooling system is placed between a device adapted to emit electromagnetic radiation and skin. In one embodiment of the invention, a cooling system includes a cooling fluid and a cooling plate. In one embodiment of the invention, a cooling system includes a cooling fluid flowing past a cooling plate. In one embodiment of the invention, a cooling fluid flows through a cooling chamber. In one embodiment of the invention, a cooling fluid flows through a cooling chamber which is positioned between a device adapted to emit electromagnetic radiation and a cooling plate. In one embodiment of the invention, a cooling system includes a tissue interface. In one embodiment of the invention, a cooling system may be incorporated into a tissue head. Other cooling systems and various components that may be used with systems and devices described herein are described and illustrated, for example, at FIGS. 33-36 and pp. 40-45 of U.S. Provisional App. No. 60/912,899; and FIGS. 11A-11B and pp. 21-24 of U.S. Provisional App. No. 61/013,274 both incorporated by reference in their entireties, as well as illustrated and described, for example, in FIGS. 33-36 and pp. 42-46 of Appendix 1 and FIGS. 11A-11B and pp. 27-29 of Appendix 2.

Temperature

In one embodiment of the invention, a cooling system is optimized to maintain skin surface at a predetermined temperature. In one embodiment of the invention, a cooling system is optimized to maintain skin surface at a temperature of less than 45° C. In one embodiment of the invention, a cooling system is optimized to maintain skin surface at a temperature of less than 40° C. In one embodiment of the invention, a cooling system is optimized to maintain skin surface at a temperature of approximately 22° C. In one embodiment of the invention, a cooling system is optimized to maintain a cooling plate at a temperature of less than 40° C. In one embodiment of the invention, a cooling system is optimized to maintain skin surface at a temperature of less than 45° C. In one embodiment of the invention, cooling fluid is used remove heat from the cooling system.

Cooling Fluid

In one embodiment of the invention, moving cooling fluid is used to remove heat from the cooling system. In one embodiment of the invention, cooling fluid has a temperature of between −5° C. and 40° C. as it enters a cooling chamber in the cooling system. In one embodiment of the invention, cooling fluid has a temperature of between 10 and 25° C. as it enters a cooling chamber in the cooling system. In one embodiment of the invention, cooling fluid has a temperature of approximately 22° C. as it enters a cooling chamber in the cooling system. In one embodiment of the invention, cooling fluid has a flow rate of at least 100 milliliters per second as it moves through a cooling chamber. In one embodiment of the invention, cooling fluid has a flow rate of between 250 and 450 milliliters per second as it moves through a cooling chamber. In one embodiment of the invention, cooling fluid has a velocity of between 0.18 and 0.32 meters per second as it moves through a cooling chamber. In one embodiment of the invention, coolant flow in a cooling chamber is non-laminar. In one embodiment of the invention, coolant flow in a cooling chamber is turbulent to facilitate heat transfer. In one embodiment of the invention, cooling fluid has a Reynolds number of between approximately 1232 and 2057 prior to entering a cooling chamber. In one embodiment of the invention, cooling fluid has a Reynolds number of between approximately 5144 and 9256 prior to entering a cooling chamber.

In one embodiment of the invention, cooling fluid is optimized to be substantially transparent to microwave energy. In one embodiment of the invention, cooling fluid is optimized to minimize absorption of electromagnetic energy. In one embodiment of the invention, cooling fluid is optimized to match an antenna to tissue. In one embodiment of the invention, cooling fluid is optimized to facilitate the efficient transfer of microwave energy to tissue. In one embodiment of the invention, cooling fluid is optimized to conduct heat away from the surface of skin. In one embodiment of the invention, cooling fluid is comprised of a fluid having a high dielectric constant. In one embodiment of the invention, a cooling fluid is optimized to have a high dielectric constant of between 70 and 90. In one embodiment of the invention, a cooling fluid is optimized to have a high dielectric constant of approximately 80. In one embodiment of the invention, a cooling fluid is optimized to have a low dielectric constant of between 2 and 10. In one embodiment of the invention, a cooling fluid is optimized to have a low dielectric constant of approximately 2. In one embodiment of the invention, a cooling fluid is optimized to have a dielectric constant of approximately 80. In one embodiment of the invention, cooling fluid is comprised, at least in part, of de-ionized water. In one embodiment of the invention, cooling fluid is comprised, at least in part, of alcohol. In one embodiment of the invention, cooling fluid is comprised, at least in part, of ethylene glycol. In one embodiment of the invention, cooling fluid is comprised, at least in part, of glycerol. In one embodiment of the invention, cooling fluid is comprised, at least in part, of a germicide. In one embodiment of the invention, cooling fluid is comprised, at least in part of vegetable oil. In one embodiment of the invention, cooling fluid is comprised of a fluid having a low electrical conductivity. In one embodiment of the invention, cooling fluid is comprised of a fluid having an electrical conductivity of less than approximately 0.5 siemens per meter.

Cooling Plate

In embodiments of the invention, a cooling plate may be, for example configured to contact skin. In embodiments of the invention, a cooling plate may be, for example configured cool skin tissue. In embodiments of the invention, a cooling plate may be, for example configured to physically separate skin tissue from a microwave antenna. In embodiments of the invention, a cooling plate may be, for example configured to conform to the hair bearing region of the axilla of a human In embodiments of the invention, a cooling plate may be, for example configured to constitute a thermoelectric cooler In embodiments of the invention, a cooling plate may be, for example configured to be thermally conductive In embodiments of the invention, a cooling plate may be, for example configured to be substantially transparent to microwave energy. In embodiments of the invention, a cooling plate may be, for example configured to be thin enough to minimize microwave reflection. In embodiments of the invention, a cooling plate may be, for example configured to be composed of ceramic In embodiments of the invention, a cooling plate may be, for example configured or to be composed of alumina.

In one embodiment of the invention, a cooling plate is optimized to conduct electromagnetic energy to tissue. In one embodiment of the invention, a cooling plate is optimized to conduct heat from the surface of skin into a cooling fluid. In one embodiment of the invention, a cooling plate is optimized to have a thickness of between 0.0035" and 0.025", and may include thickness of up to 0.225". In one embodiment of the invention, a cooling plate is optimized to have a dielectric constant of between 2 and 15. In one embodiment of the invention, a cooling plate is optimized to have a dielectric constant of approximately 10. In one embodiment of the invention, a cooling plate is optimized to have a low electrical conductivity. In one embodiment of the invention, a cooling plate is optimized to have an electrical conductivity of less than 0.5 siemens per meter. In one embodiment of the invention, a cooling plate is optimized to have a high thermal conductivity. In one embodiment of the invention, a cooling plate is optimized to have a thermal conductivity of between 18 and 50 Watts per meter-Kelvin at room temperature. In one embodiment of the invention, a cooling plate is optimized to have a thermal conductivity of between 10 and 100 Watts per meter-Kelvin at room temperature. In one embodiment of the invention, a cooling plate is optimized to have a thermal conductivity of between 0.1 and 5 Watts per meter-Kelvin at room temperature. In one embodiment of the invention, a cooling plate is comprised, at least in part, of a ceramic material. In one embodiment of the invention, a cooling plate is comprised, at least in part, of alumina.

In one embodiment of the invention, a cooling plate may be, for example, a thin film polymer material. In one embodiment of the invention, a cooling plate may be, for example, a polyimide material. In one embodiment of the invention, a cooling plate may be, for example, a material having a conductivity of approximately 0.12 Watts per meter-Kelvin and a thickness of between approximately 0.002" and 0.010".

Cooling Chamber

In one embodiment of the invention, a cooling chamber has a thickness which is optimized for the electromagnetic radiation frequency, cooling fluid composition and cooling plate composition. In one embodiment of the invention, a cooling chamber has a thickness which is optimized for a high dielectric cooling fluid. In one embodiment of the invention, a cooling chamber has a thickness which is optimized for a cooling fluid having a dielectric constant of approximately 80, such as, for example, de-ionized water. In one embodiment of the invention, a cooling chamber has a thickness of between 0.5 and 1.5 millimeters. In one embodiment of the invention, a cooling chamber has a thickness of approximately 1.0 millimeters. In one embodiment of the invention, a cooling chamber has a thickness which is optimized for a low dielectric cooling fluid. In one embodiment of the invention, a cooling chamber has a thickness which is optimized for a cooling fluid which has a dielectric constant of approximately 2, such as, for example, vegetable oil. Low dielectric, low conductivity cooling fluids may be advantageous where it is desirable to limit the losses or to match elements. In one embodiment of the invention, a cooling chamber is optimized such that eddy currents are minimized as fluid flows through the cooling chamber. In one embodiment of the invention, a cooling chamber is optimized such that air bubbles are minimized as fluid flows through the cooling chamber. In one embodiment of the invention, field spreaders located in the cooling chamber are positioned and designed to optimize laminar flow of cooling fluid through the cooling chamber. In one embodiment of the invention, field spreaders located in the cooling chamber are substantially oval in shape. In one embodiment of the invention, field spreaders located in the cooling chamber are substantially round in shape. In one embodiment of the invention, field spreaders located in the cooling chamber are substantially rectangular in shape.

Thermoelectric Module

In one embodiment of the invention, a cooling system optimized to maintain the skin surface at a predetermined temperature may be, for example a thermoelectric module. In one embodiment of the invention, a cooling system is optimized to maintain the skin surface at a predetermined temperature by attaching the cold plate side of a thermoelectric cooler(s) (TEC) to a face of the cooling plate adjacent to the waveguide antenna(s). The hot side of the TEC(s) is attached to a finned heat sink(s) that is acted upon by an axial fan(s) in order to maintain the hot side of the TEC(s) at a low temperature to optimize the cooling performance of the TEC(s). The attachment of the TEC(s) to the cooling plate and heat sink(s) utilizes ceramic thermal adhesive epoxy. For example, the TEC(s) may be part number 06311-5L31-03CFL, available from Custom Thermoelectric, the heat sink(s) may be part number 655-53AB, available from Wakefield Engineering, the ceramic thermal adhesive epoxy may be available from Arctic Silver and the axial fans(s) may be part number 1608KL-04W-B59-L00 available from NMB-MAT.

In one embodiment of the invention, a cooling system is optimized to maintain the skin surface at a predetermined temperature by constructing the cold plate side of a thermoelectric cooler(s) (TEC) as the cooling plate adjacent to or surrounding the waveguide antenna(s) with an opening(s) in the hot side of the TEC(s) where the waveguide antenna(s) exist. The hot side of the TEC(s) is attached to a finned heat sink(s) that is acted upon by an axial fan(s) in order to maintain the hot side of the TEC(s) at a low temperature to optimize the cooling performance of the TEC(s). The attachment of the TEC(s) to the heat sink(s) utilizes ceramic thermal adhesive epoxy. For example, the TEC(s) may be available from Laird Technology, the heat sink(s) may be part number 655-53AB, available from Wakefield Engineering, the ceramic thermal adhesive epoxy may be available from Arctic Silver and the axial fans(s) may be part number 1608KL-04W-B59-L00 available from NMB-MAT.

In one embodiment of the invention, a cooling system is optimized to maintain the skin surface at a predetermined temperature by attaching the cold plate side of a thermoelectric cooler(s) (TEC) to a side(s) of the waveguide antenna(s). The hot side of the TEC(s) is attached to a finned heat sink(s) that is acted upon by an axial fan(s) in order to maintain the hot side of the TEC(s) at a low temperature to optimize the cooling performance of the TEC(s). The attachment of the TEC(s) to the waveguide antenna(s) and heat sink(s) utilizes ceramic thermal adhesive epoxy. For example, the TEC(s) may be part number 06311-5L31-03CFL, available from Custom Thermoelectric, the heat sink(s) may be part number 655-53AB, available from Wakefield Engineering, the ceramic thermal adhesive epoxy may be available from Arctic Silver and the axial fans(s) may be part number 1608KL-04W-B59-L00 available from NMB-MAT.

Energy

In one embodiment of the invention, energy is delivered to the skin for a period of time which optimizes the desired tissue effect. In one embodiment of the invention, energy is delivered to the skin for a period of between 3 and 4 seconds. In one embodiment of the invention, energy is delivered to the skin for a period of between 1 and 6 seconds. In one embodiment of the invention, energy is delivered to a target region in tissue. In one embodiment of the invention energy delivered to the target region for a time sufficient to result in an energy density at the target tissue of between 0.1 and 0.2 Joules per cubic millimeter. In one embodiment of the invention energy delivered to the target region for a time sufficient to heat the target tissue to a temperature of at least 75° C. In one embodiment of the invention energy delivered to the target region for a time sufficient to heat the target tissue to a temperature of between 55 and 75° C. In one embodiment of the invention energy delivered to the target region for a time sufficient to heat the target tissue to a temperature of at least 45° C.

Cooling

In one embodiment of the invention, the skin surface is cooled for a period of time which optimizes the desired tissue effect. In one embodiment of the invention, the skin surface is cooled during the time energy is delivered to the skin. In one embodiment of the invention, the skin surface is cooled for a period of time prior to the time energy is delivered to the skin. In one embodiment of the invention, the skin surface is cooled for a period of between 1 and 5 seconds prior to the time energy is delivered to the skin. In one embodiment of the invention, the skin surface is cooled for a period of approximately 2 seconds prior to the time energy is delivered to the skin. In one embodiment of the invention, the skin surface is cooled for a period of time after to the time energy is delivered to the skin. In one embodiment of the invention, the skin surface is cooled for a period of between 10 and 20 seconds after the time energy is delivered to the skin. In one embodiment of the invention, the skin surface is cooled for a period of approximately 20 seconds after the time energy is delivered to the skin.

Output Power

In one embodiment of the invention, power is delivered to a device adapted to radiate electromagnetic energy. In one embodiment of the invention, power is delivered to an input to an antenna, such as, for example, the feed to a waveguide antenna. In one embodiment of the invention, the power available at the antenna's input port is between 50 and 65 Watts. In one embodiment of the invention, the power available at the antenna's input port is between 40 and 70 Watts. In one embodiment of the invention, power available at the antenna's input port varies over time.

Tissue Acquisition

In one embodiment of the invention, skin is held in an optimal position with respect to an energy delivery device. In one embodiment of the invention, skin is held in an optimal position with respect to an energy delivery device using vacuum pressure. In one embodiment of the invention, skin is held in an optimal position with respect to an energy delivery device using vacuum pressure of between 400 and 750 millimeters of mercury. In one embodiment of the invention, skin is held in an optimal position with respect to an energy delivery device using vacuum pressure of approximately 650 millimeters of mercury. Other tissue acquisition systems, methods, and devices that can be used with embodiments of the invention to hold the skin in place and/or protect non-target tissue structures can be found, for example, at FIGS. 38-52C and pp. 46-57 of U.S. Provisional App. No. 60/912,899; and FIGS. 12-16B and pp. 24-29 of U.S. Provisional App. No. 61/013,274 both incorporated by reference in their entireties, as well as illustrated and described, for example, in FIGS. 38-52C and pp. 46-55 of Appendix 1 and FIGS. 12-16B and pp. 29-33 of Appendix 2.

Tissue Interface

Tissue Chamber

In one embodiment of the invention, a tissue chamber may be, for example, a suction chamber. In one embodiment of the invention, a tissue chamber may be configured to acquire at least a portion of the skin tissue. In one embodiment of the invention, a tissue chamber may be operatively coupled to a vacuum source. In one embodiment of the invention, a tissue chamber may be configured with at least one tapered wall. In one embodiment of the invention, a tissue chamber may be configured to at least partially acquire skin tissue and bring skin tissue in contact with cooling plate. In one embodiment of the invention, tissue chamber may be configured to include at least one suction element. In one embodiment of the invention, tissue chamber may be configured to elevate skin and placing skin in contact with a cooling element. In one embodiment of the invention, tissue chamber may be configured to elevate skin and placing skin in contact with a cooling element. In one embodiment of the invention, tissue chamber may be configured to elevate skin and placing skin in contact with a suction chamber. In one embodiment of the invention, tissue chamber may be configured to elevate skin and placing skin in contact with suction openings. In one embodiment of the invention, suction openings may include at least one channel wherein the channel may have rounded edges. In one embodiment of the invention, tissue chamber may have an ovoid or racetrack shape wherein the tissue chamber includes straight edges perpendicular to direction of cooling fluid flow. In one embodiment of the invention, tissue chamber may be configured to elevate skin separating skin tissue from underlying muscle tissue. In one embodiment of the invention, tissue chamber may be configured to include at least one temperature sensor. In one embodiment of the invention, tissue chamber may be configured to include at least one temperature sensor wherein the temperature sensor may be a thermocouple. In one embodiment of the invention, tissue chamber may be configured to include at least one temperature sensor wherein the temperature sensor is configured to monitor the temperature at skin surface. In one embodiment of the invention, tissue chamber may be configured to include at least one temperature sensor wherein the temperature sensor is configured such that it dose not significantly perturb a microwave signal.

In one embodiment of the invention, a tissue interface may comprise a tissue chamber which is optimized to separate skin from underlying muscle. In one embodiment of the invention, a tissue interface may comprise a vacuum chamber which is optimized to separate skin from underlying muscle when skin is pulled into a tissue chamber by, for example, vacuum pressure. In one embodiment of the invention, a tissue chamber may be optimized to have a depth of between approximately 1 millimeter and approximately 30 millimeters. In one embodiment of the invention, a tissue chamber may be optimized to have a depth of approximately 7.5 millimeters. In one embodiment of the invention, walls of a tissue chamber may be optimized to have an angle of between approximately 2 and 45 degrees. In one embodiment of the invention, walls of a tissue chamber may be optimized to have a chamber angle Z of between approximately 5 and 20 degrees. In one embodiment of the invention, walls of a tissue chamber may be optimized to have a chamber angle Z of approximately 20°. In one embodiment of the invention, a tissue chamber may be optimized to have an ovoid shape. In one embodiment of the invention, a tissue chamber may be optimized to have a racetrack shape. In one embodiment of the invention, a tissue chamber may be optimized to have an aspect ratio wherein the aspect ratio may be defined as the minimum dimension of a tissue interface surface to the height of the vacuum chamber. In the embodiment of the invention illustrated in FIG. 8, the aspect ratio may be, for example the ratio between minimum dimension 10 and tissue depth Y. In one embodiment of the invention, a tissue chamber may be optimized to have an aspect ratio of between approximately 1:1 and approximately 3:1. In one embodiment of the invention, a tissue chamber may be optimized to have an aspect ratio of approximately 2:1.

Staged Treatments

In some embodiments, it may be desirable to perform the treatment in stages. Additionally, the treatment may be patterned such that sections of target tissue are treated in the initial stage while other sections are treated in subsequent stages. Treatments using systems and devices disclosed herein may, for example, be treated in stages as disclosed in, for example, at FIGS. 54-57 and pp. 61-63 of U.S. Provisional App. No. 60/912,899; and FIGS. 17-19 and pp. 32-34 of U.S. Provisional App. No. 61/013,274 both incorporated by reference in their entireties, as well as illustrated and described, for example, in FIGS. 54-57 and pp. 58-60 of Appendix 1 and FIGS. 17-19 and pp. 36-38 of Appendix 2.

Diagnosis

Embodiments of the present invention also include methods and apparatuses for identifying and diagnosing patients with hyperhidrosis. Such diagnosis can be made based on subjective patient data (e.g., patient responses to questions regarding observed sweating), or objective testing. In one embodiment of objective testing, an iodine solution can be applied to the patient to identify where on a skin surface a patient is sweating and not sweating. Moreover, particular patients can be diagnosed based on excessive sweating in different parts of the body in order to specifically identify which areas to be treated. Accordingly, the treatment may be applied only selectively to different parts of the body requiring treatment, including, for example, selectively in the hands, armpits, feet and/or face.

Quantifying Treatment Success

Following completion of any of the treatments described above, or any stage of a treatment, the success can be evaluated qualitatively by the patient, or may be evaluated quantitatively by any number of ways. For example, a measurement can be taken of the number of sweat glands disabled or destroyed per surface area treated. Such evaluation could be performed by imaging the treated area or by determining the amount of treatment administered to the treated area (e.g. the quantity of energy delivered, the measured temperature of the target tissue, etc.). The aforementioned iodine solution test may also be employed to determine the extent of treatment effect. In addition, a treatment can be initiated or modified such that the amount of sweating experienced by a patient may be reduced by a desired percentage as compared to pre-treatment under defined testing criteria. For example, for a patient diagnosed with a particularly severe case of hyperhidrosis, the amount of sweating may be reduced by about 10%, 20%, 30%, 40%, 50%, 60%, 70%, 80%, 90% or more. For a patient diagnosed with a less severe or more normal sweating profile, a step-wise reduction of sweating may be achieved, but with less resolution. For example, such a patient may only be able to achieve partial anhidrosis in 25% increments.

Overview of Systems, Methods, and Devices

In one embodiment of the invention, a method of applying energy to tissue is described. In one embodiment of the invention, the method includes the step of generating a radiation pattern with a region of localized high power loss density in skin. In one embodiment of the invention, the method includes the step of generating a radiation pattern with a region of localized high power loss density in a region of the dermis adjacent a critical interface. In one embodiment of the invention, the method includes the step of generating a radiation pattern with a region of localized high power loss density in a glandular layer. In one embodiment of the invention, the method includes the step of generating a radiation pattern in skin with first and second regions of localized high power loss density wherein the first and second regions are separated by a region of low power loss density. In one embodiment of the invention, the method includes the step of generating a radiation pattern with a plurality of regions of localized high power loss density in skin wherein the first and second regions are separated by a region of low power loss density. In one embodiment of the invention, the method includes the step of generating a radiation pattern with a plurality of regions of localized high power loss density in skin wherein adjacent regions of high power loss density are separated by regions of low power loss density.

In one embodiment of the invention, a method of applying energy to tissue is described. In one embodiment of the invention, the method includes the step of generating a radiation pattern with a region of localized high specific absorption rate (SAR) in skin. In one embodiment of the invention, the method includes the step of generating a radiation pattern with a region of localized high specific absorption rate (SAR) in a region of the dermis adjacent a critical interface. In one embodiment of the invention, the method includes the step of generating a radiation pattern with a region of localized high specific absorption rate (SAR) in a glandular layer. In one embodiment of the invention, the method includes the step of generating a radiation pattern in skin with first and second regions of localized specific absorption rate (SAR) wherein the first and second regions are separated by a region of low specific absorption rate (SAR). In one embodiment of the invention, the method includes the step of generating a radiation pattern with a plurality of regions of localized high specific absorption rate (SAR) in skin wherein the first and second regions are separated by a region of low specific absorption rate (SAR). In one embodiment of the invention, the method includes the step of generating a radiation pattern with a plurality of regions of localized specific absorption rate (SAR) in skin wherein adjacent regions of high specific absorption rate (SAR) are separated by regions of low specific absorption rate (SAR).

In one embodiment of the invention, a method of applying energy to tissue is described. In one embodiment of the invention, the method includes the step of generating a radiation pattern with a region of localized high temperature in skin. In one embodiment of the invention, the method includes the step of generating a radiation pattern with a region of localized high temperature in a region of the dermis adjacent a critical interface. In one embodiment of the invention, the method includes the step of generating a radiation pattern with a region of localized high temperature in a glandular layer. In one embodiment of the invention, the method includes the step of generating a radiation pattern in skin with first and second regions of localized temperature wherein the first and second regions are separated by a region of low temperature. In one embodiment of the invention, the method includes the step of generating a radiation pattern with a plurality of regions of localized high temperature in skin wherein the first and second regions are separated by a region of low temperature. In one embodiment of the invention, the method includes the step of generating a radiation pattern with a plurality of regions of localized temperature in skin wherein adjacent regions of high temperature are separated by regions of low temperature.

In one embodiment of the invention, a method of aligning electromagnetic field to preferentially treat tissue having a relatively high water content is described. In one embodiment of the invention, the method includes the steps of irradiating tissue with an electromagnetic Electric field aligned with a surface of the skin. In one embodiment of the invention, the method includes irradiating tissue with electromagnetic radiation in the $TE_{10}$ mode. In one embodiment of the invention, the method includes irradiating tissue with electromagnetic radiation having a minimal E-field in a direction perpendicular to at least a portion of a skin surface. In one embodiment of the invention, the method includes aligning an E-field component of an electromagnetic wave to preferentially heat tissue having a high water content by irradiating with transverse electric (TE) or transverse electromagnetic (TEM) waves.

In one embodiment of the invention, a method for controlling the delivery of energy to tissue is described. In one embodiment of the invention, the method of delivering energy includes the step of delivering energy at a frequency of approximately 5.8 GHz. In one embodiment of the invention, the method of delivering energy includes the step of delivering energy having a power of greater than approximately 40 Watts. In one embodiment of the invention, the method of delivering energy includes the step of delivering energy for a period of between approximately 2 seconds and approximately 10 seconds. In one embodiment of the invention, the method of delivering energy includes the step of pre-cooling skin surface for a period of approximately 2 seconds. In one embodiment of the invention, the method of delivering energy includes the step of post cooling for a period of approximately 20 seconds. In one embodiment of the invention, the method of delivering energy includes the step of maintaining tissue engagement for a period of more than approximately 22 seconds. In one embodiment of the invention, the method of delivering energy includes the step of engaging tissue using a vacuum pressure of approximately 600 millimeters of mercury. In one embodiment of the invention, the method of delivering energy includes the step of measuring skin temperature. In one embodiment of the invention, the method of delivering energy includes the step of adjusting energy delivery duration; pre-cooling duration; post-cooling duration; output power; frequency; vacuum pressure as a result of feedback of tissue parameters such as, for example, skin temperature. In one embodiment of the invention, the method of delivering energy includes the step of adjusting energy delivery duration; pre-cooling duration; post-cooling duration; output power; frequency; vacuum pressure as a result of feedback of tissue parameters such as, for example, cooling fluid temperature.

In one embodiment of the invention, a method of removing heat from tissue is described. In one embodiment of the invention, a method of cooling tissue is described, the method including engaging the surface of the skin. In one embodiment of the invention, the method includes the step of positioning a cooling element in contact with the skin surface. In one embodiment of the invention, the method includes the step of conductively cooling the skin surface. In one embodiment of the invention, the method includes the step of convectively cooling the skin surface. In one embodiment of the invention, the method includes the step of conductively and convectively cooling the skin surface In one embodiment of the invention, a method of damaging or destroying tissue structures is described. In one embodiment of the invention, a method of damaging or destroying glands is described. In one embodiment of the invention the method includes the step of inducing hyperthermia in the tissue structures. In one embodiment of the invention, hyperthermia may be accomplished by mild heating of tissue to a temperature of, for example, between approximately 42° C. and 45° C. In one embodiment of the invention the method includes the step of ablating tissue structures may be accomplished by heating of tissue to temperatures in excess of approximately 47° C.

In one embodiment of the invention a method of treating tissue using electromagnetic radiation is described. In one embodiment of the invention a method of treating tissue includes creating a secondary effect in tissue. In one embodiment of the invention a method of treating tissue includes creating a secondary effect in tissue wherein the secondary effect includes, for example, reducing bacterial colonization. In one embodiment of the invention a method of treating tissue includes creating a secondary effect in tissue wherein the secondary effect includes clearing or reducing skin blemishes. In one embodiment of the invention a method of treating tissue includes creating a secondary effect in tissue wherein the secondary effect includes clearing or reducing skin blemishes resulting from, for example, acne vulgaris. In one embodiment of the invention a method of treating tissue includes damaging sebaceous glands. In one embodiment of the invention a method of treating tissue includes disabling sebaceous glands. In one embodiment of the invention a method of treating tissue includes temporarily disabling sebaceous glands.

In one embodiment of the invention, a method of delivering energy to selected tissue is described. In one embodiment of the invention, the method includes delivering energy via a microwave energy delivery applicator. In one embodiment of the invention, the method involves delivering energy sufficient to create a thermal effect in a target tissue within the skin tissue. In one embodiment of the invention, the method includes the step of delivering energy to tissue which is subject to dielectric heating. In one embodiment of the invention, the method includes the step of delivering energy to tissue having a high dielectric moment. In one embodiment of the invention, the method includes delivering energy to target tissue within the skin tissue selected from the group consisting of collagen, hair follicles, cellulite, eccrine glands, apocrine glands, sebaceous glands, spider veins and combinations thereof. In one embodiment of the invention, target tissue within the skin tissue comprises the interface between the dermal layer and subcutaneous layer of the skin tissue. In one embodiment of the invention, creating a thermal effect in the target tissue comprises thermal alteration of at least one sweat gland. In one embodiment of the invention, creating a thermal effect in the target tissue comprises ablation of at least one sweat gland.

In one embodiment of the invention, a method of delivering microwave energy to tissue is described. In one embodiment of the invention, the method includes the step of applying a cooling element to the skin tissue. In one embodiment of the invention, the method includes the step of applying microwave energy to tissue at a power, frequency and duration and applying cooling at a temperature and a duration sufficient to create a lesion proximate interface between the dermis layer and subcutaneous layer in the skin tissue while minimizing thermal alteration to non-target tissue in the epidermis and dermis layers of the skin tissue. In one embodiment of the invention, the method includes the step of applying microwave energy to a second layer of skin containing sweat glands sufficient to thermally alter the sweat glands. In one embodiment of the invention, the method includes the step of applying microwave energy while the first layer of skin is protectively cooled, the second layer being deeper than the first layer relative to the skin surface. In one embodiment of the invention, the method includes the step of cooling via a cooling element.

In one embodiment of the invention, the method includes the step of using one or more field spreaders to spread the MW energy as it emerges from an antenna. In one embodiment of the invention, the method includes creating a contiguous lesion larger than a single waveguide lesion. In one embodiment of the invention, the method includes the step of using multiple antennas. In one embodiment of the invention, the method includes the step of creating a contiguous lesion larger than a single waveguide lesion. In one embodiment of the invention, the method includes the step of using an array of waveguides. In one embodiment of the invention, the method includes the step of activating a plurality of waveguides in series. In one embodiment of the invention, the method includes the step of activating multiple antennas. In one embodiment of the invention, the method includes the step of activating less than all antennas in an array. In one embodiment of the invention, the method includes the step of continuously cooling under all antennas in an array.

In one embodiment of the invention, a method of applying energy to tissue is described. In one embodiment of the invention, the method includes the step of applying energy at a depth deeper than a skin surface. In one embodiment of the invention, the method includes the step of applying energy but not as deep as nerve or muscle tissue. In one embodiment of the invention, the method includes the step of applying electromagnetic radiation at a frequency which concentrates energy at target tissue In one embodiment of the invention, a method of selectively heating tissue is described. In one embodiment of the invention, the method includes the step of selectively heating tissue by dielectric heating. In one embodiment of the invention, the method includes the step of selectively heating glands. In one embodiment of the invention, the method includes the step of selectively heating glandular fluid. In one embodiment of the invention, the method includes the step of heating tissue to a temperature sufficient to damage a gland. In one embodiment of the invention, the method includes the step of heating the gland to a temperature sufficient to result in morbidity. In one embodiment of the invention, the method includes the step of heating the gland to a temperature sufficient to result in death. In one embodiment of the invention, the method includes the step of heating the gland to a temperature sufficient to damage adjacent hair follicles. In one embodiment of the invention, the method includes the step of heating the gland to a temperature sufficient to destroy adjacent hair follicles. In one embodiment of the invention, the method includes the step of heating the gland to a temperature sufficient to induce hyperthermia in tissue at the skin/fat interface. In one embodiment of the invention, the method includes the step of heating the gland to a temperature sufficient to induce hyperthermia in tissue at the skin/fat interface while minimizing hyperthermia in surrounding tissue. In one embodiment of the invention, the method includes the step of heating the gland to at least 50° C.

In one embodiment of the invention, a method of generating a temperature profile in skin tissue is described. In one embodiment of the invention the method includes generating a temperature profile having a peak in region directly above skin-fat interface. In one embodiment of the invention, the method includes the step of generating a temperature profile wherein the temperature declines towards the skin surface. In one embodiment of the invention, the method includes the step of generating a temperature profile wherein the temperature declines towards the skin surface in the absence of cooling.

In one embodiment of the invention, a method of positioning skin is described. In one embodiment of the invention, the method includes the step of using suction, pinching or adhesive. In one embodiment of the invention, the method includes the step of using suction, pinching or adhesive to lift a dermal and subdermal layer away from a muscle layer.

In one embodiment of the invention, a method of applying energy to tissue is described. In one embodiment of the invention, the method includes the step of placing a microwave energy delivery applicator over the skin tissue. In one embodiment of the invention, the microwave applicator includes a microwave antenna. In one embodiment of the invention, the microwave antenna is selected from the group consisting of: single slot, multiple slot, waveguide, horn, printed slot, patch, Vivaldi antennas and combinations thereof. In one embodiment of the invention, the method includes the step of positioning the microwave energy delivery applicator over a region having more absorptive tissue elements. In one embodiment of the invention, the method includes the step of positioning the microwave energy delivery applicator over a region having a concentration of sweat glands. In one embodiment of the invention, the method includes the step of positioning the microwave energy delivery applicator over a hair bearing area. In one embodiment of the invention, the method includes the step of positioning the microwave energy delivery applicator over an axilla. In one embodiment of the invention, the method includes the step of acquiring skin within a suction chamber. In one embodiment of the invention, the method includes the step of activating a vacuum pump. In one embodiment of the invention, the method includes the step of deactivating a vacuum pump to release skin. In one embodiment of the invention, the method includes the step of securing skin tissue proximate to the microwave energy delivery applicator. In one embodiment of the invention, the method includes the step of securing skin tissue proximate to the microwave energy delivery applicator by applying suction to the skin tissue. In one embodiment of the invention, the method includes the step of securing skin tissue proximate to the microwave energy delivery applicator includes the step of at least partially acquiring the skin tissue within a suction chamber adjacent to the energy delivery applicator. In one embodiment of the invention, the method includes the step of using a lubricant to enhance vacuum. In one embodiment of the invention, the method includes the step of securing skin tissue proximate to the microwave energy delivery applicator includes the step of elevating the skin tissue. In one embodiment of the invention, the method includes the step of securing skin tissue proximate to the microwave energy delivery applicator includes the step of brining skin in contact with cooling. In one embodiment of the invention, the method includes the step of activating a vacuum pump to acquire the skin within a suction chamber.

In one embodiment, disclosed herein is a system for the application of microwave energy to a tissue, including a signal generator adapted to generate a microwave signal having predetermined characteristics; an applicator connected to the generator and adapted to apply microwave energy to tissue, the applicator comprising one or more microwave antennas and a tissue interface; a vacuum source connected to the tissue interface; a cooling source connected to said tissue interface; and a controller adapted to control the signal generator, the vacuum source, and the coolant source. In some embodiments, the microwave signal has a frequency in the range of between about 4 GHz and about 10 GHz, between about 5 GHz and about 6.5 GHz, or about 5.8 GHz. The system can further comprise an amplifier connected between the signal generator and the applicator. The microwave antenna may comprise an antenna configured to radiate electromagnetic radiation polarized such that an E-field component of the electromagnetic radiation is substantially parallel to an outer surface of the tissue. In some embodiments, the microwave antenna comprises a waveguide antenna. The antenna may comprise an antenna configured to radiate in TE10 mode, and/or TEM mode. The tissue interface can be configured to engage and hold skin. The skin is of the axillary region in some embodiments. The microwave antenna may comprise an antenna configured to radiate electromagnetic radiation polarized such that an E-field component of the electromagnetic radiation is parallel to an outer surface of the tissue.

In some embodiments, the tissue interface comprises a cooling plate and a cooling chamber positioned between the cooling plate and the microwave antenna. In some embodiments, the cooling plate has a dielectric constant between about 2 and 15. The vacuum source can be configured to supply vacuum pressure to the tissue interface. In some embodiments, the vacuum pressure is between about 400 mmHg to about 750 mmHg, or about 650 mmHg in some embodiments. The cooling source can be configured to supply a coolant to the tissue interface. The coolant can be a cooling fluid, which in some embodiments has a dielectric constant of between about 70 and 90, about 80, between about 2 and 10, or about 2. In some embodiments, the cooling fluid can have a temperature of between about $-5°$ C. and $40°$ C., $10°$ C. and $25°$ C., or about $22°$ C. In some embodiments, the cooling fluid has a flow rate through at least a portion of the tissue interface of between about 100 mL and 600 mL per second, or between about 250 mL and 450 mL per second. In some embodiments, the cooling fluid is configured to flow through the tissue interface at a velocity of between 0.18 and 0.32 meters per second. The cooling fluid can be selected from, e.g., glycerin, vegetable oil, isopropyl alcohol, water, water mixed with alcohol, or other combinations in some embodiments. The cooling source may comprise a thermoelectric module. In some embodiments, the tissue comprises a first layer and a second layer, the second layer below the first layer, wherein the controller is configured such that the system delivers energy such that a peak power loss density profile is created in the second layer.

In another embodiment, disclosed is an apparatus for delivering microwave energy to target tissue, the apparatus comprising a tissue interface; a microwave energy delivery device; a cooling element positioned between the tissue interface and the microwave energy device, the cooling element comprising a cooling plate positioned at the tissue interface; and a cooling fluid positioned between the cooling element and the microwave delivery device, the cooling fluid having a dielectric constant greater than a dielectric constant of the cooling element. In some embodiments, the tissue interface comprises a tissue acquisition chamber, which can be a vacuum chamber in some embodiments. The cooling plate may be made of ceramic. In some embodiments, the cooling plate is configured to contact a skin surface about the target tissue, cool the skin tissue, and physically separate the skin tissue from the cooling fluid. In some embodiments, the microwave energy delivery device comprises a microwave antenna, which may be a waveguide antenna in some embodiments.

In another embodiment, disclosed is an apparatus for delivering microwave energy to a target region in tissue, the apparatus comprising: a tissue interface having a tissue acquisition chamber; a cooling element having a cooling plate; and a microwave energy delivery device having a microwave antenna. In some embodiments, the tissue acquisition chamber comprises a vacuum chamber adapted to elevate tissue, including the target region, and bring the tissue in contact with the cooling element. In some embodiments, the vacuum chamber has a racetrack shape comprising a first side and a second side, the first and second sides parallel to each other, and a first end and a second end, the first and second ends having arcuate shapes. In some embodiments, the cooling plate is configured to contact a skin surface above the target tissue, cool the skin tissue, and physically separate the skin tissue from the microwave energy delivery device. The cooling plate may be substantially transparent to microwave energy. In some embodiments, the microwave antenna is configured to deliver sufficient energy to the target region to create a thermal effect. In some embodiments, the microwave antenna comprises a waveguide antenna.

Also disclosed, in one embodiment, is an apparatus for delivering microwave energy to a target region in tissue, the apparatus comprising a vacuum chamber adapted to elevate tissue including the target region and bring the tissue into contact with a cooling plate, wherein the cooling plate is adapted to contact a skin surface above the target region, cool the skin surface, and physically separate the skin tissue from the microwave energy delivery device; and a microwave antenna configured to deliver sufficient energy to the target region to create a thermal effect. In some embodiments, the vacuum chamber may have a race track shape comprising a first side and a second side, the first and second sides parallel to each other; and a first end and a second end, the first and second ends having arcuate shapes. In some embodiments, the cooling plate is substantially transparent to microwave energy. In some embodiments, the microwave antenna is configured to deliver sufficient energy to the target region to create a thermal effect. In some embodiments, the microwave antenna comprises a waveguide antenna. In some embodiments, the microwave antenna is configured to generate a radiation pattern having a peak at the target region.

Also disclosed, in one embodiment, is a system for coupling microwave energy into tissue, the system comprising a microwave antenna, a fluid chamber positioned between the microwave antenna and the tissue, and a cooling plate positioned between the cooling chamber and the tissue. In one embodiment, the system further comprises at least one field spreader. The field spreader may be positioned within the fluid chamber between the waveguide and the cooling plate. The field spreader may be configured to facilitate laminar flow of fluid through the fluid chamber. In one embodiment, the field spreader may be configured to prevent one or more of eddy currents or air bubbles within the cooling fluid. In one embodiment, the system may further comprise a cooling fluid selected to maximize thermal transfer while minimizing microwave reflections. The cooling fluid may be selected from the group consisting of alcohol, glycerol, ethylene glycol, deionized water, a germicide, and vegetable oil. In one embodiment, the microwave antenna may a waveguide including a dielectric filler selected to generate a field having a minimal electric field perpendicular to a surface of the tissue at a predetermined frequency. In one embodiment, the fluid chamber has a shape configured to facilitate laminar flow of cooling fluid therethrough. The fluid chamber may be rectangular shaped. In some embodiments, the cooling plate is thermally conductive and substantially transparent to microwave energy.

In another embodiment, a method of creating a tissue effect in a target tissue layer is disclosed, comprising the steps of: irradiating the target tissue layer and a first tissue layer through a skin surface with electromagnetic energy having predetermined frequency and electric field characteristics, wherein the first tissue layer is above the target tissue layer, the first tissue layer being adjacent to a surface of the skin; and generating a power loss density profile, wherein the power loss density profile has a peak power loss density in a region of the target tissue layer. In one embodiment, the method further comprises the step of identifying a patient desiring a reduction in sweat production. In other embodiments, the method further comprises the step of identifying a patient desiring a reduction in cellulite, identifying a patient with hyperhidrosis, identifying a patient with telangiectasias, identifying a patient with varicose veins, or identifying a patient desiring hair removal. In another embodiment, the method further comprises the step of removing heat from the first tissue layer. In one embodiment, the method further comprises the step of removing heat from the tissue layer. In one embodiment, the tissue effect comprises a lesion. The lesion may have an origin in the target tissue layer. In one embodiment, the origin of the lesion is in the region of the target tissue layer having the peak power loss density. In one embodiment, the method further comprises the step of removing sufficient heat from the first layer to prevent the lesion from growing into the first layer, wherein the step of removing heat from the first tissue layer comprises cooling the skin surface. In one embodiment, the target tissue layer may comprise the dermis, a deep layer of the dermis, or a glandular layer. In one embodiment, the electromagnetic energy has an electric field component which is substantially parallel to at least a portion of the skin surface. The electromagnetic energy may have an electric field component which is parallel to at least a portion of the skin surface. In some embodiments, the electromagnetic energy radiates in a $TE_{10}$ mode or TEM mode. In some embodiments, the electromagnetic energy has a frequency in the range between about 4 GHz and 10 Ghz, between 5 GHz and 6.5 GHz, or approximately 5.8 GHz. In one embodiment, the electromagnetic energy generates heat in the target tissue by dielectric heating. In one embodiment, the power loss density is generated by a standing wave pattern in the target tissue layer and the first tissue layer. In one embodiment, the standing wave pattern has a constructive interference peak in the region of the target tissue layer. The standing wave pattern may have a constructive interference minimum in the first tissue layer.

In another embodiment, disclosed is a method of creating a lesion in a target tissue layer in the absence of cooling, wherein the target tissue layer is below a first tissue layer, the first tissue layer being adjacent to a skin surface, the method comprising the steps of: irradiating the target tissue layer and a first tissue layer through a skin surface with electromagnetic energy having predetermined frequency and electric field characteristics, wherein the first tissue layer is above the target tissue layer, the first tissue layer being adjacent to a surface of the skin; and generating a power loss density profile, wherein the power loss density profile has a peak power loss density in a region of the target tissue layer. In one embodiment, the lesion has an origin in the target tissue layer. In some embodiments, the target tissue layer comprises the dermis, a deep layer of the dermis, or a glandular layer. In one embodiment, the electromagnetic energy has an electric field component which is substantially parallel to at least a portion of the skin surface. In one embodiment, the electromagnetic energy has an electric field component which is substantially parallel to at least a portion of the skin surface. In one embodiment, the electromagnetic energy has an electric field component which is parallel to at least a portion of the skin surface. In some embodiments, the electromagnetic energy radiates in a $TE_{10}$ mode or a TEM mode. In some embodiments, the electromagnetic energy has a frequency in the range of between about 4 GHz and 10 GHz, 5 GHz and 6.5 GHz, or approximately 5.8 GHz. The electromagnetic energy may generate heat in the target tissue by dielectric heating. In one embodiment, the power loss density is generated by a standing wave pattern in the target tissue layer and the first tissue layer. The standing wave pattern may have a constructive interference peak in the region of the target tissue layer or in the first tissue layer. In one embodiment, the origin of the lesion is in the region of the target tissue layer having the peak power loss density.

In another embodiment, disclosed is a method of generating heat in a target tissue layer wherein the heat is sufficient to create a lesion in or proximate to the target tissue layer, wherein the target tissue layer is below a first tissue layer, the first tissue layer being adjacent to a skin surface, the method comprising the steps of: irradiating the target tissue layer and the first tissue layer through the skin surface with electromagnetic energy having predetermined frequency and electric field characteristics; and generating a power loss density profile wherein the power loss density profile has a peak power loss density in a region of the target tissue layer. In one embodiment, the lesion has an origin in the target tissue layer. In some embodiment, the target tissue layer comprises the dermis, a deep layer of the dermis or a glandular layer. In one embodiment, the method further comprises the step of removing heat from the first tissue layer. In one embodiment, the method further comprises the step of removing sufficient heat from the first layer to prevent the lesion from growing into the first layer, wherein the step of removing heat from the first tissue layer comprises cooling the skin surface. In some embodiment, the electromagnetic energy has an electric field component which is substantially parallel to at least a portion of the skin surface, while in other embodiments, the electric field component is parallel to at least a portion of the skin surface. In some embodiments, the electromagnetic energy radiates in a $TE_{10}$ mode or TEM mode. In some embodiments, the electromagnetic energy has a frequency in the range of between about 4 GHz and 10 GHz, 5 GHz and 6.5 GHz, or approximately 5.8 GHz. In one embodiment, the electromagnetic energy generates heat in the target tissue by dielectric heating. In one embodiment, the power loss density is generated by a standing wave pattern in the target tissue layer and the first tissue layer. In one embodiment, the power loss density is generated by a standing wave pattern in the target tissue layer and the first tissue layer. In some embodiments, the standing wave pattern has a constructive interference peak in the region of the target tissue layer or in the first tissue layer. In one embodiment, the origin of the lesion is in the region of the target tissue layer having the peak power loss density. In one embodiment, the heat is sufficient to destroy bacteria within the target tissue. In some embodiments, the method further comprises the step of identifying a patient with acne or identifying a patient desiring a reduction of sweat production.

In another embodiment, disclosed is a method of generating heat in a target tissue layer in the absence of cooling wherein the heat is sufficient to create a tissue effect in or proximate to the target tissue layer, wherein the target tissue layer is below a first tissue layer, the first tissue layer being adjacent to a skin surface, the method comprising the steps of: irradiating the target tissue layer and the first tissue layer through the skin surface with electromagnetic energy having predetermined frequency and electric field characteristics; and generating a power loss density profile wherein the power loss density profile has a peak power loss density in a region of the target tissue layer. In one embodiment, the heat is sufficient to generate a lesion having an origin in the target tissue layer. In some embodiments, the target tissue layer comprises the dermis, deep layer of the dermis or glandular layer. In one embodiment, the electromagnetic energy has an electric field component which is substantially parallel to at least a portion of the skin surface, while in another embodiment, the electric field component is parallel to at least a portion of the skin surface. In some embodiments, the electromagnetic energy radiates in a $TE_{10}$ mode or a TEM mode. In some embodiments, the electromagnetic energy has a frequency in the range of between about 4 GHz and 10 GHz, 5 GHz and 6.5 GHz, or about 5.8 GHz. In one embodiment, the electromagnetic energy generates heat in the target tissue by dielectric heating. In one embodiment, the power loss density is generated by a standing wave pattern in the target tissue layer and the first tissue layer. In some embodiments, the standing wave pattern has a constructive interference peak in the region of the target tissue layer or in the first tissue layer. In one embodiment, the standing wave pattern has a constructive interference minimum in the first tissue layer. In one embodiment, the origin of the lesion is in the region of the target tissue layer having the peak power loss density.

Also disclosed herein, in another embodiment is a method of generating a temperature profile in tissue wherein the temperature profile has a peak in a target tissue layer, wherein the target tissue layer is below a first tissue layer, the first tissue layer being adjacent to a skin surface, the method comprising the steps of: irradiating the target tissue layer and the first tissue layer through the skin surface with electromagnetic energy having predetermined frequency and electric field characteristics; and generating a power loss density profile wherein the power loss density profile has a peak power loss density in a region of the target tissue layer. In some embodiments, the target tissue layer comprises the dermis, a deep layer of the dermis or a glandular layer. In one embodiment, the method further comprises the step of removing heat from the first tissue layer. In one embodiment, the electromagnetic energy has an electric field component which is substantially parallel to at least a portion of the skin surface. In one embodiment, the electromagnetic energy has an electric field component which is parallel to at least a portion of the skin surface. In some embodiments, the electromagnetic energy radiates in a $TE_{10}$ mode or TEM mode. In some embodiments, the electromagnetic energy has a frequency in the range of between about 4 GHz and 10 GHz, between about 5 GHz and 6.5 GHz, or of approximately 5.8 GHz. In one embodiment, the electromagnetic energy generates heat in the target tissue by dielectric heating. In one embodiment, the power loss density is generated by a standing wave pattern in the target tissue layer and the first tissue layer. The standing wave pattern may have a constructive interference peak in the region of the target tissue layer. The standing wave pattern may have a constructive interference minimum in the first tissue layer. In one embodiment, the peak temperature is in the region of the target tissue layer having the peak power loss density.

In another embodiment, disclosed herein is a method of generating a temperature profile in tissue in the absence of cooling wherein the temperature profile has a peak in a target tissue layer, wherein the target tissue layer is below a first tissue layer, the first tissue layer being adjacent to a skin surface, the method comprising the steps of: irradiating the target tissue layer and the first tissue layer through the skin surface with electromagnetic energy having predetermined frequency and electric field characteristics; and generating a power loss density profile wherein the power loss density profile has a peak power loss density in a region of the target tissue layer. In some embodiments, the target tissue layer comprises the dermis, a deep layer of the dermis or a glandular layer. In some embodiments, the electromagnetic energy has an electric field component which is substantially parallel to at least a portion of the skin surface or which is parallel to at least a portion of the skin surface. In some embodiments, the electromagnetic energy radiates in a $TE_{10}$ mode or a TEM mode. In some embodiments, the electromagnetic energy has a frequency in the range of between about 4 GHz and 10 GHz, 5 GHz and 6.5 GHz or approximately 5.8 GHz. In one embodiment, the electromagnetic energy generates heat in the target tissue by dielectric heating. In one embodiment, the power loss density is generated by a standing wave pattern in the target tissue layer and the first tissue layer. The standing wave pattern may have a constructive interference peak in the region of the target tissue layer. The standing wave pattern may have a constructive interference minimum in the first tissue layer. In one embodiment, the peak temperature is in the region of the target tissue layer having the peak power loss density.

In another embodiment, disclosed is a method of creating a lesion in a first layer of tissue, the first layer having an upper portion adjacent an external surface of the skin and a lower portion adjacent a second layer of the skin, the method comprising the steps of: exposing the external surface of the skin to microwave energy having a predetermined power, frequency, and electric field orientation; generating an energy density profile having a peak in the lower portion of the first layer; and continuing to expose the external surface of the skin to the microwave energy for a time sufficient to create a lesion, wherein the lesion begins in the peak energy density region. In one embodiment, the first layer of skin has a first dielectric constant and the second layer of skin has a second dielectric constant, wherein the first dielectric constant is greater than the second dielectric constant. In one embodiment, the first layer has a dielectric constant greater than about 25 and the second layer has a dielectric constant less than or equal to about 10. In one embodiment, the first layer comprises at least a portion of a dermis layer. In some embodiments, the second layer comprises at least a portion of a hypodermis layer or at least a portion of a glandular layer.

Also disclosed herein is a method of creating a lesion in the skin wherein the skin has at least an external surface, a first layer below the external surface and a second layer, the method comprising the steps of: positioning a device adapted to radiate electromagnetic energy adjacent the external surface; radiating electromagnetic energy from the device, the microwave energy having an electric field component which is substantially parallel to a region of the external surface; and generating a standing wave pattern in the first layer, the standing wave pattern having a constructive interference peak in the first layer, wherein a distance from the constructive interference peak to the skin surface is greater than a distance from the constructive interference peak to an interface between the first layer and the second layer. In one embodiment, the electromagnetic energy comprises microwave energy. In one embodiment, the constructive interference peak is adjacent the interface. In one embodiment, the first layer has a first dielectric constant and the second layer has a second dielectric constant, wherein the first dielectric constant is greater than the second dielectric constant. In one embodiment, the first layer has a dielectric constant greater than about 25 and the second layer has a dielectric constant less than or equal to about 10. In one embodiment, the first layer comprises at least a portion of a dermis layer. In some embodiments, the second layer comprises at least a portion of a hypodermis layer or at least a portion of a glandular layer.

In another embodiment, disclosed is a method of creating a temperature gradient in the skin wherein the skin has at least an external surface, a first layer below the external surface and a second layer, the method comprising the steps of: positioning a device adapted to radiate electromagnetic energy adjacent the external surface; radiating electromagnetic energy from the device, the microwave energy having an electric field component which is substantially parallel to a region of the external surface; and generating a standing wave pattern in the first layer, the standing wave pattern having a constructive interference peak in the first layer, wherein a distance from the constructive interference peak to the skin surface is greater than a distance from the constructive interference peak to an interface between the first layer and the second layer.

In another embodiment, disclosed is a method of creating a lesion in a dermal layer of the skin, the dermal layer having an upper portion adjacent an external surface of the skin and a lower portion adjacent a subdermal layer of the skin, the method comprising the steps of: exposing the external surface to microwave energy having a predetermined power, frequency, and electric field orientation; generating a peak energy density region in the lower portion of the dermal layer; and continuing to radiate the skin with the microwave energy for a time sufficient to create a lesion, wherein the lesion begins in the peak energy density region.

In another embodiment, disclosed is a method of creating a lesion in a dermal layer of the skin wherein the skin has at least a dermal layer and a subdermal layer, the method comprising the steps of: positioning a device adapted to radiate microwave energy adjacent an external surface of the skin; and radiating microwave energy having an electric field component which is substantially parallel to a region of the external surface of the skin above the dermal layer, wherein the microwave energy has a frequency which generates a standing wave pattern in the dermal layer, the standing wave pattern having a constructive interference peak in the dermal layer in close proximity to an interface between the dermal layer and the subdermal layer.

In another embodiment, disclosed herein is a method of creating a lesion in a dermal layer of the skin wherein the skin has at least a dermal layer and a subdermal layer, the method comprising the steps of: positioning a device adapted to radiate microwave energy adjacent an external surface of the skin; radiating microwave energy having an electric field component which is substantially parallel to a region of the external surface of the skin above the dermal layer, wherein the microwave energy has a frequency which generates a standing wave pattern in the dermal layer, the standing wave pattern having a constructive interference peak in the dermal layer in close proximity to an interface between the dermal layer and the subdermal layer; and heating the lower portion of the dermal region using the radiated microwave energy to create the lesion. In one embodiment, a center of the lesion is positioned at the constructive interference peak.

In another embodiment, disclosed is a method of heating a tissue structure located in or near a target tissue layer, wherein the target tissue layer is below a first tissue layer, the first tissue layer being adjacent a skin surface, the method comprising the steps of: irradiating the target tissue layer and the first tissue layer through the skin surface with electromagnetic energy having predetermined frequency and electric field characteristics; and generating a power loss density profile wherein the power loss density profile has a peak power loss density in a region of the target tissue layer. In one embodiment, the tissue structure comprises a sweat gland. In one embodiment, heating the tissue structure is sufficient to destroy a pathogen located in or near the tissue structure. The pathogen may be bacteria. In some embodiments, the tissue structure is a sebaceous gland or at least a portion of a hair follicle. In some embodiments, the tissue structure may be selected from the group consisting of: telangiectasias, cellulite, varicose veins, and nerve endings. In one embodiment, heating the tissue structure is sufficient to damage the tissue structure. In one embodiment, the heat generates a lesion having an origin in the target tissue layer. The lesion grows to include the tissue structure. In one embodiment, the method further comprises the step of removing sufficient heat from the first layer to prevent the lesion from growing into the first layer. Removing sufficient heat from the first layer may comprise cooling the skin surface. In some embodiments, the target tissue layer may comprise a deep layer of the dermis or a glandular layer. In some embodiments, the electromagnetic energy has an electric field component which is substantially parallel to at least a portion of the skin surface or is parallel to at least a portion of the skin surface. In some embodiments, the electromagnetic energy radiates in a $TE_{10}$ mode or TEM mode. In some embodiments, the electromagnetic energy has a frequency in the range of between about 4 GHz and 10 GHz, 5 GHz and 6.5 GHz, or approximately 5.8 GHz. In one embodiment, the electromagnetic energy generates heat in the target tissue by dielectric heating. In one embodiment, the power loss density is generated by a standing wave pattern in the target tissue layer and the first tissue layer. The standing wave pattern may have a constructive interference peak in the region of the target tissue layer. The standing wave pattern may have a constructive interference minimum in the first tissue layer. In one embodiment, the origin of the lesion is in the region of the target tissue layer having the peak power loss density. In one embodiment, the lesion continues to grow through thermal conductive heating after electromagnetic energy is no longer applied. In one embodiment, the target tissue structure is heated primarily as a result of the thermal conductive heating.

In another embodiment, disclosed herein is a method of raising the temperature of at least a portion of a tissue structure located below an interface between a dermal layer and subdermal layer in skin, the dermal layer having an upper portion adjacent an external surface of the skin and a lower portion adjacent a subdermal region of the skin, the method comprising the steps of: radiating the skin with microwave energy having a predetermined power, frequency and e-field orientation; generating a peak energy density region in the lower portion of the dermal layer; initiating a lesion in the peak energy density region by dielectric heating of tissue in the peak energy density region; enlarging the lesion, wherein the lesion is enlarged, at least in part, by conduction of heat from the peak energy density region to surrounding tissue; removing heat from the skin surface and at least a portion of the upper portion of the dermal layer; and continuing to radiate the skin with the microwave energy for a time sufficient to extend the lesion past the interface and into the subdermal layer. In one embodiment, the tissue structure comprises a sweat gland.

Also disclosed herein in another embodiment is a method of raising the temperature of at least a portion of a tissue structure located below an interface between a dermal layer and a subdermal layer of skin, wherein the dermal layer has an upper portion adjacent an external surface of the skin and a lower portion adjacent a subdermal region of the skin, the method comprising the steps of: positioning a device adapted to radiate microwave energy adjacent the external surface of the skin; radiating microwave energy having an electric field component which is substantially parallel to a region of the external surface above the dermal layer, wherein the microwave energy has a frequency which generates a standing wave pattern in the dermal layer, the standing wave pattern having a constructive interference peak in the lower portion of the dermal layer; creating a lesion in the lower portion of the dermal region by heating tissue in the lower portion of the dermal region using the radiated microwave energy; removing heat from the skin surface and at least a portion of the upper portion of the dermal layer to prevent the lesion from spreading into the upper portion of the dermal layer; and ceasing the radiating after a first predetermined time, the predetermined time being sufficient to raise the temperature of the tissue structure. In some embodiments, the first predetermined time comprises a time sufficient to deposit enough energy in said lower portion of the dermal layer to enable said lesion to spread into the subdermal region or a time sufficient to enable heat generated by said radiation to spread to the tissue structure. In one embodiment, the step of removing heat further comprises continuing to remove heat for a predetermined time after the step of ceasing said radiating. In one embodiment, the constructive interference peak is located on a dermal side of the interface between the dermal layer and the subdermal layer. In one embodiment, the lesion starts at the constructive interference peak.

In another embodiment, disclosed herein is a method of controlling the application of microwave energy to tissue, the method comprising the steps of: generating a microwave signal having predetermined characteristics; applying the microwave energy to tissue, through a microwave antenna and a tissue interface operably connected to the microwave antenna; supplying a vacuum pressure to the tissue interface; and supplying cooling fluid to the tissue interface. In some embodiments, the microwave signal has a frequency in the range of between about 4 GHz and 10 GHz, between about 5 GHz and 6.5 GHz, or approximately 5.8 GHz. In one embodiment, the microwave antenna comprises an antenna configured to radiate electromagnetic radiation polarized such that an E-field component of the electromagnetic radiation is substantially parallel to an outer surface of the tissue. The microwave antenna may comprise a waveguide antenna. In some embodiments, the microwave antenna comprises an antenna configured to radiate in $TE_{10}$ mode or in TEM mode. In one embodiment, the tissue interface is configured to engage and hold skin. The skin may be in the axillary region. In one embodiment, the microwave antenna comprises an antenna configured to radiate electromagnetic radiation polarized such that an E-field component of the electromagnetic radiation is parallel to an outer surface of the tissue. In one embodiment, the tissue interface comprises a cooling plate and a cooling chamber positioned between the cooling plate and the microwave antenna. In one embodiment, the cooling plate has a dielectric constant between about 2 and 15. In one embodiment, the vacuum source is configured to supply vacuum pressure to the tissue interface. In some embodiments, the vacuum pressure is between about 400 mmHg to about 750 mmHg, or about 650 mmHg. In one embodiment, the cooling source is configured to supply a coolant to the tissue interface. In one embodiment, the coolant is a cooling fluid. In some embodiments, the cooling fluid has a dielectric constant of between about 70 and 90, or about 80, or between about 2 and 10, or about 2. In some embodiments, the cooling fluid has a temperature of between about −5° C. and 40° C. or between about 10° C. and 25° C. In one embodiment, the cooling fluid has a temperature of about 22° C. In some embodiments, the cooling fluid has a flow rate through at least a portion of the tissue interface of between about 100 mL and 600 mL per second or between about 250 mL and 450 mL per second. In one embodiment, the cooling fluid is configured to flow through the tissue interface at a velocity of between about 0.18 and 0.32 meters per second. In one embodiment, the cooling fluid is selected from the group consisting of glycerin, vegetable oil, isopropyl alcohol, and water, while in another embodiment, the cooling fluid is selected from the group consisting of water and water mixed with an alcohol.

Also disclosed, in another embodiment, is a method of positioning tissue prior to treating the tissue using radiated electromagnetic energy, the method comprising positioning a tissue interface adjacent a skin surface; engaging the skin surface in a tissue chamber of the tissue interface; substantially separating a layer comprising at least one layer of the skin from a muscle layer below the skin; and holding the skin surface in the tissue chamber. In one embodiment, the tissue interface comprises a tissue chamber, the tissue chamber having at least one wall and a tissue-contacting surface. In one embodiment, at least a portion of the tissue surface comprises a cooling plate positioned in the tissue chamber. In one embodiment, the tissue chamber has an aspect ratio in the range of between about 1:1 and 3:1, while in another embodiment, the tissue chamber has an aspect ratio of about 2:1. In one embodiment, the tissue chamber has a tissue acquisition angle between the wall and the tissue surface, the tissue acquisition angle being in the range of between about 2 degrees and approximately 45 degrees, while in another embodiment, the tissue acquisition angle is in the range of between about 5 degrees and approximately 20 degrees. In one embodiment, the tissue chamber has a tissue acquisition angle between the wall and the tissue surface, the tissue acquisition angle is about 20 degrees.

The various embodiments described herein can also be combined to provide further embodiments. Related methods, apparatuses and systems utilizing microwave and other types of therapy, including other forms of electromagnetic radiation, and further details on treatments that may be made with such therapies, are described in the above-referenced provisional applications to which this application claims priority, the entireties of each of which are hereby incorporated by reference: U.S. Provisional Patent Application Ser. No. 60/912,889, entitled "Methods and Apparatus for Reducing Sweat Production," filed Apr. 19, 2007, U.S. Provisional Patent Application Ser. No. 61/013,274, entitled "Methods, Delivery and Systems for Non-Invasive Delivery of Microwave Therapy," filed Dec. 12, 2007, and U.S. Provisional Patent Application Ser. No. 61/045,937, entitled "Systems and Methods for Creating an Effect Using Microwave Energy in Specified Tissue," filed Apr. 17, 2008. While the above-listed applications may have been incorporated by reference for particular subject matter as described earlier in this application, Applicants intend the entire disclosures of the above-identified applications to be incorporated by reference into the present application, in that any and all of the disclosures in these incorporated by reference applications may be combined and incorporated with the embodiments described in the present application.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A system for the application of microwave energy to skin, comprising:
   a signal generator adapted to generate a microwave signal having an electric field component;
   an applicator comprising one or more microwave antennas and a tissue interface, the applicator connected to the signal generator and adapted to apply the microwave signal to the skin, wherein the microwave signal has an electric field component;
   a tissue chamber adapted to move a skin surface into thermal contact with a cooling plate in the tissue interface, the cooling plate being oriented with respect to the antenna so as to be parallel with the electrical field component of the microwave signal;
   a vacuum source connected to the tissue chamber;
   a coolant source connected to said tissue interface and adapted to cool skin in thermal contact with the tissue interface; and
   a controller adapted to control the signal generator, the vacuum source, and the coolant source, wherein the one or more of the microwave antennas is configured to radiate the microwave energy into the skin, the microwave energy having a frequency and electric field orientation which generates a standing wave pattern having a constructive interference peak in a target tissue in the lower portion of the dermal layer of the skin, thereby creating a peak temperature at the target tissue, creating a lesion core;
   wherein the coolant source removes heat from the skin surface and at least an upper portion of the dermal skin layer to prevent the heat from spreading into an upper portion of the dermal skin layer;
   wherein the controller is configured to stop the application of the microwave energy after a predetermined time sufficient to raise the temperature of the tissue structure; and
   wherein the microwave signal has a frequency in the range of: between about 5 GHz and about 6.5 GHz.

2. The system of claim 1, wherein the controller is configured such that the system delivers energy such that a power loss density peak is created in the target tissue.

3. The system of claim 1, wherein the standing wave pattern is created by the reflection of at least a portion of the microwave energy off an interface between the dermal skin layer and the sub-dermal skin layer.

4. The system of claim 1, wherein the target tissue is in the glandular layer and the standing wave pattern is created by the reflection of at least a portion of the microwave energy off an interface between the glandular layer and the sub-dermal skin layer.

5. The system of claim 1, wherein the glandular layer comprises sweat glands.

6. The system of claim 1, wherein the target tissue comprises a sweat gland.

7. The system of claim 1, wherein the target tissue comprises a hair follicle.

8. A method of improving skin tissue by raising the temperature of a tissue structure, the method comprising the steps of:
   positioning a device adapted to radiate microwave energy adjacent an external surface of the skin;
   moving the skin surface into a vacuum chamber of the device to a position parallel to an output of a microwave antenna of the device;
   radiating microwave energy having a frequency of approximately 5.8 GHz and an electric field component which is substantially parallel to a region of the external surface of the skin, wherein the microwave energy has a frequency and e-field orientation which generates a standing wave pattern in a target tissue in the lower portion of the dermal layer of the skin by the reflection of at least a portion of the microwave energy off the interface between the dermal skin layer and the subdermal skin layer, the standing wave pattern having a constructive interference peak in the target tissue, thereby creating a peak temperature at the target tissue using the radiated microwave energy, creating a lesion core; and removing heat from the skin surface and an upper portion of the dermal skin layer to prevent heat from spreading into an upper portion of the dermal skin layer.

9. The method of claim 8, wherein the target tissue is in a glandular layer and the standing wave pattern is created by the reflection of at least a portion of the microwave energy off an interface between the glandular layer and the subdermal skin layer.

10. The method of claim 9, wherein the glandular layer comprises sweat glands.

11. The method of claim 8, wherein the target tissue comprises a sweat gland and wherein the method further comprises the step of radiating microwave energy to allow preferential heating of sweat glands.

12. The system of claim 8, wherein the tissue structure comprises a hair follicle.

\* \* \* \* \*